United States Patent
Kopecek et al.

(10) Patent No.: US 10,251,906 B2
(45) Date of Patent: Apr. 9, 2019

(54) COMPOSITIONS AND METHODS FOR INDUCING APOPTOSIS

(71) Applicant: University of Utah Research Foundation, Salt Lake City, UT (US)

(72) Inventors: Jindrich Henry Kopecek, Salt Lake City, UT (US); Jiyuan Yang, Salt Lake City, UT (US); Te-Wei Chu, Salt Lake City, UT (US)

(73) Assignee: UNIVERSITY OF UTAH RESEARCH FOUNDATION, Salt Lake City, GA (US)

( * ) Notice: Subject to any disclaimer, the term of this patent is extended or adjusted under 35 U.S.C. 154(b) by 185 days.

(21) Appl. No.: 14/773,791

(22) PCT Filed: Mar. 11, 2014

(86) PCT No.: PCT/US2014/023784
§ 371 (c)(1),
(2) Date: Sep. 9, 2015

(87) PCT Pub. No.: WO2014/164913
PCT Pub. Date: Oct. 9, 2014

(65) Prior Publication Data
US 2016/0015732 A1    Jan. 21, 2016

Related U.S. Application Data

(60) Provisional application No. 61/776,999, filed on Mar. 12, 2013.

(51) Int. Cl.
*A61K 31/712* (2006.01)
*C07K 16/28* (2006.01)
*A61K 47/58* (2017.01)
*A61K 47/68* (2017.01)
*A61K 39/00* (2006.01)

(52) U.S. Cl.
CPC ............ *A61K 31/712* (2013.01); *A61K 47/58* (2017.08); *A61K 47/6807* (2017.08); *A61K 47/6849* (2017.08); *A61K 47/6897* (2017.08); *C07K 16/2887* (2013.01); *A61K 2039/505* (2013.01); *C07K 2317/35* (2013.01); *C07K 2317/40* (2013.01); *C07K 2317/55* (2013.01); *C07K 2317/73* (2013.01)

(58) Field of Classification Search
None
See application file for complete search history.

(56) References Cited

U.S. PATENT DOCUMENTS

2003/0003102 A1*  1/2003  Hnatowich ...... A61K 47/48746
424/155.1

OTHER PUBLICATIONS

Wu et al. "Coiled-coil based drug-free macromolecular therapeutics:In vivo efficacy", Journal of Controlled Release 157 (2012) 126-131 (available online Aug. 6, 2011).*

* cited by examiner

*Primary Examiner* — Sharon X Wen
(74) *Attorney, Agent, or Firm* — Ballard Spahr LLP

(57) ABSTRACT

In an aspect, the invention relates to compositions, methods, and kits for inducing apoptosis. This abstract is intended as a scanning tool for purposes of searching in the particular art and is not intended to be limiting of the present invention.

14 Claims, 39 Drawing Sheets

Specification includes a Sequence Listing.

1. Non-treated 2. 1F5(1uM)+GAM (0.5uM) 3. 1F5(2uM)+GAM (1uM) 4. 1F5(5uM)+GAM (2.5uM) 5. Premix 1:1 (1uM)
6. Premix 1:1 (2uM) 7. Premix 1:1 (5uM) 8. Consecutive 1:1(1uM) 9. Consecutive 1:1(2uM) 10. Consecutive 1:1 (5uM)
11. P-MORF2 (5uM) 12. Fab'-MORF1 (1uM) 13. Fab'-MORF1(2uM) 14. Fab'-MORF1 (5uM)

| No. | (P-TT polymer precursor) | | | | (P-MORF2) |
|---|---|---|---|---|---|
| | Mn | Pd | TT/P | FITC/P | MORF2/P |
| #1 | 70 kDa | 1.08 | 17.9 | 3.7 | ~2 |
| #2 | 92 kDa | 1.04 | 34.1 | / | 3.4 |
| #3 | 136 kDa | 1.15 | 73.3 | / | 9.6 |

Note: P-MORF2 #1 containing FITC was used for confocal fluorescence microscopy studies only.

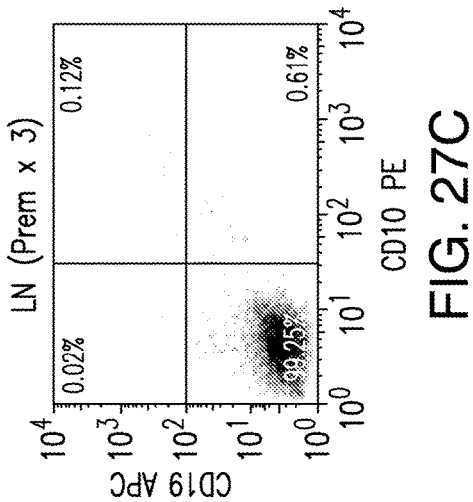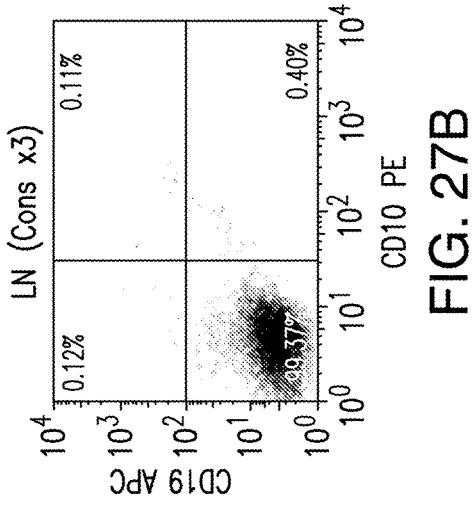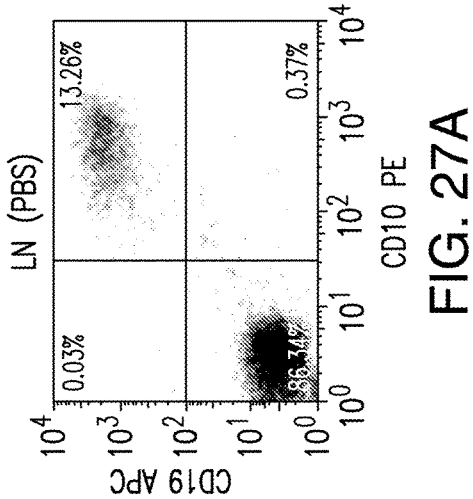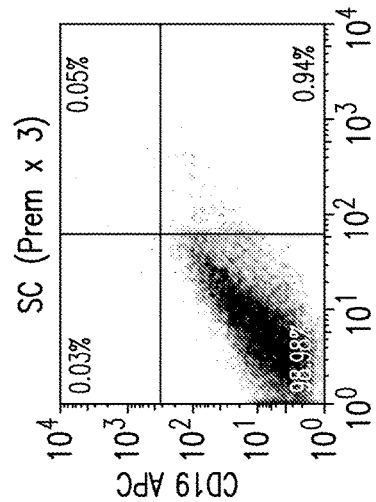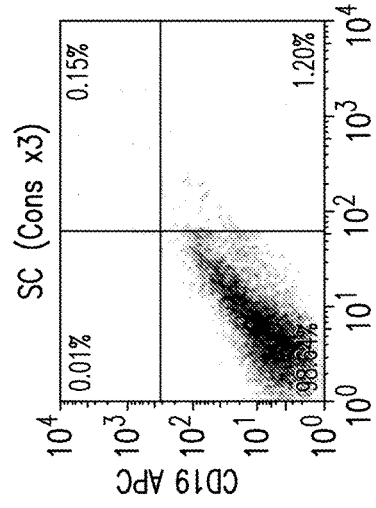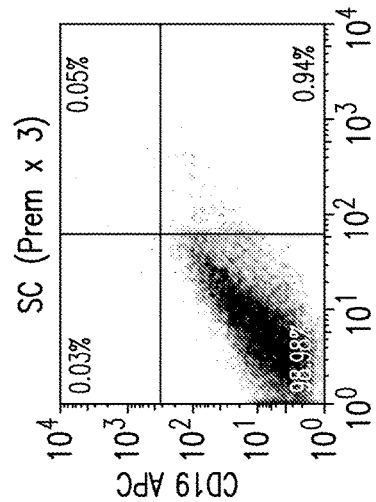

SEQUENCE LISTING

```
<160> NUMBER OF SEQ ID NOS: 63

<210> SEQ ID NO 1
<211> LENGTH: 40
<212> TYPE: DNA
<213> ORGANISM: Artificial Sequence
<220> FEATURE:
<223> OTHER INFORMATION: synthetic construct; morpholino MORF1-a

<400> SEQUENCE: 1
gaactaatgc aataactatc acgaatgcgg gtaacttaat                              40

<210> SEQ ID NO 2
<211> LENGTH: 40
<212> TYPE: DNA
<213> ORGANISM: Artificial Sequence
<220> FEATURE:
<223> OTHER INFORMATION: synthetic construct; morpholino MORF2-a

<400> SEQUENCE: 2
attaagttac ccgcattcgt gatagttatt gcattagttc                              40

<210> SEQ ID NO 3
<211> LENGTH: 40
<212> TYPE: DNA
<213> ORGANISM: Artificial Sequence
<220> FEATURE:
<223> OTHER INFORMATION: synthetic construct; morpholino MORF1-b

<400> SEQUENCE: 3
gaaaccgcta tttattggct aagaacagat acgaatcata                              40

<210> SEQ ID NO 4
<211> LENGTH: 40
<212> TYPE: DNA
<213> ORGANISM: Artificial Sequence
<220> FEATURE:
<223> OTHER INFORMATION: synthetic construct; morpholino MORF2-b

<400> SEQUENCE: 4
tatgattcgt atctgttctt agccaataaa tagcggtttc                              40

<210> SEQ ID NO 5
<211> LENGTH: 38
<212> TYPE: DNA
<213> ORGANISM: Artificial Sequence
<220> FEATURE:
```

<223> OTHER INFORMATION: synthetic construct; morpholino MORF1-c

<400> SEQUENCE: 5
gtaaacgcga caaatgccga taatgcttcg ataataat                    38

<210> SEQ ID NO 6
<211> LENGTH: 38
<212> TYPE: DNA
<213> ORGANISM: Artificial Sequence
<220> FEATURE:
<223> OTHER INFORMATION: synthetic construct; morpholino MORF2-c

<400> SEQUENCE: 6
attattatcg aagcattatc ggcatttgtc gcgtttac                    38

<210> SEQ ID NO 7
<211> LENGTH: 38
<212> TYPE: DNA
<213> ORGANISM: Artificial Sequence
<220> FEATURE:
<223> OTHER INFORMATION: synthetic construct; morpholino MORF1-d

<400> SEQUENCE: 7
gacagagttc actatgacaa acgatttcac gagtaata                    38

<210> SEQ ID NO 8
<211> LENGTH: 38
<212> TYPE: DNA
<213> ORGANISM: Artificial Sequence
<220> FEATURE:
<223> OTHER INFORMATION: synthetic construct; morpholino MORF2-d

<400> SEQUENCE: 8
gacagagttc actatgacaa acgatttcac gagtaata                    38

<210> SEQ ID NO 9
<211> LENGTH: 35
<212> TYPE: DNA
<213> ORGANISM: Artificial Sequence
<220> FEATURE:
<223> OTHER INFORMATION: synthetic construct; morpholino MORF1-e

<400> SEQUENCE: 9
cctgatacag aagtagaaag cagtcacgca atata                       35

<210> SEQ ID NO 10
<211> LENGTH: 35
<212> TYPE: DNA
<213> ORGANISM: Artificial Sequence
<220> FEATURE:
<223> OTHER INFORMATION: synthetic construct; morpholino MORF2-e

<400> SEQUENCE: 10
tatattgcgt gactgctttc tacttctgta tcagg                       35

<210> SEQ ID NO 11
<211> LENGTH: 35
<212> TYPE: DNA
<213> ORGANISM: Artificial Sequence
<220> FEATURE:
<223> OTHER INFORMATION: synthetic construct; morpholino MORF1-f

<400> SEQUENCE: 11
gaacaacgag aggtgctcaa tacagatatc aatca                       35

```
<210> SEQ ID NO 12
<211> LENGTH: 35
<212> TYPE: DNA
<213> ORGANISM: Artificial Sequence
<220> FEATURE:
<223> OTHER INFORMATION: synthetic construct; morpholino MORF2-f

<400> SEQUENCE: 12
tgattgatat ctgtattgag cacctctcgt tgttc                                35

<210> SEQ ID NO 13
<211> LENGTH: 32
<212> TYPE: DNA
<213> ORGANISM: Artificial Sequence
<220> FEATURE:
<223> OTHER INFORMATION: synthetic construct; morpholino MORF1-g

<400> SEQUENCE: 13
agtcatagat agacagaata gccggataaa ct                                   32

<210> SEQ ID NO 14
<211> LENGTH: 32
<212> TYPE: DNA
<213> ORGANISM: Artificial Sequence
<220> FEATURE:
<223> OTHER INFORMATION: synthetic construct; morpholino MORF2-g

<400> SEQUENCE: 14
agtttatccg gctattctgt ctatctatga ct                                   32

<210> SEQ ID NO 15
<211> LENGTH: 32
<212> TYPE: DNA
<213> ORGANISM: Artificial Sequence
<220> FEATURE:
<223> OTHER INFORMATION: synthetic construct; morpholino MORF1-h

<400> SEQUENCE: 15
gatacagaag tagaaagcag tcacgcaata ta                                   32

<210> SEQ ID NO 16
<211> LENGTH: 32
<212> TYPE: DNA
<213> ORGANISM: Artificial Sequence
<220> FEATURE:
<223> OTHER INFORMATION: synthetic construct; morpholino MORF2-h

<400> SEQUENCE: 16
tatattgcgt gactgctttc tacttctgta tc                                   32

<210> SEQ ID NO 17
<211> LENGTH: 30
<212> TYPE: DNA
<213> ORGANISM: Artificial Sequence
<220> FEATURE:
<223> OTHER INFORMATION: synthetic construct; morpholino MORF1-i

<400> SEQUENCE: 17
ggcatagata acagaatagc cggataaact                                      30

<210> SEQ ID NO 18
<211> LENGTH: 30
<212> TYPE: DNA
<213> ORGANISM: Artificial Sequence
<220> FEATURE:
<223> OTHER INFORMATION: synthetic construct; morpholino MORF2-i
```

<400> SEQUENCE: 18
agtttatccg gctattctgt tatctatgcc                                  30

<210> SEQ ID NO 19
<211> LENGTH: 30
<212> TYPE: DNA
<213> ORGANISM: Artificial Sequence
<220> FEATURE:
<223> OTHER INFORMATION: synthetic construct; morpholino MORF1-j

<400> SEQUENCE: 19
gaccagtaga taagtgaacc agattgaaca                                  30

<210> SEQ ID NO 20
<211> LENGTH: 30
<212> TYPE: DNA
<213> ORGANISM: Artificial Sequence
<220> FEATURE:
<223> OTHER INFORMATION: synthetic construct; morpholino MORF2-j

<400> SEQUENCE: 20
tgttcaatct ggttcactta tctactggtc                                  30

<210> SEQ ID NO 21
<211> LENGTH: 28
<212> TYPE: DNA
<213> ORGANISM: Artificial Sequence
<220> FEATURE:
<223> OTHER INFORMATION: synthetic construct; morpholino MORF1-k

<400> SEQUENCE: 21
gagtacagcc agagagagaa tcaatata                                    28

<210> SEQ ID NO 22
<211> LENGTH: 28
<212> TYPE: DNA
<213> ORGANISM: Artificial Sequence
<220> FEATURE:
<223> OTHER INFORMATION: synthetic construct; morpholino MORF2-k

<400> SEQUENCE: 22
tatattgatt ctctctctgg ctgtactc                                    28

<210> SEQ ID NO 23
<211> LENGTH: 28
<212> TYPE: DNA
<213> ORGANISM: Artificial Sequence
<220> FEATURE:
<223> OTHER INFORMATION: synthetic construct; morpholino MORF1-l

<400> SEQUENCE: 23
gtgaacacga aagagtgacg caataaat                                    28

<210> SEQ ID NO 24
<211> LENGTH: 28
<212> TYPE: DNA
<213> ORGANISM: Artificial Sequence
<220> FEATURE:
<223> OTHER INFORMATION: synthetic construct; morpholino MORF2-l

<400> SEQUENCE: 24
atttattgcg tcactctttc gtgttcac                                    28

<210> SEQ ID NO 25
<211> LENGTH: 25

```
<212> TYPE: DNA
<213> ORGANISM: Artificial Sequence
<220> FEATURE:
<223> OTHER INFORMATION: synthetic construct; morpholino MORF1-m

<400> SEQUENCE: 25
gagtaagcca aggagaatca atata                                         25

<210> SEQ ID NO 26
<211> LENGTH: 25
<212> TYPE: DNA
<213> ORGANISM: Artificial Sequence
<220> FEATURE:
<223> OTHER INFORMATION: synthetic construct; morpholino MORF2-m

<400> SEQUENCE: 26
tatattgatt ctccttggct tactc                                         25

<210> SEQ ID NO 27
<211> LENGTH: 25
<212> TYPE: DNA
<213> ORGANISM: Artificial Sequence
<220> FEATURE:
<223> OTHER INFORMATION: synthetic construct; morpholino MORF1-n

<400> SEQUENCE: 27
agatgacgat aaagacgcaa agatt                                         25

<210> SEQ ID NO 28
<211> LENGTH: 25
<212> TYPE: DNA
<213> ORGANISM: Artificial Sequence
<220> FEATURE:
<223> OTHER INFORMATION: synthetic construct; morpholino MORF2-n

<400> SEQUENCE: 28
aatctttgcg tctttatcgt catct                                         25

<210> SEQ ID NO 29
<211> LENGTH: 23
<212> TYPE: DNA
<213> ORGANISM: Artificial Sequence
<220> FEATURE:
<223> OTHER INFORMATION: synthetic construct; morpholino MORF1-o

<400> SEQUENCE: 29
ggaccaagta aacagggata tat                                           23

<210> SEQ ID NO 30
<211> LENGTH: 23
<212> TYPE: DNA
<213> ORGANISM: Artificial Sequence
<220> FEATURE:
<223> OTHER INFORMATION: synthetic construct; morpholino MORF2-o

<400> SEQUENCE: 30
atatatccct gtttacttgg tcc                                           23

<210> SEQ ID NO 31
<211> LENGTH: 23
<212> TYPE: DNA
<213> ORGANISM: Artificial Sequence
<220> FEATURE:
<223> OTHER INFORMATION: synthetic construct; morpholino MORF1-p

<400> SEQUENCE: 31
```

```
gctgaaaacc aatatgagag tga                                           23

<210> SEQ ID NO 32
<211> LENGTH: 23
<212> TYPE: DNA
<213> ORGANISM: Artificial Sequence
<220> FEATURE:
<223> OTHER INFORMATION: synthetic construct; morpholino MORF2-p

<400> SEQUENCE: 32
tcactctcat attggttttc agc                                           23

<210> SEQ ID NO 33
<211> LENGTH: 20
<212> TYPE: DNA
<213> ORGANISM: Artificial Sequence
<220> FEATURE:
<223> OTHER INFORMATION: synthetic construct; morpholino MORF1-q

<400> SEQUENCE: 33
gatgaagtac cgacaagata                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic construct; morpholino MORF2-q

<400> SEQUENCE: 34
tatcttgtcg gtacttcatc                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic construct; morpholino MORF1-r

<400> SEQUENCE: 35
gacaggatga ataacacagt                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic construct; morpholino MORF2-r

<400> SEQUENCE: 36
actgtgttat tcatcctgtc                                               20

<210> SEQ ID NO 37
<211> LENGTH: 18
<212> TYPE: DNA
<213> ORGANISM: Artificial Sequence
<220> FEATURE:
<223> OTHER INFORMATION: synthetic construct; morpholino MORF1-s

<400> SEQUENCE: 37
gcagcaaacg aagtatat                                                 18

<210> SEQ ID NO 38
<211> LENGTH: 18
<212> TYPE: DNA
<213> ORGANISM: Artificial Sequence
```

```
<220> FEATURE:
<223> OTHER INFORMATION: synthetic construct; morpholino MORF2-s

<400> SEQUENCE: 38
atatacttcg tttgctgc                                                  18

<210> SEQ ID NO 39
<211> LENGTH: 18
<212> TYPE: DNA
<213> ORGANISM: Artificial Sequence
<220> FEATURE:
<223> OTHER INFORMATION: synthetic construct; morpholino MORF1-t

<400> SEQUENCE: 39
gtcataacag aacaggta                                                  18

<210> SEQ ID NO 40
<211> LENGTH: 18
<212> TYPE: DNA
<213> ORGANISM: Artificial Sequence
<220> FEATURE:
<223> OTHER INFORMATION: synthetic construct; morpholino MORF2-t

<400> SEQUENCE: 40
tacctgttct gttatgac                                                  18

<210> SEQ ID NO 41
<211> LENGTH: 15
<212> TYPE: DNA
<213> ORGANISM: Artificial Sequence
<220> FEATURE:
<223> OTHER INFORMATION: synthetic construct; morpholino MORF1-u

<400> SEQUENCE: 41
tcaagacaga aggat                                                     15

<210> SEQ ID NO 42
<211> LENGTH: 15
<212> TYPE: DNA
<213> ORGANISM: Artificial Sequence
<220> FEATURE:
<223> OTHER INFORMATION: synthetic construct; morpholino MORF2-u

<400> SEQUENCE: 42
atccttctgt cttga                                                     15

<210> SEQ ID NO 43
<211> LENGTH: 15
<212> TYPE: DNA
<213> ORGANISM: Artificial Sequence
<220> FEATURE:
<223> OTHER INFORMATION: synthetic construct; morpholino MORF1-v

<400> SEQUENCE: 43
tagcaacata ggaag                                                     15

<210> SEQ ID NO 44
<211> LENGTH: 15
<212> TYPE: DNA
<213> ORGANISM: Artificial Sequence
<220> FEATURE:
<223> OTHER INFORMATION: synthetic construct; morpholino MORF2-v

<400> SEQUENCE: 44
cttcctatgt tgcta                                                     15
```

```
<210> SEQ ID NO 45
<211> LENGTH: 12
<212> TYPE: DNA
<213> ORGANISM: Artificial Sequence
<220> FEATURE:
<223> OTHER INFORMATION: synthetic construct; morpholino MORF1-w

<400> SEQUENCE: 45
cagagagcat at                                                          12

<210> SEQ ID NO 46
<211> LENGTH: 12
<212> TYPE: DNA
<213> ORGANISM: Artificial Sequence
<220> FEATURE:
<223> OTHER INFORMATION: synthetic construct; morpholino MORF2-w

<400> SEQUENCE: 46
atatgctctc tg                                                          12

<210> SEQ ID NO 47
<211> LENGTH: 12
<212> TYPE: DNA
<213> ORGANISM: Artificial Sequence
<220> FEATURE:
<223> OTHER INFORMATION: synthetic construct; morpholino MORF1-x

<400> SEQUENCE: 47
caagaggtac at                                                          12

<210> SEQ ID NO 48
<211> LENGTH: 12
<212> TYPE: DNA
<213> ORGANISM: Artificial Sequence
<220> FEATURE:
<223> OTHER INFORMATION: synthetic construct; morpholino MORF2-x

<400> SEQUENCE: 48
atgtacctct tg                                                          12

<210> SEQ ID NO 49
<211> LENGTH: 10
<212> TYPE: DNA
<213> ORGANISM: Artificial Sequence
<220> FEATURE:
<223> OTHER INFORMATION: synthetic construct; morpholino MORF1-y

<400> SEQUENCE: 49
aagaggtaca                                                             10

<210> SEQ ID NO 50
<211> LENGTH: 10
<212> TYPE: DNA
<213> ORGANISM: Artificial Sequence
<220> FEATURE:
<223> OTHER INFORMATION: synthetic construct; MORF2-y

<400> SEQUENCE: 50
tgtacctctt                                                             10

<210> SEQ ID NO 51
<211> LENGTH: 10
<212> TYPE: DNA
<213> ORGANISM: Artificial Sequence
<220> FEATURE:
<223> OTHER INFORMATION: synthetic construct; morpholino MORF1-z
```

```
<400> SEQUENCE: 51
aaggacagta                                                          10

<210> SEQ ID NO 52
<211> LENGTH: 10
<212> TYPE: DNA
<213> ORGANISM: Artificial Sequence
<220> FEATURE:
<223> OTHER INFORMATION: synthetic construct; morpholino MORF2-z

<400> SEQUENCE: 52
tactgtcctt                                                          10

<210> SEQ ID NO 53
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 53
aaaaaaaaaa aaaaaaaaaa aaaaa                                         25

<210> SEQ ID NO 54
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 54
tttttttttt tttttttttt ttttt                                         25

<210> SEQ ID NO 55
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 55
aagaagaaga agaagaagaa gaaga                                         25

<210> SEQ ID NO 56
<211> LENGTH: 15
<212> TYPE: DNA
<213> ORGANISM: Artificial Sequence
<220> FEATURE:
<223> OTHER INFORMATION: synthetic construct; morpholino

<400> SEQUENCE: 56
tagttgtgac gtaca                                                    15

<210> SEQ ID NO 57
<211> LENGTH: 15
<212> TYPE: DNA
<213> ORGANISM: Artificial Sequence
<220> FEATURE:
<223> OTHER INFORMATION: synthetic construct; morpholino

<400> SEQUENCE: 57
atcaacactg cttgt                                                    15

<210> SEQ ID NO 58
```

```
<211> LENGTH: 18
<212> TYPE: DNA
<213> ORGANISM: Artificial Sequence
<220> FEATURE:
<223> OTHER INFORMATION: synthetic construct; morpholino

<400> SEQUENCE: 58
atcaacactg cttgtggg                                                   18

<210> SEQ ID NO 59
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 59
atcaacactg cttgtgggtg gtggt                                           25

<210> SEQ ID NO 60
<211> LENGTH: 18
<212> TYPE: DNA
<213> ORGANISM: Artificial Sequence
<220> FEATURE:
<223> OTHER INFORMATION: synthetic construct; morpholino

<400> SEQUENCE: 60
tagttgtgac gtacaccc                                                   18

<210> SEQ ID NO 61
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 61
tagttgtgac gtacacccac cacca                                           25

<210> SEQ ID NO 62
<211> LENGTH: 20
<212> TYPE: DNA
<213> ORGANISM: Artificial Sequence
<220> FEATURE:
<223> OTHER INFORMATION: synthetic construct; morpholino

<400> SEQUENCE: 62
caccaccccc ctcgctggtc                                                 20

<210> SEQ ID NO 63
<211> LENGTH: 25
<212> TYPE: DNA
<213> ORGANISM: Artificial Sequence
<220> FEATURE:
<223> OTHER INFORMATION: synthetic construct; morpholino

<400> SEQUENCE: 63
cccccccccc cccccccccc ccccc                                           25
```

COMPOSITIONS AND METHODS FOR INDUCING APOPTOSIS

CROSS-REFERENCE TO RELATED APPLICATION

The present application is a National Phase Under 35 U.S.C. § 371 of International Application No. PCT/US2014/012355, filed Jan. 21, 2014, which claims the benefit of the filing dates of U.S. Provisional Patent Application No. 61/776,999, filed Mar. 12, 2013. Each of the above-referenced patent applications are hereby incorporated by reference herein in its entirety.

STATEMENT REGARDING FEDERALLY SPONSORED RESEARCH OR DEVELOPMENT

This invention was made with government support under GM095606 awarded by the National Institutes of Health. The government has certain rights in the invention.

REFERENCE TO SEQUENCE LISTING

The Sequence Listing submitted Sep. 9, 2015 as a text file named "21101_0283U2_Sequence_Listing.txt," created on Sep. 4, 2015, and having a size of 13,623 bytes is hereby incorporated by reference pursuant to 37 C.F.R. § 1.52(e)(5).

BACKGROUND OF THE INVENTION

Drug free macromolecular therapeutic platforms possess great potential for treatment of several diseases and disorders. For example, the cross-linking of CD20 followed by the induction of apoptosis as described herein can be used to treat several diseases and disorders including B cell malignancies, inflammatory disorders, and auto-immune diseases with B cell involvement.

Non-Hodgkin's lymphoma (NHL) is a prevalent cancer worldwide with a high mortality rate. In 2012, in the United States alone, there were 70,130 new cases of NHL and 18,940 deaths attributed to NHL. About 85% of NHLs are malignancies originating from B-cells while the remaining malignancies are of T cell origin. B-cell NHLs include Burkitt's, diffuse large B-cell, follicular, immunoblastic large cell, precursor B-lymphoblastic, and mantle cell lymphomas. These cancers are generally classified as either indolent or aggressive, and more than 95% of B-cell lymphomas bear the cell surface antigen CD20. Anti-CD20 monoclonal antibodies (mAbs), mainly rituximab, are commonly used immunotherapies for NHL patients. However, the immunotherapy has a low overall response rate (<50% for relapsed/refractory NHL) and can produce rare but lethal side effects (e.g., progressive multifocal leukoencephalopathy). Many researchers have attributed the clinical non-responsiveness and the adverse effects of anti-CD20 monoclonal antibodies to the Fc-induced cellular events.

There is still a scarcity of compositions and methods that are effective in the treatment of B cell malignancies, inflammatory disorders, and auto-immune diseases with B cell involvement. These needs and other needs are satisfied by the present invention.

BRIEF SUMMARY OF THE INVENTION

Disclosed herein are complexes comprising a targeting moiety and an oligonucleotide.

Disclosed herein are complexes comprising a targeting moiety and an oligonucleotide, wherein the targeting moiety is a Fab' fragment, wherein the Fab' fragment is specific for a CD20 receptor, wherein the oligonucleotide is a morpholino, and wherein the Fab' fragment is conjugated to the morpholino via a thioether bond.

Disclosed herein are complexes comprising a copolymer carrier and one or more oligonucleotides.

Disclosed herein are complexes comprising a copolymer carrier and one or more oligonucleotides, wherein the copolymer carrier comprises a main chain and one or more side chains, wherein the copolymer carrier comprises N-(2-hydroxypropyl)methylacrylamide copolymerized with N-methacryloylglycylglycine-thiazolidine-2-thione monomers, wherein the one or more side chains can be conjugated to the one or more oligonucleotides, wherein the one or more oligonucleotides are morpholinos.

Disclosed herein are kits comprising a first complex comprising a targeting moiety and an oligonucleotide, and a second complex comprising a copolymer carrier and one or more oligonucleotides.

Disclosed herein are kits comprising a first complex comprising a targeting moiety and an oligonucleotide, a second complex comprising a copolymer carrier and one or more oligonucleotides, and instructions for administering the first complex and the second complex.

Disclosed herein are methods of inducing apoptosis, the method comprising contacting a population of cells with a first complex comprising a targeting moiety and an oligonucleotide; and contacting a population of cells with a second complex comprising a copolymer carrier and one or more oligonucleotides; wherein the contacting of the cells with the first complex and the second complex induces apoptosis of the cells.

Disclosed herein are methods of inducing apoptosis, the method comprising contacting a population of cells with a composition comprising a first complex comprising a targeting moiety and an oligonucleotide and a second complex comprising a complex comprising a copolymer carrier and one or more oligonucleotides, wherein the contacting of the cells with the composition induces apoptosis of the cells.

Disclosed herein are methods of treatment of a subject in need thereof, the method comprising administering to a subject a first composition comprising a first complex comprising a targeting moiety and an oligonucleotide; and administering to the subject a second composition comprising a second complex comprising a copolymer carrier and one or more oligonucleotides, wherein the administering of the first composition and the second composition induces apoptosis of a targeted population of cells in the subject.

Disclosed herein are processes of synthesizing a complex comprising a targeting moiety and an oligonucleotide, the process comprising obtaining a targeting moiety, modifying an oligonucleotide, and conjugating the targeting moiety to the oligonucleotide.

Disclosed herein are processes of synthesizing a complex comprising a copolymer carrier and one or more oligonucleotides, the process comprising obtaining a copolymer carrier, modifying one or more oligonucleotides, and conjugating the copolymer carrier to one or more oligonucleotides.

Disclosed herein are processes of synthesizing a complex comprising a targeting moiety and an oligonucleotide and a complex comprising a copolymer carrier and one or more oligonucleotides, the process comprising contacting a first complex comprising a targeting moiety and an oligonucleotide with a second complex comprising a copolymer carrier to one or more oligonucleotides.

BRIEF DESCRIPTION OF THE SEVERAL VIEWS OF THE DRAWINGS

The accompanying Figures, which are incorporated in and constitute a part of this specification, illustrate several aspects of the invention and together with the description serve to explain the principles of the invention.

FIG. 27A-FIG. 27F show flow cytometry analysis of residual Raji B-cells in different organs/tissues of the tumor-bearing mice that underwent different treatments.

Figure 1:
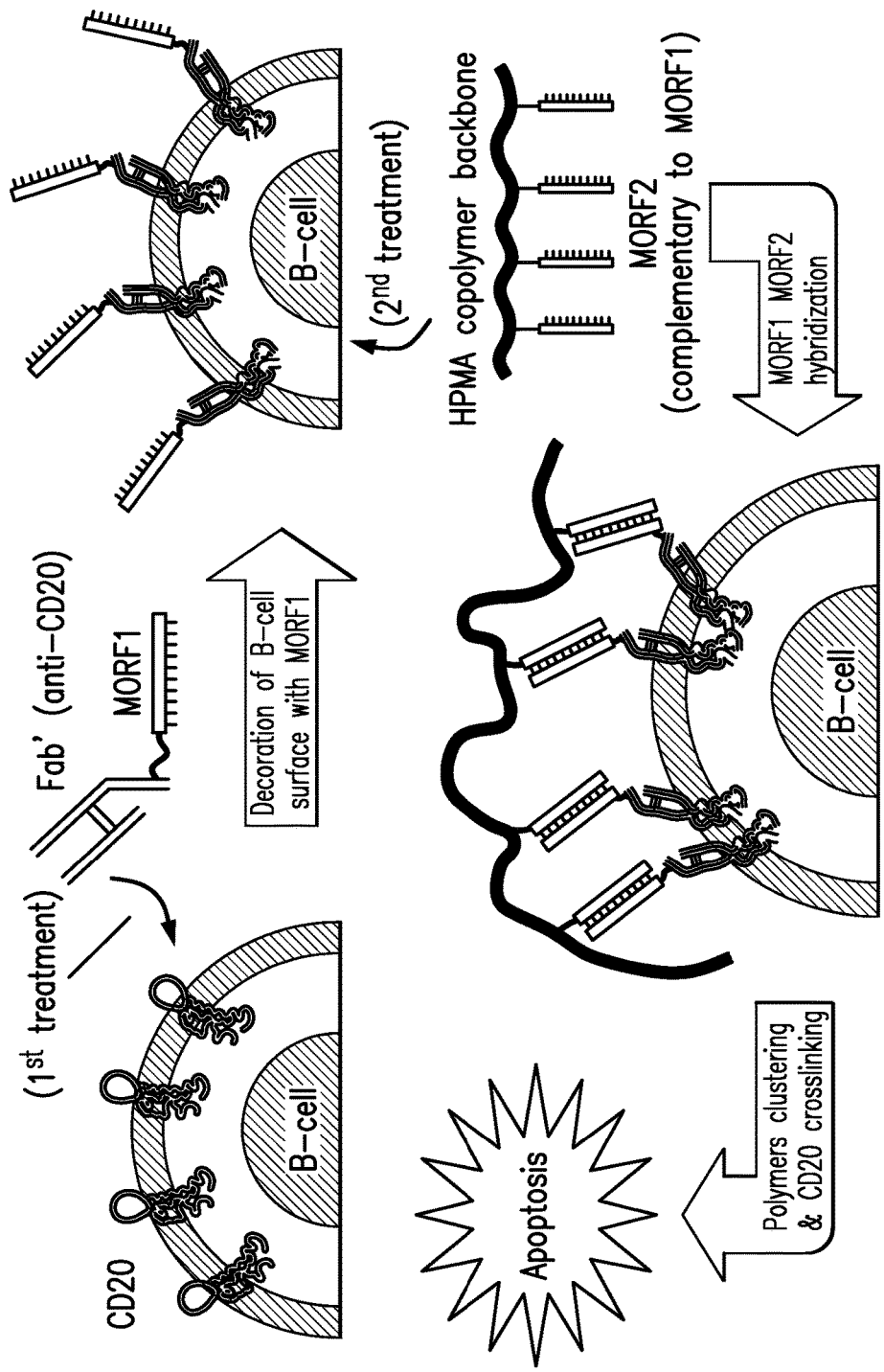
FIG. 1 shows a schematic outlining an exemplary design of a drug-free macromolecular therapeutic platform for B-cell depletion using CD20-crosslinking mediated apoptosis induced by oligonucleotide hybridization.

Additional advantages of the invention are set forth in part in the description that follows, and in part will be obvious from the description, or can be learned by practice of the invention. It is to be understood that both the foregoing general description and the following detailed description are exemplary and are not restrictive of the invention as claimed.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. DEFINITIONS

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a complex comprising a targeting moiety and an oligonucleotide can optionally comprise a detectable label. In an aspect, a disclosed method can optionally comprise repeating the administration of a disclosed composition and/or complex.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, "homolog" or "homologue" refers to a polypeptide or nucleic acid with homology to a specific known sequence. Specifically disclosed are variants of the nucleic acids and polypeptides herein disclosed which have at least 40, 41, 42, 43, 44, 45, 46, 47, 48, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more percent homology to the stated or known sequence. Those of skill in the art readily understand how to determine the homology of two or more proteins or two or more nucleic acids. For example, the homology can be calculated after aligning the two or more sequences so that the homology is at its highest level. It is understood that one way to define any variants, modifications, or derivatives of the disclosed genes and proteins herein is through defining the variants, modification, and derivatives in terms of homology to specific known sequences.

As used herein, "aptamers" refer to molecules that interact with a target molecule, preferably in a specific way. Typically, aptamers are small nucleic acids ranging from 15-50 bases in length that fold into defined secondary and tertiary structures, such as stem-loops or G-quartets. Aptamers can bind small molecules and large molecules. Aptamers can bind very tightly with Kd's from the target molecule of less than $10^{-12}$ M. Aptamers can bind the target molecule with a very high degree of specificity. Aptamers are known to the art and representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

As used herein, a "targeting moiety" can be specific to a recognition molecule on the surface of a cell or a population of cells, such as, for example B-cells. In an aspect of the disclosed compositions and methods, a targeting moiety can include, but is not limited to: a monoclonal antibody, a polyclonal antibody, full-length antibody, a chimeric antibody, Fab', Fab, F(ab)$_2$, F(ab')$_2$, a single domain antibody (DAB), Fv, a single chain Fv (scFv), a minibody, a diabody, a triabody, hybrid fragments, a phage display antibody, a ribosome display antibody, a peptide, a peptide ligand, a hormone, a growth factor, a cytokine, a saccharide or polysaccharide, and an aptamer.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient.

A patient refers to a subject afflicted with one or more diseases or disorders, such as, for example, a B cell malignancy, an inflammatory disorder, and an autoimmune disease with B cell involvement. In an aspect, diseases and disorders include, but are not limited to: non-Hodgkin's lymphoma, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a patient has JC virus. In an aspect, a patient has received an organ transplant. In an aspect of a disclosed method, a patient has been diagnosed with a need for treatment of one or more of the aforementioned diseases or disorders prior to the administering step. In an aspect of a disclosed method, a patient has been diagnosed with a need for inducing apoptosis of malignant cells, such as, for example, malignant B-cells.

As used herein, "non-Hodgkin's lymphoma" or "NHL" refers to a cancer of the lympathic tissue. As a heterogenous condition, NHL can cause enlargement of lymph nodes and generalized systems.

As used herein, the term "treatment" refers to the medical management of a patient with the intent to cure, ameliorate, stabilize, or prevent a disease, pathological condition, or disorder (such as, for example, B-cell malignancies, inflammatory disorders, and auto-immune diseases with B cell involvement). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In an aspect, preventing malignant cell growth is intended.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with NHL" means having been subjected to a physical examination by a person of skill, for example, a physician, and found to have a condition that can be diagnosed or can be treated by a compound or composition that can prevent or inhibit malignant cell growth and/or induce apoptosis in a population of cells, such as B-cells. As a further example, "diagnosed with a need for inducing apoptosis" refers to having been subjected to a physical examination by a person of skill, for example, a physician, and found to have a condition characterized by malignant cell growth or other disease wherein inducing apoptosis of a population of cells would be beneficial to the subject. Such a diagnosis can be in reference to a disorder, such as NHL, and the like, as discussed herein.

As used herein, "one or more oligonucleotides" can refer to "one or more morpholinos". For example, in an aspect a disclosed copolymer carrier can comprise one or more grafted oligonucleotides or can comprise one or more grafted morpholinos. In an aspect, "one or more oligonucleotides" or "one or more morpholinos" can comprise 1 morpholino, or 2 morpholinos, or 3 morpholinos, or 4 morpholinos, or 5 morpholinos, or 6 morpholinos, or 7 morpholinos, or 8 morpholinos, or 9 morpholinos, or 10 morpholinos. For example, in an aspect, a disclosed copolymer can comprise 1 morpholino. In an aspect, a disclosed copolymer can comprise 3 morpholinos. In an aspect, a disclosed copolymer can comprise 10 morpholinos. In an aspect, a disclosed copolymer can comprise more than 10 grafted morpholinos. In an aspect, the one or more morpholinos can comprise one or more grafted MORF2 morpholinos. For example, a disclosed copolymer-MORF2 complex can comprise 1 grafted morpholino, or 3 grafted morpholinos, or 10 grafted morpholinos, or more than 10 grafted morpholinos. For example, a disclosed copolymer-MORF2 complex can comprise 1 grafted MORF2, or 3 grafted MORF2, or 10 grafted MORF2, or more than 10 grafted MORF2.

As used herein, the phrase "identified to be in need of treatment for a disorder," or the like, refers to selection of a subject based upon need for treatment of the disorder. For example, a subject can be identified as having a need for treatment of a disorder (e.g., NHL or some other disorder related to malignant cell growth or a disorder requiring apoptosis of a population of cells) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who performed the diagnosis.

As used herein, the terms "administering" and "administration" refer to any method of providing a disclosed composition, complex, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration for a disclosed composition or a disclosed complex so as to treat a subject or induce apoptosis. In an aspect, the skilled person can also alter or modify an aspect of an administering step so as to improve efficacy of a disclosed complex or disclosed composition.

As used herein, "altering one or more administering steps" can comprise changing or modifying the administration of one or more disclosed compositions or disclosed complexes. In an aspect, administering the complex comprising a targeting moiety and an oligonucleotide can be altered, for example, by changing the route of administration, or changing the dose of the composition, or changing the timing of administration, or changing the frequency of the administration, or a combination thereof. In an aspect, administering the complex comprising a copolymer carrier and one or more oligonucleotides can be altered, for example, by changing the route of administration, or changing the dose of the composition, or changing the timing of administration, or changing the frequency of the administration, or a combination thereof. In an aspect, altering one or more administering steps can comprise altering the administering of the complex comprising a targeting moiety and an oligonucleotide and altering the administering of a complex comprising a copolymer carrier and one or more oligonucleotides.

The term "contacting" as used herein refers to bringing a disclosed composition, compound, or complex together with an intended target (such as, e.g., a cell or population of cells, a receptor, an antigen, or other biological entity) in such a manner that the disclosed composition, compound, or complex can affect the activity of the intended target (e.g., receptor, transcription factor, cell, population of cells, etc.), either directly (i.e., by interacting with the target itself), or indirectly (i.e., by interacting with another molecule, cofactor, factor, or protein on which the activity of the target is dependent). In an aspect, a disclosed composition or complex can be contacted with a cell or population of cells, such as, for example, B-cells.

As used herein, the term "determining" can refer to measuring or ascertaining an activity or an event or a quantity or an amount or a change in expression and/or in activity level or in prevalence and/or incidence. For example, determining can refer to measuring or ascertaining the quantity or amount of apoptotic induction. Determining can also refer to measuring or ascertaining the quantity or amount of caspase activity or expression. Methods and techniques used to determining an activity or an event or a quantity or an amount or a change in expression and/or in activity level or in prevalence and/or incidence as used herein can refer to the steps that the skilled person would take to measure or ascertain some quantifiable value. The art is familiar with the ways to measure an activity or an event or a quantity or an amount or a change in expression and/or in activity level or in prevalence and/or incidence As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. For example, in an aspect, an effective amount of a disclosed composition or complex is the amount effective to induce apoptosis in a desired cell or population of cells. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a disclosed composition or complex at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. In an aspect, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

i) Copolymers

Traditional copolymers have been used in numerous laboratories worldwide and also in several clinical trials. (See U.S. Pat. No. 5,037,883, which is hereby incorporated by reference in its entirety). For example, N-(2-hydroxypropyl) methacrylamide) (HPMA) copolymers are: (1) biocompatible and have a well-established safety profile; (2) water-soluble and have favorable pharmacokinetics when compared to low molecular weight (free, non-attached) drugs; and (3) possess excellent chemistry flexibility (i.e., monomers containing different side chains can be easily synthesized and incorporated into their structure). However, HPMA polymers are not degradable and the molecular weight of HPMA polymers should be kept below the renal threshold to sustain biocompatibility. This limits the intravascular half-life and accumulation of HPMA polymers in solid tumor via the EPR (enhanced permeability and retention) effect.

To overcome these limitations, a backbone degradable HPMA copolymer carrier was developed. The copolymer carrier can contain enzymatically degradable sequences (i.e., by Cathepsin B, matrix matalloproteinases, etc.) in the main chain (i.e., the polymer backbone) and enzymatically degradable side chains (i.e., for drug release). (See, e.g., U.S. patent application Ser. No. 13/583,270, which is hereby incorporated by reference in its entirety). Upon reaching the lysosomal compartment of cells, the drug is released and concomitantly the polymer carrier is degraded into molecules that are below the renal threshold and can be eliminated from the subject. Thus, diblock or multiblock biodegradable copolymers with increased molecular weight can be produced. This can further enhance the blood circulation time of the Copolymer-MORF2 complexes disclosed herein, which is favorable for drug-free macromolecular therapeutics targeting, for example, circulating cancer cells (i.e., malignant B-cells). Furthermore, U.S. Pat. No. 4,062,831 describes a range of water-soluble polymers and U.S. Pat.

No. 5,037,883 describes a variety of peptide sequences, both of which are hereby incorporated by reference in their entireties.

ii) Morpholinos

The compositions and methods disclosed herein can utilize a biocompatible, synthetic oligonucleotide analogue with a chemically modified backbone. The schematic shown below lists several analogues and compares the properties of these analogues with natural DNA.

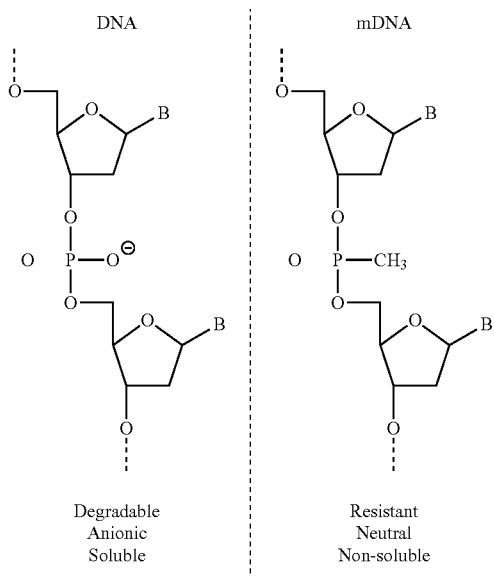

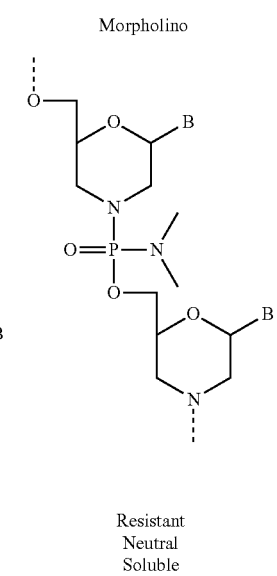

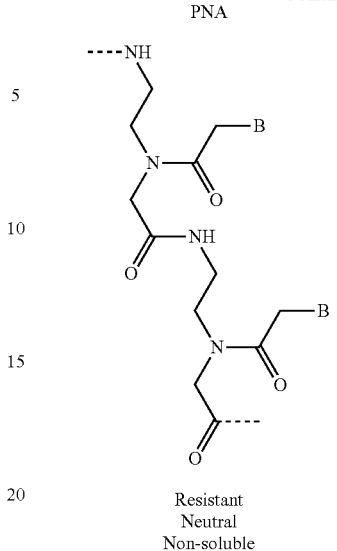

Based on these properties, the disclosed compositions and methods are not compatible with natural DNA or RNA. Rather, as the analogue must be biocompatible and non-degradable, the disclosed compositions and methods can utilize phosphorodiamidate morpholino oligonucleotides (also known as morpholinos or MORFs). Morpholinos have a chemically-modified, non-charged backbone and are assembled from four different subunits, each of which contains one of the four nucleobases (A, T, G, and C) linked to a 6-membered morpholine ring. The subunits are joined by non-ionic phosphordiamidate linkages to generate a morpholino oligonucleotide. Morpholinos also possess strong binding affinity (i.e., Kd from the low nM to pM levels), high sequence specificity, and well-demonstrated safety profiles. Furthermore, the immunogenicity of morpholinos is highly sequence dependent, and therefore, can be addressed. The synthesis, structures, and binding characteristics of morpholinos are detailed in U.S. Pat. Nos. 5,698,685, 5,217,866, 5,142,047, 5,034,506, 5,166,315, 5,521,063, and 5,506,337, each of which are incorporated herein by reference in its entirety.

A disclosed morpholino having a longer length provides a higher specificity and a stronger binding affinity; however, such morpholinos also have poorer water-solubility. In the art, a 14 bp-15 bp morpholino is considered the minimal length necessary to maintain ideal targeting effects. A 25 bp morpholino can ensure strong binding affinity and good water-solubility (about 5-30 mM). For example, using 25 bp morpholinos in the disclosed compositions and methods can avoid the impact of steric hindrance on the hybridization of MORF1 and MORF2. A longer sequence can provide better "steric flexibility" for hybridization. Accordingly, in the compositions and methods disclosed herein, morpholinos can comprise 10 bp-40 bp. In an aspect, for example, a morpholino can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length.

The A/T/C/G content of a disclosed morpholino can be determined based on three factors: (1) G+C content (# or % of G's and C's), (2) G content (# or % of G's), and (3) C content (# or % of C's).

Regarding G+C content, a disclosed morpholino can comprise a G+C content of about 35% to about 65%. This range can provide optimal binding efficacy and specificity. Regarding G content, a disclosed morpholino can comprise a G content of less than about 36%. This level of G content can provide good aqueous solubility; however, repeats of 4 or more G's should be avoided. Regarding C content, a disclosed morpholino can comprise a C content of less than 7. This level of C content can ensure that the unfavorable effect of enhancing kidney accumulation of a morpholino can be avoided. Furthermore, conjugation of one or more morpholinos with a copolymer can favorably alter the pharmacokinetic profiles of the morpholinos and can reduce kidney accumulation (as compared to conjugation of morpholinos and Fab' fragment). Table 1 shows the kidney accumulation of morpholinos comprising varying levels of C content. The morpholino having 25 C's had the highest percent accumulation in the kidneys of normal mice just 3 hours post-injection. (Liu et al., 2004).

TABLE 1

| Sequences of $^{99m}$Tc-labeled MORFs | SEQ ID NO. | # of C's | % ID/ Kidneys |
|---|---|---|---|
| 5' AAAAAAAAAAAAAAAAAAAAAAAAA 3' | SEQ ID NO. 53 | 0 | 0.9 |
| 5' TTTTTTTTTTTTTTTTTTTTTTTTT 3' | SEQ ID NO. 54 | 0 | 3.1 |
| 5' AAGAAGAAGAAGAAGAAGAAGAAGA 3' | SEQ ID NO. 55 | 0 | 2.8 |
| 5' TAGTTGTGACGTACA 3' | SEQ ID NO. 56 | 2 | 1.7 |
| 5' ATCAACACTGCTTGT 3' | SEQ ID NO. 57 | 4 | 4.5 |
| 5' ATCAACACTGCTTGTGGG 3' | SEQ ID NO. 58 | 4 | 4.7 |
| 5' ATCAACACTGCTTGTGGGTGGTGGT 3' | SEQ ID NO. 59 | 4 | 5.6 |
| 5' TAGTTGTGACGTACACCC 3' | SEQ ID NO. 60 | 5 | 4.9 |
| 5' TAGTTGTGACGTACACCCACCACCA 3' | SEQ ID NO. 61 | 9 | 13.5 |
| 5' CACCACCCCCCTCGCTGGTC 3' | SEQ ID NO. 62 | 11 | 20.9 |
| 5' CCCCCCCCCCCCCCCCCCCCCCCCC 3' | SEQ ID NO. 63 | 25 | 80.8 |

In the disclosed compositions and methods, a morpholino conjugated to the Fab' fragment can comprise more A's and less C's whereas the one or more morpholinos conjugated to the copolymer can comprise more C's and less A's. Accordingly, in an aspect, a 25 bp morpholino can comprise 3 C's, 6 G's, 12 A's, 4 T's (G+C=36%, G=24%). A complementary 25 bp morpholino can comprise 6 C's, 3 G's, 4 A's, 12 T's (G+C=36%, G=12%).

After the nucleobase composition of each morpholino is determined, a publically accessible, online sequence "scrambler" can be used to ensure minimal off-target binding with human mRNA. Furthermore, publically accessible, online sequence analysis software can be used to ensure minimal self-complementarity. In the experiments disclosed herein, when performing sequence analysis to avoid self-complementarity, the "Minimum base pairs required for self-dimerization" and "Minimum base pairs required for a hairpin" were set to "2" and "2" (for 10 bp and 12 bp); "3" and "3" (for 15 bp, 18 bp, 20 bp, 23 bp, and 25 bp); "4" and "4" (for 28 bp, 30 bp, 32 bp, and 35 bp); and "5" and "4" (for 38 bp and 40 bp). Table 2 provides a listing of exemplary morpholinos for use in the disclosed compositions and methods.

TABLE 2

Listing of Exemplary Morpholinos

| MORF # | | Length | Content | |
|---|---|---|---|---|
| (SEQ ID NO:) | MORF Sequences | (bp) | G + C | G |
| MORF1-a (SEQ ID NO: 1) | 5' GAA CTA ATG CAA TAA CTA TCA CGA ATG CGG GTA ACT TAA T 3' | 40 | 35% | 17.5% |

TABLE 2-continued

Listing of Exemplary Morpholinos

| MORF # (SEQ ID NO:) | MORF Sequences | Length (bp) | Content G + C | G |
|---|---|---|---|---|
| MORF2-a (SEQ ID NO: 2) | 5' ATT AAG TTA CCC GCA TTC GTG ATA GTT ATT GCA TTA GTT C 3' | 40 | 35% | 17.5% |
| MORF1-b (SEQ ID NO: 3) | 5' GAA ACC GCT ATT TAT TGG CTA AGA ACA GAT ACG AAT CAT A 3' | 40 | 35% | 17.5% |
| MORF2-b (SEQ ID NO: 4) | 5'-TAT GAT TCG TAT CTG TTC TTA GCC AAT AAA TAG CGG TTT C 3' | 40 | 35% | 17.5% |
| MORF1-c (SEQ ID NO: 5) | 5' GTA AAC GCG ACA AAT GCC GAT AAT GCT TCG ATA ATA AT 3' | 38 | 37% | 18.5% |
| MORF2-c (SEQ ID NO: 6) | 5' ATT ATT ATC GAA GCA TTA TCG GCA TTT GTC GCG TTT AC 3' | 38 | 37% | 18.5% |
| MORF1-d (SEQ ID NO: 7) | 5' GAC AGA GTT CAC TAT GAC AAA CGA TTT CAC GAG TAA TA 3' | 38 | 37% | 18.5% |
| MORF2-d (SEQ ID NO: 8) | 5' TAT TAC TCG TGA AAT CGT TTG TCA TAG TGA ACT CTG TC 3' | 38 | 37% | 18.5% |
| MORF1-e (SEQ ID NO: 9) | 5' CCT GAT ACA GAA GTA GAA AGC AGT CAC GCA ATA TA 3' | 35 | 40% | 20% |
| MORF2-e (SEQ ID NO: 10) | 5' TAT ATT GCG TGA CTG CTT TCT ACT TCT GTA TCA GG 3' | 35 | 40% | 20% |
| MORF1-f (SEQ ID NO: 11) | 5' GAA CAA CGA GAG GTG CTC AAT ACA GAT ATC AAT CA 3' | 35 | 40% | 20% |
| MORF2-f (SEQ ID NO: 12) | 5' TGA TTG ATA TCT GTA TTG AGC ACC TCT CGT TGT TC 3' | 35 | 40% | 20% |
| MORF1-g (SEQ ID NO: 13) | 5' AGT CAT AGA TAG ACA GAA TAG CCG GAT AAA CT 3' | 32 | 38% | 22% |
| MORF2-g (SEQ ID NO: 14) | 5' AGT TTA TCC GGC TAT TCT GTC TAT CTA TGA CT 3' | 32 | 38% | 16% |
| MORF1-h (SEQ ID NO: 15) | 5' GAT ACA GAA GTA GAA AGC AGT CAC GCA ATA TA 3' | 32 | 38% | 22% |
| MORF2-h (SEQ ID NO: 16) | 5' TAT ATT GCG TGA CTG CTT TCT ACT TCT GTA TC 3' | 32 | 38% | 16% |
| MORF1-i (SEQ ID NO: 17) | 5' GGC ATA GAT AAC AGA ATA GCC GGA TAA ACT 3' | 30 | 40% | 23% |
| MORF2-i (SEQ ID NO: 18) | 5' AGT TTA TCC GGC TAT TCT GTT ATC TAT GCC 3' | 30 | 40% | 17% |
| MORF1-j (SEQ ID NO: 19) | 5' GAC CAG TAG ATA AGT GAA CCA GAT TGA ACA 3' | 30 | 40% | 23% |
| MORF2-j (SEQ ID NO: 20) | 5' TGT TCA ATC TGG TTC ACT TAT CTA CTG GTC 3' | 30 | 40% | 17% |
| MORF1-k (SEQ ID NO: 21) | 5' GAG TAC AGC CAG AGA GAG AAT CAA TAT A 3' | 28 | 39% | 25% |
| MORF2-k (SEQ ID NO: 22) | 5' TAT ATT GAT TCT CTC TCT GGC TGT ACT C 3' | 28 | 39% | 14% |
| MORF1-l (SEQ ID NO: 23) | 5' GTG AAC ACG AAA GAG TGA CGC AAT AAA T 3' | 28 | 39% | 25% |
| MORF2-l (SEQ ID NO: 24) | 5' ATT TAT TGC GTC ACT CTT TCG TGT TCA C 3' | 28 | 39% | 14% |
| MORF1-m (SEQ ID NO: 25) | 5' GAG TAA GCC AAG GAG AAT CAA TAT A 3' | 25 | 36% | 24% |

TABLE 2-continued

Listing of Exemplary Morpholinos

| MORF # (SEQ ID NO:) | MORF Sequences | Length (bp) | G + C | G |
|---|---|---|---|---|
| MORF2-m (SEQ ID NO: 26) | 5' TAT ATT GAT TCT CCT TGG CTT ACT C 3' | 25 | 36% | 12% |
| MORF1-n (SEQ ID NO: 27) | 5' AGA TGA CGA TAA AGA CGC AAA GAT T 3' | 25 | 36% | 24% |
| MORF2-n (SEQ ID NO: 28) | 5' AAT CTT TGC GTC TTT ATC GTC ATC T 3' | 25 | 36% | 12% |
| MORF1-o (SEQ ID NO: 29) | 5' GGA CCA AGT AAA CAG GGA TAT AT 3' | 23 | 39% | 26% |
| MORF2-o (SEQ ID NO: 30) | 5' ATA TAT CCC TGT TTA CTT GGT CC 3' | 23 | 39% | 13% |
| MORF1-p (SEQ ID NO: 31) | 5' GCT GAA AAC CAA TAT GAG AGT GA 3' | 23 | 39% | 26% |
| MORF2-p (SEQ ID NO: 32) | 5' TCA CTC TCA TAT TGG TTT TCA GC 3' | 23 | 39% | 13% |
| MORF1-q (SEQ ID NO: 33) | 5' GAT GAA GTA CCG ACA AGA TA 3' | 20 | 40% | 25% |
| MORF2-q (SEQ ID NO: 34) | 5' TAT CTT GTC GGT ACT TCA TC 3' | 20 | 40% | 15% |
| MORF1-r (SEQ ID NO: 35) | 5' GAC AGG ATG AAT AAC ACA GT 3' | 20 | 40% | 25% |
| MORF2-r (SEQ ID NO: 36) | 5' ACT GTG TTA TTC ATC CTG TC 3' | 20 | 40% | 15% |
| MORF1-s (SEQ ID NO: 37) | 5' GCA GCA AAC GAA GTA TAT 3' | 18 | 39% | 22% |
| MORF2-s (SEQ ID NO: 38) | 5' ATA TAC TTC GTT TGC TGC 3' | 18 | 39% | 17% |
| MORF1-t (SEQ ID NO: 39) | 5' GTC ATA ACA GAA CAG GTA 3' | 18 | 39% | 22% |
| MORF2-t (SEQ ID NO: 40) | 5' TAC CTG TTC TGT TAT GAC 3' | 18 | 39% | 17% |
| MORF1-u (SEQ ID NO: 41) | 5' TCA AGA CAG AAG GAT 3' | 15 | 40% | 27% |
| MORF2-u (SEQ ID NO: 42) | 5' ATC CTT CTG TCT TGA 3' | 15 | 40% | 13% |
| MORF1-v (SEQ ID NO: 43) | 5' TAG CAA CAT AGG AAG 3' | 15 | 40% | 27% |
| MORF2-v (SEQ ID NO: 44) | 5' CTT CCT ATG TTG CTA 3' | 15 | 40% | 13% |
| MORF1-w (SEQ ID NO: 45) | 5' CAG AGA GCA TAT 3' | 12 | 42% | 25% |
| MORF2-w (SEQ ID NO: 46) | 5' ATA TGC TCT CTG 3' | 12 | 42% | 17% |
| MORF1-x (SEQ ID NO: 47) | 5' CAA GAG GTA CAT 3' | 12 | 42% | 25% |
| MORF2-x (SEQ ID NO: 48) | 5' ATG TAC CTC TTG 3' | 12 | 42% | 17% |
| MORF1-y (SEQ ID NO: 49) | 5' AAG AGG TAC A 3' | 10 | 40% | 30% |

TABLE 2-continued

Listing of Exemplary Morpholinos

| MORF # (SEQ ID NO:) | MORF Sequences | Length (bp) | Content G + C | G |
|---|---|---|---|---|
| MORF2-y (SEQ ID NO: 50) | 5' TGT ACC TCT T 3' | 10 | 40% | 10% |
| MORF1-z (SEQ ID NO: 51) | 5' AAG GAC AGT A 3' | 10 | 40% | 30% |
| MORF2-z (SEQ ID NO: 52) | 5' TAC TGT CCT T 3' | 10 | 40% | 10% |

In an aspect, hybridization between a pair of disclosed morpholinos can be achieved by base-pairing (i.e., specific hydrogen bonding patterns). The hybridization can be maintained by base-stacking (i.e., pi interactions). It is noted that the hybridization between a pair of disclosed morpholinos is more specific that the formation of coiled-coil peptides.

In an aspect, the morpholinos utilized in the disclosed compositions and methods can be completely complementary (100%) or can be less than completely complementary. Therefore, in an aspect, the percent complementarity of the morpholino of the Fab'-MORF1 complex and the one or more morpholinos of the Copolymer-MORF2 complex can be 80-85%, 85-90%, 90-95%, or 95-100% complementary. In an aspect, the morpholino of the Fab'-MORF1 complex and the one or more morpholinos of the Copolymer-MORF2 complex can be 93%, 94%, 95%, 96%, 97%, 98%, 99%, or 100% complementary. In an aspect, the morpholino of the Fab'-MORF1 complex and the one or more morpholinos of the Copolymer-MORF2 complex can be at least 93% complementary.

In an aspect, the morpholino of the Fab'-MORF1 complex and the one or more morpholinos of the Copolymer-MORF2 complex can have an equilibrium dissociation constant $Kd \leq 15$ μM. In an aspect, the morpholino of the Fab'-MORF1 complex and the one or more morpholinos of the Copolymer-MORF2 complex can have a binding constant (Kd) smaller than $10^{-7}$ M. In an aspect, the morpholino of the Fab'-MORF1 complex and the one or more morpholinos of the Copolymer-MORF2 complex can have a binding constant (Kd) smaller than $10^{-9}$ M.

B. COMPOSITIONS i) Complex Comprising Targeting Moiety and Oligonucleotide

Disclosed herein are complexes comprising a targeting moiety and an oligonucleotide. In an aspect, a disclosed complex comprises a detectable label. Detectable labels are known to one of skill in the art and include, but are not limited to: rhodamine, FITC, Cy3, Cy3.5, Cy5, Texas Red, Alexa Fluor 488, Alexa Fluor 610, Alexa Fluor 647, and Alexa Fluor 750.

In an aspect of a disclosed complex, a targeting moiety can be specific for a non-internalizing cell surface molecule or slowly internalizing cell surface molecule. Examples of a non-internalizing cell surface molecule or a slowly internalizing cell surface molecule are known to one of skill in the art. In an aspect, a non-internalizing cell surface molecule or slowly internalizing cell surface molecule can be on a cell or a population of cells. In an aspect, a cell or a population of cells can be B-cells. In an aspect, the B-cells can be normal B-cells. In an aspect, the B-cells can be malignant B-cells.

In an aspect of a disclosed complex, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect of a disclosed complex, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamer. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

Oligonucleotides are well known to the art. In an aspect of a disclosed complex, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed complex, an oligonucleotide can be a peptide nucleic acid. In an aspect, an oligonucleotide can be a morpholino. In an aspect, a disclosed morpholino does not bind to any mRNA target of a genome, such as, for example, the human genome. In an aspect, a disclosed morpholino is not self-complementary. In an aspect, a morpholino can be succinimidyl-4-(N-maleimidomethyl)cyclohexane-1-carboxylate (SMCC) modified.

In an aspect of a disclosed complex, a morpholino comprises 10 bp-40 bp. For example, a morpholino can be 10 bp in length, 11 bp in length, 12 bp in length, 13 bp in length, 14 bp in length, 15 bp in length, 16 bp in length, 17 bp in length, 18 bp in length, 19 bp in length, 20 bp in length, 21 bp in length, 22 bp in length, 23 bp in length, 24 bp in length, 25 bp in length, 26 bp in length, 27 bp in length, 28 bp in length, 29 bp in length, 30 bp in length, 31 by in length, 32 bp in length, 33 bp in length, 34 bp in length, 35 bp in length, 36 bp in length, 37 bp in length, 38 bp in length, 39 bp in length, or 40 bp in length.

In an aspect, a morpholino can be 5' GAA CTA ATG CAA TAA CTA TCA CGA ATG CGG GTA ACT AAA T 3' (SEQ ID NO:1). In an aspect, a morpholino can be 5' ATT AAG TTA CCC GCA TTC GTG ATA GTT ATT GCA TTA GTT C 3' (SEQ ID NO:2). In an aspect, a morpholino can be GAA ACC GCT ATT TAT GGC TAA GAA ACA GAT ACG AAT CAT A 3' (SEQ ID NO:3). In an aspect, a morpholino can be 5' TAT GAT TCG TAT CTG TTC TTA GCC AAT AAA TAG CGG TTT C 3' (SEQ ID NO:4). In an aspect, a morpholino can be 5' GTA AAC GCG ACA AAT GCC GAT AAT GCT TCG ATA ATA AT 3' (SEQ ID NO:5). In an aspect, a morpholino can be 5' ATT ATT ATC GAA GCA TTA TCG GCA TTT GTC GCG TTT AC 3' (SEQ ID NO:6). In an aspect, a morpholino can be 5' GAC AGA GTT CAC TAT GAC AAA CGA TTT CAC GAG TAA TA 3' (SEQ ID NO:7). In an aspect, a morpholino can be 5' TAT TAC TCG TGA AAT CGT TTG TCA TAG TGA ACT CTG TC 3' (SEQ ID NO:8). In an aspect, a morpholino can be 5' CCT GAT ACA GAA GTA GAA AGC AGT CAC GCA ATA TA 3' (SEQ ID NO:9). In an aspect, a morpholino can be 5' TAT ATT GCG TGA CTG CTT TCT ACT TCT GTA TCA GG 3' (SEQ ID NO:10). In an aspect, a morpholino can be 5' GAA CAA CGA GAG GTG CTC AAT ACA GAT ATC AAT CA 3' (SEQ ID NO:11). In an aspect, a morpholino can be 5' TGA TTG ATA TCT GTA TTG AGC ACC TCT CGT TGT TC 3' (SEQ ID NO:12). In an aspect, a morpholino can be 5' AGT CAT AGA TAG ACA GAA TAG CCG GAT AAA CT 3' (SEQ ID NO:13). In an aspect, a morpholino can be 5' AGT TTA TCC GGC TAT TCT GTC TAT CTA TGA CT 3' (SEQ ID NO:14). In an aspect, a morpholino can be 5' GAT ACA GAA GTA GAA AGC AGT CAC GCA ATA TA 3' (SEQ ID NO:15). In an aspect, a morpholino can be 5' TAT ATT GCG TGA CTG CTT TCT ACT TCT GTA TC 3' (SEQ ID NO:16). In an aspect, a morpholino can be 5' GGC ATA GAT AAC AGA ATA GCC GGA TAA ACT 3' (SEQ ID NO:17). In an aspect, a morpholino can be 5' AGT TTA TCC GGC TAT TCT GTT ATC TAT GCC 3' (SEQ ID NO:18). In an aspect, a morpholino can be 5' GAC CAG TAG ATA AGT GAA CCA GAT TGA ACA 3' (SEQ ID NO:19). In an aspect, a morpholino can be 5' TGT TCA ATC TGG TTC ACT TAT CTA CTG GTC 3' (SEQ ID NO:20). In an aspect, a morpholino can be 5' GAG TAC AGC CAG AGA GAG AAT CAA TAT A 3' (SEQ ID NO:21). In an aspect, a morpholino can be 5' TAT ATT GAT TCT CTC TCT GGC TGT ACT C 3' (SEQ ID NO:22). In an aspect, a morpholino can be 5' GTG AAC ACG AAA GAG TGA CGC AAT AAA T 3' (SEQ ID NO:23). In an aspect, a morpholino can be 5' ATT TAT TGC GTC ACT CTT TCG TGT TCA C 3' (SEQ ID NO:24). In an aspect, a morpholino can be 5' GAG TAA GCC AAG GAG AAT CAA TAT A 3' (SEQ ID NO:25). In an aspect, a morpholino can be 5' TAT ATT GAT TCT CCT TGG CTT ACT C 3' (SEQ ID NO:26). In an aspect, a morpholino can be 5' AGA TGA CGA TAA AGA CGC AAA GAT T 3' (SEQ ID NO:27). In an aspect, a morpholino can be 5' AAT CTT TGC GTC TTT ATC GTC ATC T 3' (SEQ ID NO:28). In an aspect, a morpholino can be 5' GGA CCA AGT AAA CAG GGA TAT AT 3' (SEQ ID NO:29). In an aspect, a morpholino can be 5' ATA TAT CCC TGT TTA CTT GGT CC 3' (SEQ ID NO:30). In an aspect, a morpholino can be 5' GCT GAA AAC CAA TAT GAG AGT GA 3' (SEQ ID NO:31). In an aspect, a morpholino can be 5' TCA CTC TCA TAT TGG TTT TCA GC 3' (SEQ ID NO:32). In an aspect, a morpholino can be 5' GAT GAA GTA CCG ACA AGA TA 3' (SEQ ID NO:33). In an aspect, a morpholino can be 5' TAT CTT GTC GGT ACT TCA TC 3' (SEQ ID NO:34). In an aspect, a morpholino can be 5' GAC AGG ATG AAT AAC ACA GT 3' (SEQ ID NO:35). In an aspect, a morpholino can be 5' ACT GTG TTA TTC ATC CTG TC 3' (SEQ ID NO:36). In an aspect, a morpholino can be 5' GCA GCA AAC GAA GTA TAT 3' (SEQ ID NO:37). In an aspect, a morpholino can be 5' ATA TAC TTC GTT TGC TGC 3' (SEQ ID NO:38). In an aspect, a morpholino can be 5' GTC ATA ACA GAA CAG GTA 3' (SEQ ID NO:39). In an aspect, a morpholino can be 5' TAC CTG TTC TGT TAT GAC 3' (SEQ ID NO:40). In an aspect, a morpholino can be 5' TCA AGA CAG AAG GAT 3' (SEQ ID NO:41). In an aspect, a morpholino can be 5' ATC CTT CTG TCT TGA 3' (SEQ ID NO:42). In an aspect, a morpholino can be 5' TAG CAA CAT AGG AAG 3' (SEQ ID NO:43). In an aspect, a morpholino can be 5' CTT CCT ATG TTG CTA 3' (SEQ ID NO:44). In an aspect, a morpholino can be 5' CAG AGA GCA TAT 3' (SEQ ID NO:45). In an aspect, a morpholino can be 5' ATA TGC TCT CTG 3' (SEQ ID NO:46). In an aspect, a morpholino can be 5' CAA GAG GTA CAT 3' (SEQ ID NO:47). In an aspect, a morpholino can be 5' ATG TAC CTC TTG 3' (SEQ ID NO:48). In an aspect, a morpholino can be 5' AAG AGG TAC A 3' (SEQ ID NO:49). In an aspect, a morpholino can be 5' TGT ACC TCT T 3' (SEQ ID NO:50). In an aspect, a morpholino can be 5' AAG GAC AGT A 3' (SEQ ID NO:51). In an aspect, a morpholino can be 5' TAC TGT CCT T 3' (SEQ ID NO:52).

In an aspect of a disclosed complex, a morpholino can be 25 bp in length and can comprise 3 cytidines, 6 guanosines, 12 adenosines, and 4 thymidines. For example, in an aspect, a morpholino comprising 3 cytidines, 6 guanosines, 12 adenosines, and 4 thymidines can be 5' GAGTAAGCCAAGGAGAATCAATATA 3' (SEQ ID NO:25). In an aspect, a morpholino of a disclosed complex can comprise about 35% to about 65% GC content. In an aspect, a morpholino can comprise a G content less than 36%. In an aspect, a morpholino can comprise no more than 7 C's.

In an aspect of a disclosed complex, a targeting moiety can be conjugated to an oligonucleotide. Types of conjugation and methods for conjugating are known to the art. In an aspect, a targeting moiety of a disclosed complex can be conjugated to an oligonucleotide via, for example, a covalent bond. In an aspect, a targeting moiety can be conjugated to an oligonucleotide via a thiol group. Thiol groups are known to the art. In an aspect of a disclosed complex, a targeting moiety can be conjugated to an oligonucleotide via a thioether bond, a thiol-maleimide bond, a thiol-vinylsulfone bond, a thiol-halogeno bond, a thiol-pentafluorophenyl ester bond, a thiol-ene bond, or a thiol-yne bond.

Disclosed herein are complexes comprising a targeting moiety and an oligonucleotide, wherein the targeting moiety is a Fab' fragment, wherein the Fab' fragment is specific for a CD20 receptor, wherein the oligonucleotide is a morpholino, and wherein the Fab' fragment is conjugated to the morpholino via a thioether bond.

ii) Complex Comprising a Copolymer Carrier and One or More Oligonucleotides

Disclosed herein are complexes comprising a copolymer carrier and one or more oligonucleotides. In an aspect, a disclosed complex comprises a detectable label. Detectable labels are known to the art and include, but are not limited to: rhodamine, FITC, Cy3, Cy3.5, Cy5, Texas Red, Alexa Fluor 488, Alexa Fluor 610, Alexa Fluor 647, and Alexa Fluor 750.

In an aspect of the disclosed complexes, a copolymer carrier can be water-soluble. In an aspect of a disclosed copolymer, a copolymer carrier can comprise a main chain and one or more side chains. In an aspect, a main chain carrier can comprise enzymatically degradable sequences. In an aspect, one or more side chains of a can comprise enzymatically degradable sequences. In an aspect, one or more side chains can terminate in a functional group. Functional groups are known to the art and include, but are not limited to: an amine reactive active ester, a maleimide, an azide, and an alkyne. In an aspect, a functional group can permit the binding of one or more oligonucleotides to one or more side chains of a disclosed copolymer complex. In an aspect, one or more side chains can be conjugated to one or more oligonucleotides via a disclosed functional group. In an aspect, a main chain can comprise N-(2-hydroxypropyl) methylacrylamide (HPMA) copolymerized with N-methacryloylglycylglycine-thiazolidine-2-thione (MA-GG-TT) monomers. In an aspect, a main chain can comprise N-(2-hydroxypropyl)methylacrylamide (HPMA) copolymerized with N-methacryloylglycylglycine-p-nitrophenyl ester (MA-GG-ONp) monomers.

Oligonucleotides are well known to the art. In an aspect of a disclosed complex, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed complex, one or more oligonucleotides can be peptide nucleic acids. In an aspect, one or more oligonucleotides can be morpholinos. In an aspect, the disclosed one or more morpholinos do not bind to any mRNA target of a genome, such as, for example, the human genome. In an aspect, the disclosed one or more morpholinos are not self-complementary. In an aspect, one or more morpholinos can be amine-derivatized. Derivatization, which typically involves the addition of a nucleophile as a functional group, and which includes amine derivatization and thiol derivatization, is known to the art. In an aspect, the disclosed one or more morpholinos can be generated through the use of an amine-pentafluorophenyl ester, an amine-succinimidoxy ester, or an amine-carboxyl. In an aspect, one or more morpholinos can be thiol-derivatized. In an aspect, the disclosed one or more morpholino can be generated through the use of thiol-maleimide.

In an aspect, a disclosed copolymer can comprise one or more grafted morpholinos. In an aspect, one or more morpholinos can comprise 1 morpholino, or 2 morpholinos, or 3 morpholinos, or 4 morpholinos, or 5 morpholinos, or 6 morpholinos, or 7 morpholinos, or 8 morpholinos, or 9 morpholinos, or 10 morpholinos. For example, in an aspect, a disclosed copolymer can comprise 1 morpholino. In an aspect, a disclosed copolymer can comprise 3 morpholinos. In an aspect, a disclosed copolymer can comprise 10 morpholinos. In an aspect, a disclosed copolymer can comprise more than 10 grafted morpholinos. In an aspect, the one or more morpholinos can comprise one or more grafted MORF2 morpholinos. For example, a disclosed copolymer-MORF2 complex can comprise 1 grafted morpholino. In an aspect, a disclosed copolymer-MORF2 complex can comprise 3 grafted morpholinos. In an aspect, a disclosed copolymer-MORF2 complex can comprise 10 grafted morpholinos. In an aspect, a disclosed copolymer-MORF2 complex can comprise more than 10 grafted morpholinos. In an aspect, the one or more oligonucleotides can comprise the same oligonucleotides or can comprise differing oligonucleotides. In an aspect, the one or more morpholinos can comprise the same morpholinos or can comprise differing morpholinos. In an aspect, the one or more morpholinos or grafted morpholinos can have the same sequence. In an aspect, the one or more morpholinos can have different sequence. For example, in an aspect multiple morpholinos can be present, wherein the one or more morpholinos comprise different sequences or wherein the one or more morpholinos comprise the same sequence or a combination thereof.

In an aspect of a disclosed complex, one or more morpholinos can comprise about 35% to about 65% GC content. In an aspect, one or more morpholinos can comprise a G content less than 36%. In an aspect, one or more morpholinos can comprise no more than 7 C's.

In an aspect of a disclosed complex, one or more morpholinos comprises 10 bp-40 bp. For example, a morpholino can be 10 bp in length, 11 bp in length, 12 bp in length, 13 bp in length, 14 bp in length, 15 bp in length, 16 bp in length, 17 bp in length, 18 bp in length, 19 bp in length, 20 bp in length, 21 bp in length, 22 bp in length, 23 bp in length, 24 bp in length, 25 bp in length, 26 bp in length, 27 bp in length, 28 bp in length, 29 bp in length, 30 bp in length, 31 bp in length, 32 bp in length, 33 bp in length, 34 bp in length, 35 bp in length, 36 bp in length, 37 bp in length, 38 bp in length, 39 bp in length, or 40 bp in length.

In an aspect, one or more morpholinos can be 5' GAA CTA ATG CAA TAA CTA TCA CGA ATG CGG GTA ACT TAA T 3' (SEQ ID NO:1). In an aspect, one or more morpholinos can be 5' ATT AAG TTA CCC GCA TTC GTG ATA GTT ATT GCA TTA GTT C 3' (SEQ ID NO:2). In an aspect, one or more morpholinos can be GAA ACC GCT ATT TAT TGG CTA AGA ACA GAT ACG AAT CAT A 3' (SEQ ID NO:3). In an aspect, one or more morpholinos can be 5' TAT GAT TCG TAT CTG TTC TTA GCC AAT AAA TAG CGG TTT C 3' (SEQ ID NO:4). In an aspect, one or more morpholinos can be 5' GTA AAC GCG ACA AAT GCC GAT AAT GCT TCG ATA ATA AT 3' (SEQ ID NO:5). In an aspect, one or more morpholinos can be 5' ATT ATT ATC GAA GCA TTA TCG GCA TTT GTC GCG TTT AC 3' (SEQ ID NO:6). In an aspect, one or more morpholinos can be 5' GAC AGA GTT CAC TAT GAC AAA CGA TTT CAC GAG TAA TA 3' (SEQ ID NO:7). In an aspect, one or more morpholinos can be 5' TAT TAC TCG TGA AAT CGT TTG TCA TAG TGA ACT CTG TC 3' (SEQ ID NO:8). In an aspect, one or more morpholinos can be 5' CCT GAT ACA GAA GTA GAA AGC AGT CAC GCA ATA TA 3' (SEQ ID NO:9). In an aspect, one or more morpholinos can be 5' TAT ATT GCG TGA CTG CTT TCT ACT TCT GTA TCA GG 3' (SEQ ID NO:10). In an aspect, one or more morpholinos can be 5' GAA CAA CGA GAG GTG CTC AAT ACA GAT ATC AAT CA 3' (SEQ ID NO:11). In an aspect, one or more morpholinos can be 5' TGA TTG ATA TCT GTA TTG AGC ACC TCT CGT TGT TC 3' (SEQ ID NO:12). In an aspect, one or more morpholinos can be 5' AGT CAT AGA TAG ACA GAA TAG CCG GAT AAA CT 3' (SEQ ID NO:13). In an aspect, one or more morpholinos can be 5' AGT TTA TCC GGC TAT TCT GTC TAT CTA TGA CT 3' (SEQ ID NO:14). In an aspect, one or more morpholinos can be 5' GAT ACA GAA GTA GAA AGC AGT CAC GCA ATA TA 3' (SEQ ID NO:15). In an aspect, one or more morpholinos can be 5' TAT ATT GCG TGA CTG CTT TCT ACT TCT GTA TC 3' (SEQ ID NO:16). In an aspect, one or more morpholinos can be 5' GGC ATA GAT AAC AGA ATA GCC GGA TAA ACT 3' (SEQ ID NO:17). In an aspect, one or more morpholinos can be 5' AGT TTA TCC GGC TAT TCT GTT ATC TAT GCC 3' (SEQ ID NO:18). In an aspect, one or more morpholinos can be 5' GAC CAG TAG ATA AGT GAA CCA GAT TGA ACA 3' (SEQ ID NO:19). In an aspect, one or more morpholinos can be 5' TGT TCA ATC TGG TTC ACT TAT CTA CTG GTC 3' (SEQ ID NO:20). In an aspect, one or more morpholinos can be 5' GAG TAC AGC CAG AGA GAG AAT CAA TAT A 3' (SEQ ID NO:21). In an aspect, one or more morpholinos can be 5' TAT ATT GAT TCT CTC TCT GGC TGT ACT C 3' (SEQ ID NO:22). In an aspect, one or more morpholinos can be 5' GTG AAC ACG AAA GAG TGA CGC AAT AAA T 3' (SEQ ID NO:23). In an aspect, one or more morpholinos can be 5' ATT TAT TGC GTC ACT CTT TCG TGT TCA C 3' (SEQ ID NO:24). In an aspect, one or more morpholinos can be 5' GAG TAA GCC AAG GAG AAT CAA TAT A 3' (SEQ ID NO:25). In an aspect, one or more morpholinos can be 5' TAT ATT GAT TCT CCT TGG CTT ACT C 3' (SEQ ID NO:26). In an aspect, one or more morpholinos can be 5' AGA TGA CGA TAA AGA CGC AAA GAT T 3' (SEQ ID NO:27). In an aspect, one or more morpholinos can be 5' AAT CTT TGC GTC TTT ATC GTC ATC T 3' (SEQ ID NO:28). In an aspect, one or more morpholinos can be 5' GGA CCA AGT AAA CAG GGA TAT AT 3' (SEQ ID NO:29). In an aspect, one or more morpholinos can be 5' ATA TAT CCC TGT TTA CTT GGT CC 3' (SEQ ID NO:30). In an aspect, one or more morpholinos can be 5' GCT GAA AAC CAA TAT GAG AGT GA 3' (SEQ ID NO:31). In an aspect, one or more morpholinos can be 5' TCA CTC TCA TAT TGG TTT TCA GC 3' (SEQ ID NO:32). In an aspect, one or more morpholinos can be 5' GAT GAA GTA CCG ACA AGA TA 3' (SEQ ID NO:33). In an aspect, one or more morpholinos can be 5' TAT CTT GTC GGT ACT TCA TC 3' (SEQ ID NO:34). In an aspect, one or more morpholinos can be 5' GAC AGG ATG AAT AAC ACA GT 3' (SEQ ID NO:35). In an aspect, one or more morpholinos can be 5' ACT GTG TTA TTC ATC CTG TC 3' (SEQ ID NO:36). In an aspect, one or more morpholinos can be 5' GCA GCA AAC GAA GTA TAT 3' (SEQ ID NO:37). In an aspect, one or more morpholinos can be 5' ATA TAC TTC GTT TGC TGC 3' (SEQ ID NO:38). In an aspect, one or more morpholinos can be 5' GTC ATA ACA GAA CAG GTA 3' (SEQ ID NO:39). In an aspect, one or more morpholinos can be 5' TAC CTG TTC TGT TAT GAC 3' (SEQ ID NO:40). In an aspect, one or more morpholinos can be 5' TCA AGA CAG AAG GAT 3' (SEQ ID NO:41). In an aspect, one or more morpholinos can be 5' ATC CTT CTG TCT TGA 3' (SEQ ID NO:42). In an aspect, one or more morpholinos can be 5' TAG CAA CAT AGG AAG 3' (SEQ ID NO:43). In an aspect, one or more morpholinos can be 5' CTT CCT ATG TTG CTA 3' (SEQ ID NO:44). In an aspect, one or more morpholinos can be 5' CAG AGA GCA TAT 3' (SEQ ID NO:45). In an aspect, one or more morpholinos can be 5' ATA TGC TCT CTG 3' (SEQ ID NO:46). In an aspect, one or more morpholinos can be 5' CAA GAG GTA CAT 3' (SEQ ID NO:47). In an aspect, one or more morpholinos can be 5' ATG TAC CTC TTG 3' (SEQ ID NO:48). In an aspect, one or more morpholinos can be 5' AAG AGG TAC A 3' (SEQ ID NO:49). In an aspect, one or more morpholinos can be 5' TGT ACC TCT T 3' (SEQ ID NO:50). In an aspect, one or more morpholinos can be 5' AAG GAC AGT A 3' (SEQ ID NO:51). In an aspect, one or more morpholinos can be 5' TAC TGT CCT T 3' (SEQ ID NO:52).

In an aspect, one or more morpholinos of a disclosed complex can be 25 bp in length and can comprise 6 cytidines, 3 guanosines, 4 adenosines, and 12 thymidines. For example, in an aspect, the one or more morpholinos comprising 6 cytidines, 3 guanosines, 4 adenosines, and 12 thymidines can be 5' TATATTGATTCTCCTTGGCTTACTC 3' (SEQ ID NO:26).

Disclosed herein is a complex comprising a copolymer carrier and one or more oligonucleotides, wherein the copolymer carrier comprises a main chain and one or more side chains, wherein the copolymer carrier comprises N-(2-hydroxypropyl)methylacrylamide (HPMA) copolymerized with N-methacryloylglycylglycine-thiazolidine-2-thione (MA-GG-TT) monomers, wherein the one or more side chains can be conjugated to one or more oligonucleotides, wherein the one or more oligonucleotides are morpholinos.

iii) Kits

Disclosed herein are kits comprising a first complex comprising a targeting moiety and an oligonucleotide, and a second complex comprising a copolymer carrier and one or more oligonucleotides. In an aspect, a disclosed kit can comprise instructions for administering a first complex comprising a targeting moiety and an oligonucleotide and a second complex comprising a copolymer carrier and one or more oligonucleotides.

Disclosed herein are kits comprising a first complex comprising a targeting moiety and an oligonucleotide, a second complex comprising a copolymer carrier and one or more oligonucleotides, and instructions for administering the first complex and the second complex.

In an aspect, the first complex and the second complex are co-formulated. In an aspect, the first complex and the second complex are co-packaged.

In an aspect of a disclosed kit, a targeting moiety can be specific for a non-internalizing cell surface molecule or slowly internalizing cell surface molecule. Examples of a non-internalizing cell surface molecule or a slowly internalizing cell surface molecule are known to the art. In an aspect, a non-internalizing cell surface molecule or slowly internalizing cell surface molecule can be on a cell or a population of cells. In an aspect, a cell or a population of cells can be B-cells. In an aspect, the B-cells can be normal B-cells. In an aspect, the B-cells can be malignant B-cells.

In an aspect of a disclosed kit, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect, a targeting moiety of a disclosed kit can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamer. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

In an aspect of a disclosed kit, a copolymer carrier can be water-soluble. In an aspect, a disclosed copolymer carrier can comprise a main chain and one or more side chains. In an aspect, a main chain of a copolymer carrier can comprise enzymatically degradable sequences. In an aspect, one or more side chains of a copolymer carrier can comprise enzymatically degradable sequences. In an aspect, one or more side chains of a copolymer carrier can terminate in a functional group. Functional groups are known to the art and include, but are not limited to: an amine reactive active ester, a maleimide, an azide, a disulfide, and an alkyne. In an aspect, a functional group can permit the binding of one or more oligonucleotides to one or more side chains of a copolymer complex. In an aspect, one or more side chains can be conjugated to one or more oligonucleotides via a functional group. In an aspect, a main chain of a disclosed copolymer carrier can comprise N-(2-hydroxypropyl)methylacrylamide (HPMA) copolymerized with N-methacryloylglycylglycine-thiazolidine-2-thione (MA-GG-TT) monomers. In an aspect, a main chain of a copolymer carrier can comprise N-(2-hydroxypropyl)methylacrylamide (HPMA) copolymerized with N-methacryloylglycylglycine-p-nitrophenyl ester (MA-GG-ONp) monomers.

Oligonucleotides are well known to the art. In an aspect, an oligonucleotide can be biocompatible. In an aspect, an oligonucleotide of a disclosed kit can be non-degradable. In an aspect, an oligonucleotide of can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed kit, an oligonucleotide can be a peptide nucleic acid. In an aspect, a disclosed oligonucleotide can be a morpholino. In an aspect, a disclosed morpholino does not bind to any mRNA target of a genome, such as, for example, the human genome. In an aspect, a disclosed morpholino is not self-complementary. In an aspect of a disclosed kit, the morpholino of the first complex and the one or more morpholinos of the second complex can be complementary. In an aspect, the morpholino of the first complex is not self-complementary. In an aspect, the one or more morpholinos of the second complex are not self-complementary. In an aspect, the morpholino of the first complex and the one or more morpholinos of the second complex can have a Kd smaller than $10^{-7}$ M. In an aspect, the morpholino of the first complex and the one or more morpholinos of the second complex can have a Kd smaller than $10^{-9}$ M.

In an aspect, a copolymer of a disclosed kit can comprise one or more grafted morpholinos. In an aspect, one or more morpholinos can comprise 1 morpholino, or 2 morpholinos, or 3 morpholinos, or 4 morpholinos, or 5 morpholinos, or 6 morpholinos, or 7 morpholinos, or 8 morpholinos, or 9 morpholinos, or 10 morpholinos. For example, in an aspect, a disclosed copolymer can comprise 1 morpholino. In an aspect, a disclosed copolymer can comprise 3 morpholinos. In an aspect, a disclosed copolymer can comprise 10 morpholinos. In an aspect, a disclosed copolymer can comprise more than 10 grafted morpholinos. In an aspect, the one or more morpholinos can comprise one or more grafted MORF2 morpholinos. For example, a disclosed copolymer-MORF2 complex can comprise 1 grafted morpholino. In an aspect, a disclosed copolymer-MORF2 complex can comprise 3 grafted morpholinos. In an aspect, a disclosed copolymer-MORF2 complex can comprise 10 grafted morpholinos. In an aspect, a disclosed copolymer-MORF2 complex can comprise more than 10 grafted morpholinos. In an aspect, the one or more morpholinos or grafted morpholinos can have the same sequence. In an aspect, the one or more morpholinos can have different sequence. For example, in an aspect multiple morpholinos can be present, wherein the one or more morpholinos comprise different sequences or wherein the one or more morpholinos comprise the same sequence or a combination thereof.

In an aspect of a disclosed kit, the morpholino of the first complex can comprise 10 bp-40 bp and the one or more morpholinos of the second complex can comprise 10 bp-40 bp. For example, in an aspect, each of the morpholinos in a disclosed kit can be 10 bp in length, 12 bp in length, 15 bp in length, 18 bp in length, 20 bp in length, 23 bp in length, 25 bp in length, 28 bp in length, 30 bp in length, 32 bp in length, 35 bp in length, 38 bp in length, or 40 bp in length. In an aspect, each of the morpholinos can comprise about 35% to about 65% GC content. In an aspect, each of the morpholinos can comprise a G content less than 36%. In an aspect, each of the morpholinos can comprise no more than 7 C's.

In an aspect of a disclosed kit, the morpholino of the first complex can be 40 bp in length and the one or more morpholinos of the second complex can be 40 bp in length. In an aspect, the morpholino of the first complex can be 5' GAA CTA ATG CAA TAA CTA TCA CGA ATG CGG GTA ACT TAA T 3' (SEQ ID NO:1) and the one or more morpholinos of the second complex can be 5' ATT AAG TTA CCC GCA TTC GTG ATA GTT ATT GCA TTA GTT C 3' (SEQ ID NO:2). In an aspect, the morpholino of the first complex can be GAA ACC GCT ATT TAT TGG CTA AGA ACA GAT ACG AAT CAT A 3' (SEQ ID NO:3) and the one or more morpholinos of the second complex can be 5' TAT GAT TCG TAT CTG TTC TTA GCC AAT AAA TAG CGG TTT C 3' (SEQ ID NO:4).

In an aspect of a disclosed kit, the morpholino of the first complex can be 38 bp in length and the one or more morpholinos of the second complex can be 38 bp in length. In an aspect, the morpholino of the first complex can be 5' GTA AAC GCG ACA AAT GCC GAT AAT GCT TCG ATA ATA AT 3' (SEQ ID NO:5) and the one or more morpholinos of the second complex can be 5' ATT ATT ATC GAA GCA TTA TCG GCA TTT GTC GCG TTT AC 3' (SEQ ID NO:6). In an aspect, the morpholino of the first complex can be 5' GAC AGA GTT CAC TAT GAC AAA CGA TTT CAC GAG TAA TA 3' (SEQ ID NO:7) and the one or more morpholinos of the second complex can be 5' TAT TAC TCG TGA AAT CGT TTG TCA TAG TGA ACT CTG TC 3' (SEQ ID NO:8).

In an aspect of a disclosed kit, the morpholino of the first complex can be 35 bp in length and the one or more morpholinos of the second complex can be 35 bp in length. In an aspect, the morpholino of the first complex can be 5' CCT GAT ACA GAA GTA GAA AGC AGT CAC GCA ATA TA 3' (SEQ ID NO:9) and the one or more morpholinos of the second complex can be 5' TAT ATT GCG TGA CTG CTT TCT ACT TCT GTA TCA GG 3' (SEQ ID NO:10). In an aspect, the morpholino of the first complex can be 5' GAA CAA CGA GAG GTG CTC AAT ACA GAT ATC AAT CA 3' (SEQ ID NO:11) and the one or more morpholinos of the second complex can be 5' TGA TTG ATA TCT GTA TTG AGC ACC TCT CGT TGT TC 3' (SEQ ID NO:12).

In an aspect of a disclosed kit, the morpholino of the first complex can be 32 bp in length and the one or more morpholinos of the second complex can be 32 bp in length. In an aspect, the morpholino of the first complex can be 5' AGT CAT AGA TAG ACA GAA TAG CCG GAT AAA CT 3' (SEQ ID NO:13) and the one or more morpholinos of the second complex can be 5' AGT TTA TCC GGC TAT TCT GTC TAT CTA TGA CT 3' (SEQ ID NO:14). In an aspect, the morpholino of the first complex can be 5' GAT ACA GAA GTA GAA AGC AGT CAC GCA ATA TA 3' (SEQ ID NO:15) and the one or more morpholinos of the second complex can be 5' TAT ATT GCG TGA CTG CTT TCT ACT TCT GTA TC 3' (SEQ ID NO:16).

In an aspect of a disclosed kit, the morpholino of the first complex can be 30 bp in length and the one or more morpholinos of the second complex can be 30 bp in length. In an aspect, the morpholino of the first complex can be 5' GGC ATA GAT AAC AGA ATA GCC GGA TAA ACT 3' (SEQ ID NO:17) and the one or more morpholinos of the second complex can be 5' AGT TTA TCC GGC TAT TCT GTT ATC TAT GCC 3' (SEQ ID NO:18). In an aspect, the morpholino of the first complex can be 5' GAC CAG TAG ATA AGT GAA CCA GAT TGA ACA 3' (SEQ ID NO:19) and the one or more morpholinos of the second complex can be 5' TGT TCA ATC TGG TTC ACT TAT CTA CTG GTC 3' (SEQ ID NO:20).

In an aspect of a disclosed kit, the morpholino of the first complex can be 28 bp in length and the one or more morpholinos of the second complex can be 28 bp in length. In an aspect, the morpholino of the first complex can be 5' GAG TAC AGC CAG AGA GAG AAT CAA TAT A 3' (SEQ ID NO:21) and the one or more morpholinos of the second complex can be 5' TAT ATT GAT TCT CTC TCT GGC TGT ACT C 3' (SEQ ID NO:22). In an aspect, the morpholino of the first complex can be 5' GTG AAC ACG AAA GAG TGA CGC AAT AAA T 3' (SEQ ID NO:23) and the one or more morpholinos of the second complex can be 5' ATT TAT TGC GTC ACT CTT TCG TGT TCA C 3' (SEQ ID NO:24).

In an aspect of a disclosed kit, the morpholino of the first complex can be 25 bp in length and the one or more morpholinos of the second complex can be 25 bp in length. In an aspect, the morpholino of the first complex can be 5' GAG TAA GCC AAG GAG AAT CAA TAT A 3' (SEQ ID NO:25) and the one or more morpholinos of the second complex can be 5' TAT ATT GAT TCT CCT TGG CTT ACT C 3' (SEQ ID NO:26). In an aspect, the morpholino of the first complex can be 5' AGA TGA CGA TAA AGA CGC AAA GAT T 3' (SEQ ID NO:27) and the one or more morpholinos of the second complex can be 5' AAT CTT TGC GTC TTT ATC GTC ATC T 3' (SEQ ID NO:28). In an aspect, the morpholino of the first complex can comprise 3 C's, 6 G's, 12 A's, and 4 T's and the one or more morpholinos of the second complex can comprise 6 C's, 3 G's, 4 A's, and 12 T's.

In an aspect of a disclosed kit, the morpholino of the first complex can be 23 bp in length and the one or more morpholinos of the second complex can be 23 bp in length. In an aspect, the morpholino of the first complex can be 5' GGA CCA AGT AAA CAG GGA TAT AT 3' (SEQ ID NO:29) and the one or more morpholinos of the second complex can be 5' ATA TAT CCC TGT TTA CTT GGT CC 3' (SEQ ID NO:30). In an aspect, the morpholino of the first complex can be 5' GCT GAA AAC CAA TAT GAG AGT GA 3' (SEQ ID NO:31) and the one or more morpholinos of the second complex can be 5' TCA CTC TCA TAT TGG TTT TCA GC 3' (SEQ ID NO:32).

In an aspect of a disclosed kit, the morpholino of the first complex can be 20 bp in length and the one or more morpholinos of the second complex can be 20 bp in length. In an aspect, the morpholino of the first complex can be 5' GAT GAA GTA CCG ACA AGA TA 3' (SEQ ID NO:33) and the one or more morpholinos of the second complex can be 5' TAT CTT GTC GGT ACT TCA TC 3' (SEQ ID NO:34). In an aspect, the morpholino of the first complex can be 5' GAC AGG ATG AAT AAC ACA GT 3' (SEQ ID NO:35) and the one or more morpholinos of the second complex can be 5' ACT GTG TTA TTC ATC CTG TC 3' (SEQ ID NO:36).

In an aspect of a disclosed kit, the morpholino of the first complex can be 18 bp in length and the one or more morpholinos of the second complex can be 18 bp in length. In an aspect, the morpholino of the first complex can be 5' GCA GCA AAC GAA GTA TAT 3' (SEQ ID NO:37) and the one or more morpholinos of the second complex can be 5' ATA TAC TTC GTT TGC TGC 3' (SEQ ID NO:38). In an aspect, the morpholino of the first complex can be 5' GTC ATA ACA GAA CAG GTA 3' (SEQ ID NO:39) and the one or more morpholinos of the second complex can be 5' TAC CTG TTC TGT TAT GAC 3' (SEQ ID NO:40).

In an aspect of a disclosed kit, the morpholino of the first complex can be 15 bp in length and the one or more morpholinos of the second complex can be 15 bp in length. In an aspect, the morpholino of the first complex can be 5' TCA AGA CAG AAG GAT 3' (SEQ ID NO:41) and the one or more morpholinos of the second complex can be 5' ATC CTT CTG TCT TGA 3' (SEQ ID NO:42). In an aspect, the morpholino of the first complex can be 5' TAG CAA CAT AGG AAG 3' (SEQ ID NO:43) and the one or more morpholinos of the second complex can be 5' CTT CCT ATG TTG CTA 3' (SEQ ID NO:44).

In an aspect of a disclosed kit, the morpholino of the first complex can be 12 bp in length and the one or more morpholinos of the second complex can be 12 bp in length. In an aspect, the morpholino of the first complex can be 5' CAG AGA GCA TAT 3' (SEQ ID NO:45) and the one or more morpholinos of the second complex can be 5' ATA TGC TCT CTG 3' (SEQ ID NO:46). In an aspect, the morpholino of the first complex can be 5' CAA GAG GTA CAT 3' (SEQ ID NO:47) and the one or more morpholinos of the second complex can be 5' ATG TAC CTC TTG 3' (SEQ ID NO:48).

In an aspect of a disclosed kit, the morpholino of the first complex can be 10 bp in length and the one or more morpholinos of the second complex can be 10 bp in length. In an aspect, the morpholino of the first complex can be 5' AAG AGG TAC A 3' (SEQ ID NO:49) and the one or more morpholinos of the second complex can be 5' TGT ACC TCT T 3' (SEQ ID NO:50). In an aspect, the morpholino of the first complex can be 5' AAG GAC AGT A 3' (SEQ ID NO:51) and the one or more morpholinos of the second complex can be 5' TAC TGT CCT T 3' (SEQ ID NO:52).

iv) Pharmaceutical Compositions

Disclosed herein are pharmaceutical compositions comprising a disclosed composition comprising one or more disclosed complexes. For example, in an aspect, a disclosed pharmaceutical composition comprises (i) a complex comprising a targeting moiety and an oligonucleotide and (ii) a pharmaceutically acceptable carrier. In an aspect, a disclosed pharmaceutical composition comprises (i) a complex comprising a copolymer carrier and one or more oligonucleotides and (ii) a pharmaceutically acceptable carrier. In an aspect, a disclosed pharmaceutical composition comprises (i) a first complex comprising a targeting moiety and an oligonucleotide, (ii) a second complex comprising a copolymer carrier and one or more oligonucleotides, and (iii) a pharmaceutically acceptable carrier.

In an aspect, a disclosed pharmaceutical composition can be administered to a subject in need of treatment of a B-cell malignancy, an inflammatory disorder, or an auto-immune disease with B cell involvement. For example, in an aspect, a disclosed pharmaceutical composition can be administered to a subject in need of treatment of a NHL. In an aspect, a disclosed pharmaceutical composition can be administered to a subject in need of treatment of one or more of the following: rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a disclosed pharmaceutical composition can be administered to a subject in need of treatment following receipt of a transplanted organ. In an aspect, a disclosed pharmaceutical composition can be administered to a subject in need of treatment, wherein the subject has JC virus.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Tablets and capsules are the preferred oral dosage units whereby solid pharmaceutical carriers are employed. Optionally, tablets can be coated by standard aqueous or nonaqueous techniques. A tablet containing a composition or complex disclosed herein can be prepared by compression or molding, optionally with one or more accessory ingredients or adjuvants. Compressed tablets can be prepared by compressing, in a suitable machine, a disclosed complex of composition in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

It is understood that the disclosed compositions can be prepared from the disclosed compounds. It is also understood that the disclosed compositions can be employed in the disclosed methods of using.

C. METHODS i) Method of Inducing Apoptosis

Disclosed herein are methods of inducing apoptosis, comprising contacting a population of cells with a first complex comprising a targeting moiety and an oligonucleotide; contacting a population of cells with a second complex comprising a copolymer carrier and one or more oligonucleotides; wherein the contacting of the cells with the first complex and the second complex induces apoptosis of the cells. In an aspect, a disclosed method can comprise repeating contacting a population of cells with a first complex comprising a targeting moiety and an oligonucleotide. In an aspect, a disclosed method can comprise repeating contacting a population of cells with a second complex comprising a copolymer carrier and one or more oligonucleotides. In an aspect, a disclosed method can comprise contacting a population of cells with a first complex comprising a targeting moiety and an oligonucleotide and contacting a population of cells with a second complex comprising a copolymer carrier and one or more oligonucleotides. In an aspect, the skilled person can determine an efficacious dose, an efficacious schedule, or an efficacious route of administration for a disclosed composition or a disclosed complex so as to induce apoptosis.

In an aspect, a disclosed method of inducing apoptosis can comprise confirming apoptosis of the cells. Methods of confirming apoptosis are known to the art and include, but are not limited to: measuring caspase-3 activity, measuring annexin V/propidium iodine binding, and measuring terminal deoxynucleotidyl transferase dUTP nick end-labeling. In an aspect, confirming apoptosis can comprise one of the following: measuring caspase-3 activity, measuring annexin V/propidium iodine binding, and measuring terminal deoxynucleotidyl transferase dUTP nick end-labeling. In an aspect, confirming apoptosis can comprise two of the following: measuring caspase-3 activity, measuring annexin V/propidium iodine binding, and measuring terminal deoxynucleotidyl transferase dUTP nick end-labeling. In an aspect, confirming apoptosis can comprise all of the following: measuring caspase-3 activity, measuring annexin V/propidium iodine binding, and measuring terminal deoxynucleotidyl transferase dUTP nick end labeling.

In an aspect of a disclosed method of inducing apoptosis, the population of cells can be B-cells. In an aspect, B-cells can be normal B-cells. In an aspect, cells can be malignant B-cells. In an aspect, the population of cells can be in a subject. In an aspect, B-cells can be in a subject. In an aspect, a subject can have non-Hodgkin's lymphoma. In an aspect, a subject can have received an organ transplant. In an aspect, a subject can have JC virus. In an aspect, a subject can have rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy.

In an aspect of a disclosed method of inducing apoptosis, a targeting moiety can be specific for a non-internalizing cell surface molecule or slowly internalizing cell surface molecule. Examples of a non-internalizing cell surface molecule or a slowly internalizing cell surface molecule are known to the art. In an aspect, a non-internalizing cell surface molecule or slowly internalizing cell surface molecule can be on a cell or a population of cells. In an aspect, a cell or a population of cells can be B-cells. In an aspect, the B-cells can be normal B-cells. In an aspect, the B-cells can be malignant B-cells.

In an aspect of a disclosed method of inducing apoptosis, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect of a disclosed method, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamers. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

In an aspect of a disclosed method of inducing apoptosis, a copolymer carrier can be water-soluble. In an aspect, a copolymer carrier can comprise a main chain and one or more side chains. In an aspect, a main chain of a copolymer carrier can comprise enzymatically degradable sequences. In an aspect, one or more side chains of a copolymer carrier can comprise enzymatically degradable sequences. In an aspect, one or more side chains of a copolymer carrier can terminate in a functional group. Functional groups are known to the art and include, but are not limited to: an amine reactive active ester, a maleimide, an azide, a disulfide, and an alkyne. In an aspect, a functional group can permit the binding of one or more oligonucleotides to one or more side chains of a disclosed copolymer complex. In an aspect, one or more side chains can be conjugated to one or more oligonucleotides via a disclosed functional group. In an aspect, a main chain of a disclosed copolymer carrier can comprise N-(2-hydroxypropyl)methylacrylamide (HPMA) copolymerized with N-methacryloylglycylglycine-thiazolidine-2-thione (MA-GG-TT) monomers. In an aspect, a main chain of a disclosed copolymer carrier can comprise N-(2-hydroxypropyl)methylacrylamide (HPMA) copolymerized with N-methacryloylglycylglycine-p-nitrophenyl ester (MA-GG-ONp) monomers.

Oligonucleotides are well known to the art. In an aspect of a disclosed method of inducing apoptosis, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed method of inducing apoptosis, an oligonucleotide can be a peptide nucleic acid. In an aspect of a disclosed method, an oligonucleotide can be a morpholino. In an aspect, a morpholino does not bind to any mRNA target of a genome, such as, for example, the human genome. In an aspect, a morpholino is not self-complementary. In an aspect of a disclosed method, the morpholino of the first complex and the one or more morpholinos of the second complex can be complementary. In an aspect, the morpholino of the first complex is not self-complementary. In an aspect, the one or more morpholinos of the second complex are not self-complementary. In an aspect, the morpholino of the first complex and the one or more morpholinos of the second complex can have a Kd smaller than $10^{-7}$ M. In an aspect, the morpholino of the first complex and the one or more morpholinos of the second complex can have a Kd smaller than 10 M.

In an aspect of a disclosed method of inducing apoptosis, the morpholino of the first complex can comprise 10 bp-40 bp and the one or more morpholinos of the second complex can comprise 10 bp-40 bp. For example, in an aspect, each of the morpholinos in a disclosed method can be 10 bp in length, 12 bp in length, 15 bp in length, 18 bp in length, 20 bp in length, 23 bp in length, 25 bp in length, 28 bp in length, 30 bp in length, 32 bp in length, 35 bp in length, 38 bp in length, or 40 bp in length. In an aspect, each of the morpholinos can comprise about 35% to about 65% GC content. In an aspect, each of the morpholinos can comprise a G content less than 36%. In an aspect, each of the morpholinos can comprise no more than 7 C's.

In an aspect of a disclosed method of inducing apoptosis, the morpholino of the first complex can be 40 bp in length and the one or more morpholinos of the second complex can be 40 bp in length. In an aspect, the morpholino of the first complex can be 5' GAA CTA ATG CAA TAA CTA TCA CGA ATG CGG GTA ACT TAA T 3' (SEQ ID NO:1) and the one or more morpholinos of the second complex can be 5' ATT AAG TTA CCC GCA TTC GTG ATA GTT ATT GCA TTA GTT C 3' (SEQ ID NO:2). In an aspect, the morpholino of the first complex can be GAA ACC GCT ATT TAT TGG CTA AGA ACA GAT ACG AAT CAT A 3' (SEQ ID NO:3) and the one or more morpholinos of the second complex can be 5' TAT GAT TCG TAT CTG TTC TTA GCC AAT AAA TAG CGG TTT C 3' (SEQ ID NO:4).

In an aspect of a disclosed method of inducing apoptosis, the morpholino of the first complex can be 38 bp in length and the one or more morpholinos of the second complex can be 38 bp in length. In an aspect, the morpholino of the first complex can be 5' GTA AAC GCG ACA AAT GCC GAT AAT GCT TCG ATA ATA AT 3' (SEQ ID NO:5) and the one or more morpholinos of the second complex can be 5' ATT ATT ATC GAA GCA TTA TCG GCA TTT GTC GCG TTT AC 3' (SEQ ID NO:6). In an aspect, the morpholino of the first complex can be 5' GAC AGA GTT CAC TAT GAC AAA CGA TTT CAC GAG TAA TA 3' (SEQ ID NO:7) and the one or more morpholinos of the second complex can be 5' TAT TAC TCG TGA AAT CGT TTG TCA TAG TGA ACT CTG TC 3' (SEQ ID NO:8).

In an aspect of a disclosed method of inducing apoptosis, the morpholino of the first complex can be 35 bp in length and the one or more morpholinos of the second complex can be 35 bp in length. In an aspect, the morpholino of the first complex can be 5' CCT GAT ACA GAA GTA GAA AGC AGT CAC GCA ATA TA 3' (SEQ ID NO:9) and the one or more morpholinos of the second complex can be 5' TAT ATT GCG TGA CTG CTT TCT ACT TCT GTA TCA GG 3' (SEQ ID NO:10). In an aspect, the morpholino of the first complex can be 5' GAA CAA CGA GAG GTG CTC AAT ACA GAT ATC AAT CA 3' (SEQ ID NO:11) and the one or more morpholinos of the second complex can be 5' TGA TTG ATA TCT GTA TTG AGC ACC TCT CGT TGT TC 3' (SEQ ID NO:12).

In an aspect of a disclosed method of inducing apoptosis, the morpholino of the first complex can be 32 bp in length and the one or more morpholinos of the second complex can be 32 bp in length. In an aspect, the morpholino of the first complex can be 5' AGT CAT AGA TAG ACA GAA TAG CCG GAT AAA CT 3' (SEQ ID NO:13) and the one or more morpholinos of the second complex can be 5' AGT TTA TCC GGC TAT TCT GTC TAT CTA TGA CT 3' (SEQ ID NO:14). In an aspect, the morpholino of the first complex can be 5' GAT ACA GAA GTA GAA AGC AGT CAC GCA ATA TA 3' (SEQ ID NO:15) and the one or more morpholinos of the second complex can be 5' TAT ATT GCG TGA CTG CTT TCT ACT TCT GTA TC 3' (SEQ ID NO:16).

In an aspect of a disclosed method of inducing apoptosis, the morpholino of the first complex can be 30 bp in length and the one or more morpholinos of the second complex can be 30 bp in length. In an aspect, the morpholino of the first complex can be 5' GGC ATA GAT AAC AGA ATA GCC GGA TAA ACT 3' (SEQ ID NO:17) and the one or more morpholinos of the second complex can be 5' AGT TTA TCC GGC TAT TCT GTT ATC TAT GCC 3' (SEQ ID NO:18). In an aspect, the morpholino of the first complex can be 5' GAC CAG TAG ATA AGT GAA CCA GAT TGA ACA 3' (SEQ ID NO:19) and the one or more morpholinos of the second complex can be 5' TGT TCA ATC TGG TTC ACT TAT CTA CTG GTC 3' (SEQ ID NO:20).

In an aspect of a disclosed method of inducing apoptosis, the morpholino of the first complex can be 28 bp in length and the one or more morpholinos of the second complex can be 28 bp in length. In an aspect, the morpholino of the first complex can be 5' GAG TAC AGC CAG AGA GAG AAT CAA TAT A 3' (SEQ ID NO:21) and the one or more morpholinos of the second complex can be 5' TAT ATT GAT TCT CTC TCT GGC TGT ACT C 3' (SEQ ID NO:22). In an aspect, the morpholino of the first complex can be 5' GTG AAC ACG AAA GAG TGA CGC AAT AAA T 3' (SEQ ID NO:23) and the one or more morpholinos of the second complex can be 5' ATT TAT TGC GTC ACT CTT TCG TGT TCA C 3' (SEQ ID NO:24).

In an aspect of a disclosed method of inducing apoptosis, the morpholino of the first complex can be 25 bp in length and the one or more morpholinos of the second complex can be 25 bp in length. In an aspect, the morpholino of the first complex can be 5' GAG TAA GCC AAG GAG AAT CAA TAT A 3' (SEQ ID NO:25) and the one or more morpholinos of the second complex can be 5' TAT ATT GAT TCT CCT TGG CTT ACT C 3' (SEQ ID NO:26). In an aspect, the morpholino of the first complex can be 5' AGA TGA CGA TAA AGA CGC AAA GAT T 3' (SEQ ID NO:27) and the one or more morpholinos of the second complex can be 5' AAT CTT TGC GTC TTT ATC GTC ATC T 3' (SEQ ID NO:28). In an aspect, the morpholino of the first complex can comprise 3 cytidines, 6 guanosines, 12 adenosines, and 4 thymidines and the one or more morpholinos of the second complex can comprise 6 cytidines, 3 guanosines, 4 adenosines, and 12 thymidines.

In an aspect of a disclosed method of inducing apoptosis, the morpholino of the first complex can be 23 bp in length and the one or more morpholinos of the second complex can be 23 bp in length. In an aspect, the morpholino of the first complex can be 5' GGA CCA AGT AAA CAG GGA TAT AT 3' (SEQ ID NO:29) and the one or more morpholinos of the second complex can be 5' ATA TAT CCC TGT TTA CTT GGT CC 3' (SEQ ID NO:30). In an aspect, the morpholino of the first complex can be 5' GCT GAA AAC CAA TAT GAG AGT GA 3' (SEQ ID NO:31) and wherein the one or more morpholinos of the second complex can be 5' TCA CTC TCA TAT TGG TTT TCA GC 3' (SEQ ID NO:32).

In an aspect of a disclosed method of inducing apoptosis, the morpholino of the first complex can be 20 bp in length and the one or more morpholinos of the second complex can be 20 bp in length. In an aspect, the morpholino of the first complex can be 5' GAT GAA GTA CCG ACA AGA TA 3' (SEQ ID NO:33) and the one or more morpholinos of the second complex can be 5' TAT CTT GTC GGT ACT TCA TC 3' (SEQ ID NO:34). In an aspect, the morpholino of the first complex can be 5' GAC AGG ATG AAT AAC ACA GT 3' (SEQ ID NO:35) and the one or more morpholinos of the second complex can be 5' ACT GTG TTA TTC ATC CTG TC 3' (SEQ ID NO:36).

In an aspect of a disclosed method of inducing apoptosis, the morpholino of the first complex can be 18 bp in length and the one or more morpholinos of the second complex can be 18 bp in length. In an aspect, the morpholino of the first complex can be 5' GCA GCA AAC GAA GTA TAT 3' (SEQ ID NO:37) and the one or more morpholinos of the second complex can be 5' ATA TAC TTC GTT TGC TGC 3' (SEQ ID NO:38). In an aspect, the morpholino of the first complex can be 5' GTC ATA ACA GAA CAG GTA 3' (SEQ ID NO:39) and the one or more morpholinos of the second complex can be 5' TAC CTG TTC TGT TAT GAC 3' (SEQ ID NO:40).

In an aspect of a disclosed method of inducing apoptosis, the morpholino of the first complex can be 15 bp in length and the one or more morpholinos of the second complex can be 15 bp in length. In an aspect, the morpholino of the first complex can be 5' TCA AGA CAG AAG GAT 3' (SEQ ID NO:41) and the one or more morpholinos of the second complex can be 5' ATC CTT CTG TCT TGA 3' (SEQ ID NO:42). In an aspect, the morpholino of the first complex can be 5' TAG CAA CAT AGG AAG 3' (SEQ ID NO:43) and the one or more morpholinos of the second complex can be 5' CTT CCT ATG TTG CTA 3' (SEQ ID NO:44).

In an aspect of a disclosed method of inducing apoptosis, the morpholino of the first complex can be 12 bp in length and the one or more morpholinos of the second complex can be 12 bp in length. In an aspect, the morpholino of the first complex can be 5' CAG AGA GCA TAT 3' (SEQ ID NO:45) and the one or more morpholinos of the second complex can be 5' ATA TGC TCT CTG 3' (SEQ ID NO:46). In an aspect, the morpholino of the first complex can be 5' CAA GAG GTA CAT 3' (SEQ ID NO:47) and the one or more morpholinos of the second complex can be 5' ATG TAC CTC TTG 3' (SEQ ID NO:48).

In an aspect of a disclosed method of inducing apoptosis, the morpholino of the first complex can be 10 bp in length and the one or more morpholinos of the second complex can be 10 bp in length. In an aspect, the morpholino of the first complex can be 5' AAG AGG TAC A 3' (SEQ ID NO:49) and the one or more morpholinos of the second complex can be 5' TGT ACC TCT T 3' (SEQ ID NO:50). In an aspect, the morpholino of the first complex can be 5' AAG GAC AGT A 3' (SEQ ID NO:51) and the one or more morpholinos of the second complex can be 5' TAC TGT CCT T 3' (SEQ ID NO:52).

ii) Method of Inducing Apoptosis

Disclosed herein are methods of inducing apoptosis, comprising contacting a population of cells with a composition comprising a first complex comprising a targeting moiety and an oligonucleotide and a second complex comprising a complex comprising a copolymer carrier and one or more oligonucleotides, wherein the contacting of the cells with the composition induces apoptosis of the cells. A disclosed method can comprise repeating the contacting of the cells with the composition. A disclosed method can comprise confirming apoptosis of the cells. Methods of confirming apoptosis are known to the art and include, but are not limited to: measuring caspase-3 activity, measuring annexin V/propidium iodine binding, and measuring terminal deoxynucleotidyl transferase dUTP nick end-labeling. In an aspect, confirming apoptosis can comprise one of the following: measuring caspase-3 activity, measuring annexin V/propidium iodine binding, and measuring terminal deoxynucleotidyl transferase dUTP nick end-labeling. In an aspect, confirming apoptosis can comprise two of the following: measuring caspase-3 activity, measuring annexin V/propidium iodine binding, and measuring terminal deoxynucleotidyl transferase dUTP nick end-labeling. In an aspect, confirming apoptosis can comprise all of the following: measuring caspase-3 activity, measuring annexin V/propidium iodine binding, and measuring terminal deoxynucleotidyl transferase dUTP nick end-labeling. In an aspect, the skilled person can determine an efficacious dose, an efficacious schedule, or an efficacious route of administration for a disclosed composition or a disclosed complex so as to induce apoptosis.

In an aspect of a disclosed method of inducing apoptosis, the population of cells can be B-cells. In an aspect, B-cells can be normal B-cells. In an aspect, cells can be malignant B-cells. In an aspect, the population of cells can be in a subject. In an aspect, B-cells can be in a subject. In an aspect, a subject can have non-Hodgkin's lymphoma. In an aspect, a subject can have received an organ transplant. In an aspect, a subject can have JC virus. In an aspect, a subject can have rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy.

In an aspect of a disclosed method of inducing apoptosis, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18

(TNFRSF18). In an aspect, a receptor can be a TNF-like weak inducer of apoptosis receptor (TWEAK or TNFSF12).

In an aspect of a disclosed method of inducing apoptosis, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamers. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

In an aspect of a disclosed method of inducing apoptosis, a copolymer carrier can be water-soluble. In an aspect, a copolymer carrier can comprise a main chain and one or more side chains. In an aspect, a main chain of a copolymer carrier can comprise enzymatically degradable sequences. In an aspect, one or more side chains of a copolymer carrier can comprise enzymatically degradable sequences. In an aspect, one or more side chains of a copolymer carrier can terminate in a functional group. Functional groups are known to the art and include, but are not limited to: an amine reactive active ester, a maleimide, an azide, and an alkyne. In an aspect, a functional group can permit the binding of one or more oligonucleotides to one or more side chains of a disclosed copolymer complex. In an aspect, one or more side chains can be conjugated to one or more oligonucleotides via a disclosed functional group. In an aspect, a main chain can comprise N-(2-hydroxypropyl)methylacrylamide (HPMA) copolymerized with N-methacryloylglycylglycine-thiazolidine-2-thione (MA-GG-TT) monomers. In an aspect, a main chain copolymer carrier can comprise N-(2-hydroxypropyl) methylacrylamide (HPMA) copolymerized with N-methacryloylglycylglycine-p-nitrophenyl ester (MA-GG-ONp) monomers.

Oligonucleotides are well known to the art. In an aspect of a disclosed method, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed method of inducing apoptosis, an oligonucleotide can be a peptide nucleic acid. In an aspect of a disclosed method, an oligonucleotide can be a morpholino. In an aspect, a morpholino does not bind to any mRNA target of a genome, such as, for example, the human genome. In an aspect, a morpholino is not self-complementary. In an aspect of a disclosed method, the morpholino of the first complex and the one or more morpholinos of the second complex can be complementary. In an aspect, the morpholino of the first complex is not self-complementary. In an aspect, the one or more morpholinos of the second complex are not self-complementary. In an aspect, the morpholino of the first complex and the one or more morpholinos of the second complex can have a Kd smaller than $10^{-7}$ M. In an aspect, the morpholino of the first complex and the one or more morpholinos of the second complex can have a Kd smaller than 10 M.

In an aspect of a disclosed method of inducing apoptosis, the morpholino of the first complex can comprise 10 bp-40 bp and the one or more morpholinos of the second complex can comprise 10 bp-40 bp. For example, in an aspect, each of the morpholinos in a disclosed method can be 10 bp in length, 12 bp in length, 15 bp in length, 18 bp in length, 20 bp in length, 23 bp in length, 25 bp in length, 28 bp in length, 30 bp in length, 32 bp in length, 35 bp in length, 38 bp in length, or 40 bp in length. In an aspect, each of the morpholinos can comprise about 35% to about 65% GC content. In an aspect, each of the morpholinos can comprise a G content less than 36%. In an aspect, each of the morpholinos can comprise no more than 7 C's.

In an aspect of a disclosed method of inducing apoptosis, the morpholino of the first complex can be 40 bp in length and the one or more morpholinos of the second complex can be 40 bp in length. In an aspect, the morpholino of the first complex can be 5' GAA CTA ATG CAA TAA CTA TCA CGA ATG CGG GTA ACT TAA T 3' (SEQ ID NO:1) and the one or more morpholinos of the second complex can be 5' ATT AAG TTA CCC GCA TTC GTG ATA GTT ATT GCA TTA GTT C 3' (SEQ ID NO:2). In an aspect, the morpholino of the first complex can be GAA ACC GCT ATT TAT TGG CTA AGA ACA GAT ACG AAT CAT A 3' (SEQ ID NO:3) and the one or more morpholinos of the second complex can be 5' TAT GAT TCG TAT CTG TTC TTA GCC AAT AAA TAG CGG TTT C 3' (SEQ ID NO:4).

In an aspect of a disclosed method of inducing apoptosis, the morpholino of the first complex can be 38 bp in length and the one or more morpholinos of the second complex can be 38 bp in length. In an aspect, the morpholino of the first complex can be 5' GTA AAC GCG ACA AAT GCC GAT AAT GCT TCG ATA ATA AT 3' (SEQ ID NO:5) and the one or more morpholinos of the second complex can be 5' ATT ATT ATC GAA GCA TTA TCG GCA TTT GTC GCG TTT AC 3' (SEQ ID NO:6). In an aspect, the morpholino of the first complex can be 5' GAC AGA GTT CAC TAT GAC AAA CGA TTT CAC GAG TAA TA 3' (SEQ ID NO:7) and the one or more morpholinos of the second complex can be 5' TAT TAC TCG TGA AAT CGT TTG TCA TAG TGA ACT CTG TC 3' (SEQ ID NO:8).

In an aspect of a disclosed method of inducing apoptosis, the morpholino of the first complex can be 35 bp in length and the one or more morpholinos of the second complex can be 35 bp in length. In an aspect, the morpholino of the first complex can be 5' CCT GAT ACA GAA GTA GAA AGC AGT CAC GCA ATA TA 3' (SEQ ID NO:9) and the one or more morpholinos of the second complex can be 5' TAT ATT GCG TGA CTG CTT TCT ACT TCT GTA TCA GG 3' (SEQ ID NO:10). In an aspect, the morpholino of the first complex can be 5' GAA CAA CGA GAG GTG CTC AAT ACA GAT ATC AAT CA 3' (SEQ ID NO:11) and the one or more morpholinos of the second complex can be 5' TGA TTG ATA TCT GTA TTG AGC ACC TCT CGT TGT TC 3' (SEQ ID NO:12).

In an aspect of a disclosed method of inducing apoptosis, the morpholino of the first complex can be 32 bp in length and the one or more morpholinos of the second complex can be 32 bp in length. In an aspect, the morpholino of the first complex can be 5' AGT CAT AGA TAG ACA GAA TAG CCG GAT AAA CT 3' (SEQ ID NO:13) and the one or more morpholinos of the second complex can be 5' AGT TTA TCC GGC TAT TCT GTC TAT CTA TGA CT 3' (SEQ ID NO:14). In an aspect, the morpholino of the first complex can be 5' GAT ACA GAA GTA GAA AGC AGT CAC GCA ATA TA 3' (SEQ ID NO:15) and the one or more morpholinos of the second complex can be 5' TAT ATT GCG TGA CTG CTT TCT ACT TCT GTA TC 3' (SEQ ID NO:16).

In an aspect of a disclosed method of inducing apoptosis, the morpholino of the first complex can be 30 bp in length and the one or more morpholinos of the second complex can be 30 bp in length. In an aspect, the morpholino of the first complex can be 5' GGC ATA GAT AAC AGA ATA GCC GGA TAA ACT 3' (SEQ ID NO:17) and the one or more morpholinos of the second complex can be 5' AGT TTA TCC GGC TAT TCT GTT ATC TAT GCC 3' (SEQ ID NO:18). In an aspect, the morpholino of the first complex can be 5' GAC CAG TAG ATA AGT GAA CCA GAT TGA ACA 3' (SEQ ID NO:19) and the one or more morpholinos of the second complex can be 5' TGT TCA ATC TGG TTC ACT TAT CTA CTG GTC 3' (SEQ ID NO:20).

In an aspect of a disclosed method of inducing apoptosis, the morpholino of the first complex can be 28 bp in length and the one or more morpholinos of the second complex can be 28 bp in length. In an aspect, the morpholino of the first complex can be 5' GAG TAC AGC CAG AGA GAG AAT CAA TAT A 3' (SEQ ID NO:21) and the one or more morpholinos of the second complex can be 5' TAT ATT GAT TCT CTC TCT GGC TGT ACT C 3' (SEQ ID NO:22). In an aspect, the morpholino of the first complex can be 5' GTG AAC ACG AAA GAG TGA CGC AAT AAA T 3' (SEQ ID NO:23) and the one or more morpholinos of the second complex can be 5' ATT TAT TGC GTC ACT CTT TCG TGT TCA C 3' (SEQ ID NO:24).

In an aspect of a disclosed method of inducing apoptosis, the morpholino of the first complex can be 25 bp in length and the one or more morpholinos of the second complex can be 25 bp in length. In an aspect, the morpholino of the first complex can be 5' GAG TAA GCC AAG GAG AAT CAA TAT A 3' (SEQ ID NO:25) and the one or more morpholinos of the second complex can be 5' TAT ATT GAT TCT CCT TGG CTT ACT C 3' (SEQ ID NO:26). In an aspect, the morpholino of the first complex can be 5' AGA TGA CGA TAA AGA CGC AAA GAT T 3' (SEQ ID NO:27) and the one or more morpholinos of the second complex can be 5' AAT CTT TGC GTC TTT ATC GTC ATC T 3' (SEQ ID NO:28). In an aspect, the morpholino of the first complex can comprise 3 cytidines, 6 guanosines, 12 adenosines, and 4 thymidines and the one or more morpholinos of the second complex can comprise 6 cytidines, 3 guanosines, 4 adenosines, and 12 thymidines.

In an aspect of a disclosed method of inducing apoptosis, the morpholino of the first complex can be 23 bp in length and the one or more morpholinos of the second complex can be 23 bp in length. In an aspect, the morpholino of the first complex can be 5' GGA CCA AGT AAA CAG GGA TAT AT 3' (SEQ ID NO:29) and the one or more morpholinos of the second complex can be 5' ATA TAT CCC TGT TTA CTT GGT CC 3' (SEQ ID NO:30). In an aspect, the morpholino of the first complex can be 5' GCT GAA AAC CAA TAT GAG AGT GA 3' (SEQ ID NO:31) and wherein the one or more morpholinos of the second complex can be 5' TCA CTC TCA TAT TGG TTT TCA GC 3' (SEQ ID NO:32).

In an aspect of a disclosed method of inducing apoptosis, the morpholino of the first complex can be 20 bp in length and the one or more morpholinos of the second complex can be 20 bp in length. In an aspect, the morpholino of the first complex can be 5' GAT GAA GTA CCG ACA AGA TA 3' (SEQ ID NO:33) and the one or more morpholinos of the second complex can be 5' TAT CTT GTC GGT ACT TCA TC 3' (SEQ ID NO:34). In an aspect, the morpholino of the first complex can be 5' GAC AGG ATG AAT AAC ACA GT 3' (SEQ ID NO:35) and the one or more morpholinos of the second complex can be 5' ACT GTG TTA TTC ATC CTG TC 3' (SEQ ID NO:36).

In an aspect of a disclosed method of inducing apoptosis, the morpholino of the first complex can be 18 bp in length and the one or more morpholinos of the second complex can be 18 bp in length. In an aspect, the morpholino of the first complex can be 5' GCA GCA AAC GAA GTA TAT 3' (SEQ ID NO:37) and the one or more morpholinos of the second complex can be 5' ATA TAC TTC GTT TGC TGC 3' (SEQ ID NO:38). In an aspect, the morpholino of the first complex can be 5' GTC ATA ACA GAA CAG GTA 3' (SEQ ID NO:39) and the one or more morpholinos of the second complex can be 5' TAC CTG TTC TGT TAT GAC 3' (SEQ ID NO:40).

In an aspect of a disclosed method of inducing apoptosis, the morpholino of the first complex can be 15 bp in length and the one or more morpholinos of the second complex can be 15 bp in length. In an aspect, the morpholino of the first complex can be 5' TCA AGA CAG AAG GAT 3' (SEQ ID NO:41) and the one or more morpholinos of the second complex can be 5' ATC CTT CTG TCT TGA 3' (SEQ ID NO:42). In an aspect, the morpholino of the first complex can be 5' TAG CAA CAT AGG AAG 3' (SEQ ID NO:43) and the one or more morpholinos of the second complex can be 5' CTT CCT ATG TTG CTA 3' (SEQ ID NO:44).

In an aspect of a disclosed method of inducing apoptosis, the morpholino of the first complex can be 12 bp in length and the one or more morpholinos of the second complex can be 12 bp in length. In an aspect, the morpholino of the first complex can be 5' CAG AGA GCA TAT 3' (SEQ ID NO:45) and the one or more morpholinos of the second complex can be 5' ATA TGC TCT CTG 3' (SEQ ID NO:46). In an aspect, the morpholino of the first complex can be 5' CAA GAG GTA CAT 3' (SEQ ID NO:47) and the one or more morpholinos of the second complex can be 5' ATG TAC CTC TTG 3' (SEQ ID NO:48).

In an aspect of a disclosed method of inducing apoptosis, the morpholino of the first complex can be 10 bp in length and the one or more morpholinos of the second complex can be 10 bp in length. In an aspect, the morpholino of the first complex can be 5' AAG AGG TAC A 3' (SEQ ID NO:49) and the one or more morpholinos of the second complex can be 5' TGT ACC TCT T 3' (SEQ ID NO:50). In an aspect, the morpholino of the first complex can be 5' AAG GAC AGT A 3' (SEQ ID NO:51) and the one or more morpholinos of the second complex can be 5' TAC TGT CCT T 3' (SEQ ID NO:52).

iii) Method of Treatment

Disclosed herein are methods of treatment of a subject in need thereof, the method comprising administering to a subject a first composition comprising a first complex comprising a targeting moiety and an oligonucleotide; and administering to the subject a second composition comprising a second complex comprising a copolymer carrier and one or more oligonucleotides, wherein the administering of the first composition and the second composition induces apoptosis of a targeted population of cells in the subject. In an aspect, administering comprises intravenous administration. In an aspect, a disclosed method can comprise repeating the administration of the first composition. In an aspect, a disclosed method can comprise repeating the administration of the second composition. In an aspect, a disclosed method can comprise repeating the administration of the first composition and repeating the administration of the second composition. In an aspect, a disclosed method can comprise confirming apoptosis of the targeted population of cells. In an aspect, the skilled person can determine an efficacious dose, an efficacious schedule, or an efficacious route of administration for a disclosed composition or a disclosed complex so as to treat a subject in need thereof.

Methods of confirming apoptosis are known to the art and include, but are not limited to: measuring caspase-3 activity, measuring annexin V/propidium iodine binding, and measuring terminal deoxynucleotidyl transferase dUTP nick end-labeling. In an aspect, confirming apoptosis can comprise one of the following: measuring caspase-3 activity, measuring annexin V/propidium iodine binding, and measuring terminal deoxynucleotidyl transferase dUTP nick end-labeling. In an aspect, confirming apoptosis can comprise two of the following: measuring caspase-3 activity, measuring annexin V/propidium iodine binding, and measuring terminal deoxynucleotidyl transferase dUTP nick end-labeling. In an aspect, confirming apoptosis can comprise all of the following: measuring caspase-3 activity, measuring annexin V/propidium iodine binding, and measuring terminal deoxynucleotidyl transferase dUTP nick end-labeling.

In an aspect of a disclosed method of treatment, the population of cells can be B-cells. In an aspect, B-cells can be normal B-cells. In an aspect, cells can be malignant B-cells. In an aspect, the population of cells can be in a subject. In an aspect, B-cells can be in a subject. In an aspect, a subject can have non-Hodgkin's lymphoma. In an aspect, a subject can have received an organ transplant. In an aspect, a subject can have JC virus. In an aspect, a subject can have rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In an aspect, a subject can have one or more of the following: non-Hodgkin's lymphoma, an organ transplant, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy.

In an aspect of a disclosed method of treatment, a non-internalizing cell surface molecule can be a receptor. In an aspect, a slowly internalizing cell surface molecule can be a receptor. For example, non-internalizing cell surface molecules or slowly internalizing cell surface molecules include, but are not limited to: a CD20 receptor, a protein tyrosine phosphatase receptor type C (PTPRC), a cell surface death receptor, a prostate stem cell antigen (PSCA) receptor, and a receptor belonging to the tumor necrosis factor receptor (TNFR) superfamily. The tumor necrosis factor (TNFR) superfamily comprises death receptor 5 (DR5), FAS receptor (CD95), tumor necrosis factor receptor superfamily member 18 (TNFRSF18), and TNF-like weak inducer of apoptosis (TWEAK or TNFSF12). In an aspect, a receptor can be a CD20 receptor. In an aspect, a receptor can be a protein tyrosine phosphatase receptor type C (PTPRC). In an aspect, a receptor can be a cell surface death receptor. In an aspect, a receptor can be a death receptor 4 (DR4). In an aspect, a receptor can be a prostate stem cell antigen (PSCA) receptor. In an aspect, a receptor is a death receptor 5 (DR5). In an aspect, a receptor can be FAS receptor (CD95). In an aspect, a receptor can be a tumor necrosis factor receptor superfamily member 18 (TNFRSF18). In an aspect, a receptor can be a TNF-like weak inducer of apoptosis receptor (TWEAK or TNFSF12).

In an aspect of a disclosed method of treatment, a targeting moiety can be a polysaccharide, a peptide ligand, an aptamer, a Fab' fragment, or a single-chain variable fragment. In an aspect, a targeting moiety can be a polysaccharide. In an aspect, a targeting moiety can be a peptide ligand. In an aspect, a targeting moiety can be an aptamers. In an aspect, a targeting moiety can be a single-chain variable fragment. In an aspect, a targeting moiety can be a Fab' fragment. In an aspect, a Fab' fragment can be humanized. In an aspect, a Fab' fragment can be derived from an anti-CD20 receptor antibody. Examples of anti-CD20 receptor antibodies are known to the art and include, but are not limited to: 1F5, rituximab, tositumomab, ibritumomab, ofatumumab, veltuzumab, ocrelizumab, ocaratuzumab, obinutuzumab, PRO131921, BCD-020, IBI-301, ublituximab, and BLX-301. In an aspect, the anti-CD20 receptor antibody can be 1F5.

In an aspect of a disclosed method of treatment, a copolymer carrier can be water-soluble. In an aspect, a copolymer carrier can comprise a main chain and one or more side chains. In an aspect, a main chain of a copolymer carrier can comprise enzymatically degradable sequences. In an aspect, one or more side chains of a copolymer carrier can comprise enzymatically degradable sequences. In an aspect, one or more side chains of a copolymer carrier can terminate in a functional group. Functional groups are known to the art and include, but are not limited to: an amine reactive active ester, a maleimide, an azide, and an alkyne. In an aspect, a functional group can permit the binding of one or more oligonucleotides to one or more side chains of a disclosed copolymer complex. In an aspect, one or more side chains can be conjugated to one or more oligonucleotides via a disclosed functional group. In an aspect, a main chain of a disclosed copolymer carrier can comprise N-(2-hydroxypropyl)methylacrylamide (HPMA) copolymerized with N-methacryloylglycylglycine-thiazolidine-2-thione (MA-GG-TT) monomers. In an aspect, a main chain of a disclosed copolymer carrier can comprise N-(2-hydroxypropyl)methylacrylamide (HPMA) copolymerized with N-methacryloylglycylglycine-p-nitrophenyl ester (MA-GG-ONp) monomers.

Oligonucleotides are well known to the art. In an aspect of a disclosed method of treatment, an oligonucleotide can be biocompatible. In an aspect, an oligonucleotide can be non-degradable. In an aspect, an oligonucleotide can be water-soluble. In an aspect, an oligonucleotide can be charge-neutral. In an aspect, an oligonucleotide can be biocompatible and non-degradable. In an aspect, an oligonucleotide can be water-soluble and charge-neutral. In an aspect, an oligonucleotide can be one or more of the following: biocompatible, non-degradable, water-soluble, and charge-neutral. For example, in an aspect, an oligonucleotide can be biocompatible, non-degradable, water-soluble, and charge-neutral.

In an aspect of a disclosed method of treatment, an oligonucleotide can be a peptide nucleic acid. In an aspect of a disclosed method, an oligonucleotide can be a morpholino. In an aspect, a morpholino does not bind to any mRNA target of a genome, such as, for example, the human genome. In an aspect, a morpholino is not self-complementary. In an aspect, the morpholino of the first complex and the one or more morpholinos of the second complex can be complementary. In an aspect, the morpholino of the first complex is not self-complementary. In an aspect, the one or more morpholinos of the second complex are not self-complementary. In an aspect, the morpholino of the first complex and the one or more morpholinos of the second complex can have a Kd smaller than $10^{-7}$ M. In an aspect, the morpholino of the first complex and the one or more morpholinos of the second complex can have a Kd smaller than 10 M.

In an aspect of a disclosed method of treatment, the morpholino of the first complex can comprise 10 bp-40 bp and the one or more morpholinos of the second complex can comprise 10 bp-40 bp. For example, in an aspect, each of the morpholinos in a disclosed method can be 10 bp in length, 12 bp in length, 15 bp in length, 18 bp in length, 20 bp in length, 23 bp in length, 25 bp in length, 28 bp in length, 30 bp in length, 32 bp in length, 35 bp in length, 38 bp in length, or 40 bp in length. In an aspect, each of the morpholinos can comprise about 35% to about 65% GC content. In an aspect, each of the morpholinos can comprise a G content less than 36%. In an aspect, each of the morpholinos can comprise no more than 7 C nucleobases.

In an aspect of a disclosed method of treatment, the morpholino of the first complex can be 40 bp in length and the one or more morpholinos of the second complex can be 40 bp in length. In an aspect, the morpholino of the first complex can be 5' GAA CTA ATG CAA TAA CTA TCA CGA ATG CGG GTA ACT TAA T 3' (SEQ ID NO:1) and the one or more morpholinos of the second complex can be 5' ATT AAG TTA CCC GCA TTC GTG ATA GTT ATT GCA TTA GTT C 3' (SEQ ID NO:2). In an aspect, the morpholino of the first complex can be GAA ACC GCT ATT TAT TGG CTA AGA ACA GAT ACG AAT CAT A 3' (SEQ ID NO:3) and the one or more morpholinos of the second complex can be 5' TAT GAT TCG TAT CTG TTC TTA GCC AAT AAA TAG CGG TTT C 3' (SEQ ID NO:4).

In an aspect of a disclosed method of treatment, the morpholino of the first complex can be 38 bp in length and the one or more morpholinos of the second complex can be 38 bp in length. In an aspect, the morpholino of the first complex can be 5' GTA AAC GCG ACA AAT GCC GAT AAT GCT TCG ATA ATA AT 3' (SEQ ID NO:5) and the one or more morpholinos of the second complex can be 5' ATT ATT ATC GAA GCA TTA TCG GCA TTT GTC GCG TTT AC 3' (SEQ ID NO:6). In an aspect, the morpholino of the first complex can be 5' GAC AGA GTT CAC TAT GAC AAA CGA TTT CAC GAG TAA TA 3' (SEQ ID NO:7) and the one or more morpholinos of the second complex can be 5' TAT TAC TCG TGA AAT CGT TTG TCA TAG TGA ACT CTG TC 3' (SEQ ID NO:8).

In an aspect of a disclosed method of treatment, the morpholino of the first complex can be 35 bp in length and the one or more morpholinos of the second complex can be 35 bp in length. In an aspect, the morpholino of the first complex can be 5' CCT GAT ACA GAA GTA GAA AGC AGT CAC GCA ATA TA 3' (SEQ ID NO:9) and the one or more morpholinos of the second complex can be 5' TAT ATT GCG TGA CTG CTT TCT ACT TCT GTA TCA GG 3' (SEQ ID NO:10). In an aspect, the morpholino of the first complex can be 5' GAA CAA CGA GAG GTG CTC AAT ACA GAT ATC AAT CA 3' (SEQ ID NO:11) and the one or more morpholinos of the second complex can be 5' TGA TTG ATA TCT GTA TTG AGC ACC TCT CGT TGT TC 3' (SEQ ID NO:12).

In an aspect of a disclosed method of treatment, the morpholino of the first complex can be 32 bp in length and the one or more morpholinos of the second complex can be 32 bp in length. In an aspect, the morpholino of the first complex can be 5' AGT CAT AGA TAG ACA GAA TAG CCG GAT AAA CT 3' (SEQ ID NO:13) and the one or more morpholinos of the second complex can be 5' AGT TTA TCC GGC TAT TCT GTC TAT CTA TGA CT 3' (SEQ ID NO:14). In an aspect, the morpholino of the first complex can be 5' GAT ACA GAA GTA GAA AGC AGT CAC GCA ATA TA 3' (SEQ ID NO:15) and the one or more morpholinos of the second complex can be 5' TAT ATT GCG TGA CTG CTT TCT ACT TCT GTA TC 3' (SEQ ID NO:16).

In an aspect of a disclosed method of treatment, the morpholino of the first complex can be 30 bp in length and the one or more morpholinos of the second complex can be 30 bp in length. In an aspect, the morpholino of the first complex can be 5' GGC ATA GAT AAC AGA ATA GCC GGA TAA ACT 3' (SEQ ID NO:17) and the one or more morpholinos of the second complex can be 5' AGT TTA TCC GGC TAT TCT GTT ATC TAT GCC 3' (SEQ ID NO:18). In an aspect, the morpholino of the first complex can be 5' GAC CAG TAG ATA AGT GAA CCA GAT TGA ACA 3' (SEQ ID NO:19) and the one or more morpholinos of the second complex can be 5' TGT TCA ATC TGG TTC ACT TAT CTA CTG GTC 3' (SEQ ID NO:20).

In an aspect of a disclosed method of treatment, the morpholino of the first complex can be 28 bp in length and the one or more morpholinos of the second complex can be 28 bp in length. In an aspect, the morpholino of the first complex can be 5' GAG TAC AGC CAG AGA GAG AAT CAA TAT A 3' (SEQ ID NO:21) and the one or more morpholinos of the second complex can be 5' TAT ATT GAT TCT CTC TCT GGC TGT ACT C 3' (SEQ ID NO:22). In an aspect, the morpholino of the first complex can be 5' GTG AAC ACG AAA GAG TGA CGC AAT AAA T 3' (SEQ ID NO:23) and the one or more morpholinos of the second complex can be 5' ATT TAT TGC GTC ACT CTT TCG TGT TCA C 3' (SEQ ID NO:24).

In an aspect of a disclosed method of treatment, the morpholino of the first complex can be 25 bp in length and the one or more morpholinos of the second complex can be 25 bp in length. In an aspect, the morpholino of the first complex can be 5' GAG TAA GCC AAG GAG AAT CAA TAT A 3' (SEQ ID NO:25) and the one or more morpholinos of the second complex can be 5' TAT ATT GAT TCT CCT TGG CTT ACT C 3' (SEQ ID NO:26). In an aspect, the morpholino of the first complex can be 5' AGA TGA CGA TAA AGA CGC AAA GAT T 3' (SEQ ID NO:27) and the one or more morpholinos of the second complex can be 5' AAT CTT TGC GTC TTT ATC GTC ATC T 3' (SEQ ID NO:28). In an aspect, the morpholino of the first complex can comprise 3 cytidines, 6 guanosines, 12 adenosines, and 4 thymidines and the one or more morpholinos of the second complex can comprise 6 cytidines, 3 guanosines, 4 adenosines, and 12 thymidines.

In an aspect of a disclosed method of treatment, the morpholino of the first complex can be 23 bp in length and the one or more morpholinos of the second complex can be 23 bp in length. In an aspect, the morpholino of the first complex can be 5' GGA CCA AGT AAA CAG GGA TAT AT 3' (SEQ ID NO:29) and the one or more morpholinos of the second complex can be 5' ATA TAT CCC TGT TTA CTT GGT CC 3' (SEQ ID NO:30). In an aspect, the morpholino of the first complex can be 5' GCT GAA AAC CAA TAT GAG AGT GA 3' (SEQ ID NO:31) and wherein the one or more morpholinos of the second complex can be 5' TCA CTC TCA TAT TGG TTT TCA GC 3' (SEQ ID NO:32).

In an aspect of a disclosed method of treatment, the morpholino of the first complex can be 20 bp in length and the one or more morpholinos of the second complex can be 20 bp in length. In an aspect, the morpholino of the first complex can be 5' GAT GAA GTA CCG ACA AGA TA 3' (SEQ ID NO:33) and the one or more morpholinos of the second complex can be 5' TAT CTT GTC GGT ACT TCA TC 3' (SEQ ID NO:34). In an aspect, the morpholino of the first complex can be 5' GAC AGG ATG AAT AAC ACA GT 3' (SEQ ID NO:35) and the one or more morpholinos of the second complex can be 5' ACT GTG TTA TTC ATC CTG TC 3' (SEQ ID NO:36).

In an aspect of a disclosed method of treatment, the morpholino of the first complex can be 18 bp in length and the one or more morpholinos of the second complex can be 18 bp in length. In an aspect, the morpholino of the first complex can be 5' GCA GCA AAC GAA GTA TAT 3' (SEQ ID NO:37) and the one or more morpholinos of the second complex can be 5' ATA TAC TTC GTT TGC TGC 3' (SEQ ID NO:38). In an aspect, the morpholino of the first complex can be 5' GTC ATA ACA GAA CAG GTA 3' (SEQ ID NO:39) and the one or more morpholinos of the second complex can be 5' TAC CTG TTC TGT TAT GAC 3' (SEQ ID NO:40).

In an aspect of a disclosed method of treatment, the morpholino of the first complex can be 15 bp in length and the one or more morpholinos of the second complex can be 15 bp in length. In an aspect, the morpholino of the first complex can be 5' TCA AGA CAG AAG GAT 3' (SEQ ID NO:41) and the one or more morpholinos of the second complex can be 5' ATC CTT CTG TCT TGA 3' (SEQ ID NO:42). In an aspect, the morpholino of the first complex can be 5' TAG CAA CAT AGG AAG 3' (SEQ ID NO:43) and the one or more morpholinos of the second complex can be 5' CTT CCT ATG TTG CTA 3' (SEQ ID NO:44).

In an aspect of a disclosed method of treatment, the morpholino of the first complex can be 12 bp in length and the one or more morpholinos of the second complex can be 12 bp in length. In an aspect, the morpholino of the first complex can be 5' CAG AGA GCA TAT 3' (SEQ ID NO:45) and the one or more morpholinos of the second complex can be 5' ATA TGC TCT CTG 3' (SEQ ID NO:46). In an aspect, the morpholino of the first complex can be 5' CAA GAG GTA CAT 3' (SEQ ID NO:47) and the one or more morpholinos of the second complex can be 5' ATG TAC CTC TTG 3' (SEQ ID NO:48).

In an aspect of a disclosed method of treatment, the morpholino of the first complex can be 10 bp in length and the one or more morpholinos of the second complex can be 10 bp in length. In an aspect, the morpholino of the first complex can be 5' AAG AGG TAC A 3' (SEQ ID NO:49) and the one or more morpholinos of the second complex can be 5' TGT ACC TCT T 3' (SEQ ID NO:50). In an aspect, the morpholino of the first complex can be 5' AAG GAC AGT A 3' (SEQ ID NO:51) and the one or more morpholinos of the second complex can be 5' TAC TGT CCT T 3' (SEQ ID NO:52).

D. SYNTHESIS i) Synthesis of Complex Comprising a Targeting Moiety and an Oligonucleotide Disclosed herein are processes of synthesizing a complex comprising a targeting moiety and an oligonucleotide, the process comprising obtaining a targeting moiety, modifying an oligonucleotide, and conjugating the targeting moiety with the oligonucleotide. In an aspect, a targeting moiety can be conjugated to the oligonucleotide via a thioether bond. In an aspect, an oligonucleotide can be SMCC modified. In an aspect, the oligonucleotide can contain a 3'-maleimido group. In an aspect, a disclosed process of synthesizing a complex can comprise introducing a detectable label. In an aspect of a disclosed process of synthesizing a complex, a targeting moiety can be a disclosed targeting moiety. For example, a targeting moiety can be a Fab' fragment specific for CD20. In an aspect of a disclosed process of synthesizing a complex, an oligonucleotide can be a disclosed oligonucleotide. For example, a disclosed oligonucleotide can be a morpholino comprising 10 bp-40 bp.

ii) Synthesis of Complex Comprising a Copolymer Carrier and One or More Oligonucleotides Disclosed herein are processes of synthesizing a complex comprising a copolymer carrier and one or more oligonucleotides, the process comprising: obtaining a copolymer carrier, modifying one or more oligonucleotides, and conjugating the copolymer carrier to one or more oligonucleotides. In an aspect, a copolymer carrier can comprise a main chain and one or more side chains. In an aspect, RAFT polymerization can be used to generate a disclosed main chain. In an aspect, a disclosed process of synthesizing a complex can comprise introducing a detectable label. In an aspect of a disclosed process of synthesizing a complex, a copolymer carrier can be a disclosed copolymer carrier. For example, a disclosed copolymer carrier can comprise HPMA copolymers copolymerized with MA-GG-TT monomers. In an aspect of a disclosed process of synthesizing a complex, one or more oligonucleotides can be one or more disclosed oligonucleotides. For example, one or more disclosed oligonucleotides can be morpholinos each comprising 10 bp-40 bp.

iii) Synthesis of Composition Comprising Complex Comprising a Targeting Moiety and an Oligonucleotide and Complex Comprising a Copolymer Carrier and One or More Oligonucleotides Disclosed herein are processes of synthesizing a complex comprising a targeting moiety and an oligonucleotide and a complex comprising a copolymer carrier and one or more oligonucleotides, the process comprising contacting a first complex comprising a targeting moiety and an oligonucleotide with a second complex comprising a copolymer carrier to one or more oligonucleotides. In an aspect, an oligonucleotide of a first complex hybridizes to the one or more oligonucleotides of a second complex. In an aspect, a disclosed process can comprise generating a first complex. In an aspect, a disclosed process can comprise generating a second complex. In an aspect, a disclosed process can comprise generating a first complex and generating a second complex. In an aspect, a first complex can be any disclosed complex comprising a targeting moiety and an oligonucleotide. In an aspect, a second complex can be any disclosed complex comprising a copolymer carrier and one or more oligonucleotides. For example, in an aspect of a disclosed process, a targeting moiety can be a Fab' fragment specific for CD20, a copolymer carrier can comprise HPMA copolymers copolymerized with MA-GG-TT monomers, and each of the oligonucleotides can be a morpholinos comprising 10 bp-40 bp, wherein the morpholino of the first complex is complementary to the one or more morpholinos of the second complex.

It is contemplated that each disclosed methods can further comprise additional steps, manipulations, and/or components. It is also contemplated that any one or more step, manipulation, and/or component can be optionally omitted. It is understood that a disclosed methods can be used to provide the disclosed compounds. It is also understood that the products of the disclosed methods can be employed in the disclosed methods of using.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention. Efforts have been made to ensure accuracy with respect to numbers (e.g., amounts, temperature, etc.), but some errors and deviations should be accounted for.

i) In Vitro Evaluation a. Design of Morpholinos

A pair of 25 bp complementary morpholinos (MORF1-m=5' GAG TAA GCC AAG GAG AAT CAA TAT A 3' (SEQ ID NO:25) and MORF2-m=5' TAT ATT GAT TCT CCT TGG CTT ACT C 3' (SEQ ID NO:26)) were designed. The morpholinos were modified with a 3' primary amine used for conjugation. (FIG. 2, Gene Tools, LLC (Philomath, Oreg.)). The selection of 25 bp oligonucleotides ensured a strong binding affinity for the subsequent experiments as the Kd of the hybridization between two morpholinos each having 25 bp is typically at the pM level. The sequence composition of each of these two morpholinos was designed to achieve optimal binding efficacy and specificity. Here, the GC content of each morpholino was about 35-65%. To ensure good aqueous solubility, the total G content was less than 36%. To ensure favorable pharmacokinetics by avoiding rapid renal clearance, the total number of C nucleobases was less than 7. After the base composition of each morpholino was determined, a publically accessible, online sequence "scrambler" was used to ensure minimal off-target binding with human and murine mRNA (i.e., the webpage at www-.sirnawizard.com/scrambled.php). Furthermore, a publically accessible, online sequence analysis software was used to ensure minimal self-complementarity (i.e., the webpage at www.basic.northwestern.edu/biotools/oligocalc.html).

b. Synthesis of Fab'-MORF1 Complex

Figure 3A:
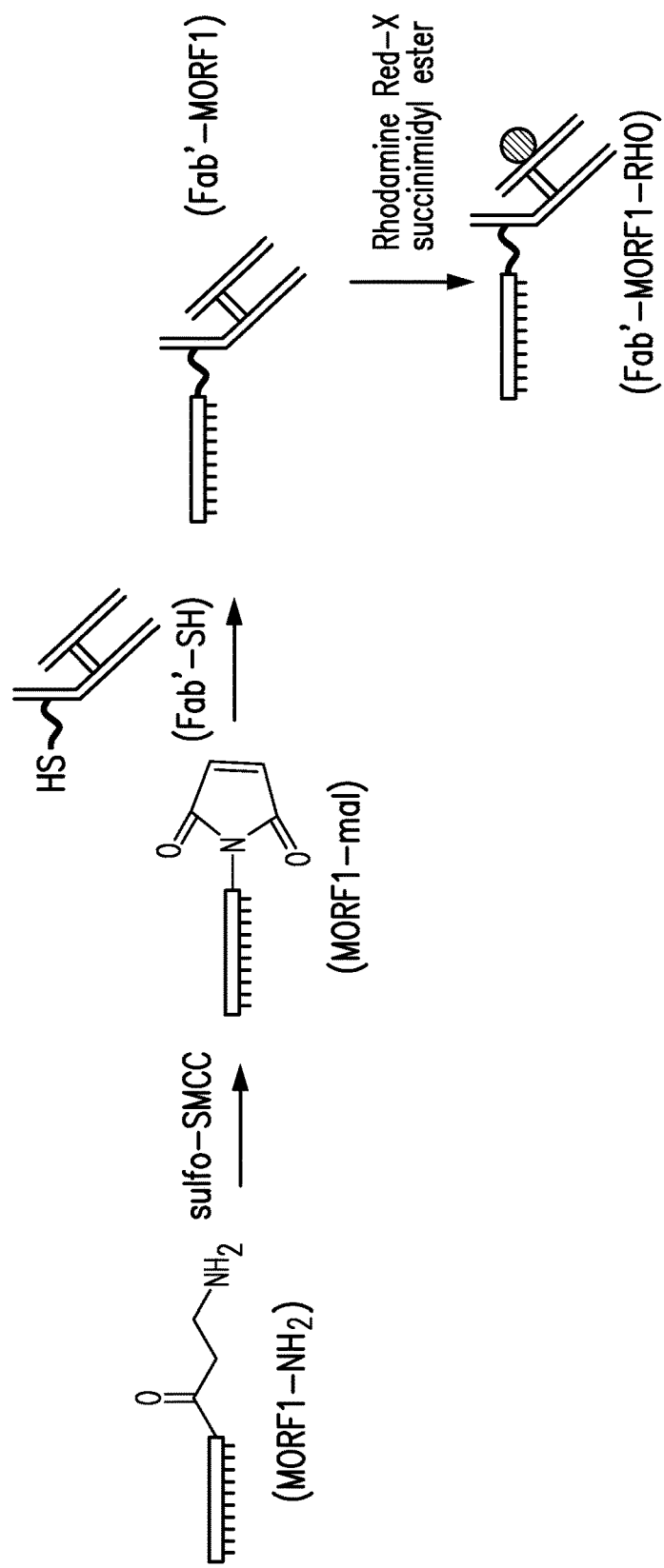
FIG. 3A-FIG. 3B shows the synthesis of a Fab'-MORF1 complex and a Copolymer-MORF2 complex with multiple copies of MORF2.

The murine anti-CD20 IgG antibody (1F5) was prepared from the hybridoma clone 1F5 in a bioreactor (CellMax) and purified on a Protein G column. Antibodies were digested with pepsin to obtain F(ab')$_2$ fragment and further reduced by tris(2-carboxyethyl)phosphine (TCEP) to obtain the Fab' fragment. The Fab' fragment was then conjugated to a succinimidyl-4-(N-maleimidomethyl)cyclohexane-1-carboxylate (SMCC) modified morpholino (i.e., a morpholino with a 3'-maleimide group). Here, the morpholino was represented by SEQ ID NO:25 with a thiol-reactive 3'-maleimido group and the conjugation occurred via a thioether bond. The final product was a Fab'-MORF1 complex. (FIG. 3A). The Fab'-MORF1 complex was labeled with rhodamine for imaging purpose.

c. Synthesis of Copolymer-MORF2 Complex

Figure 3B:
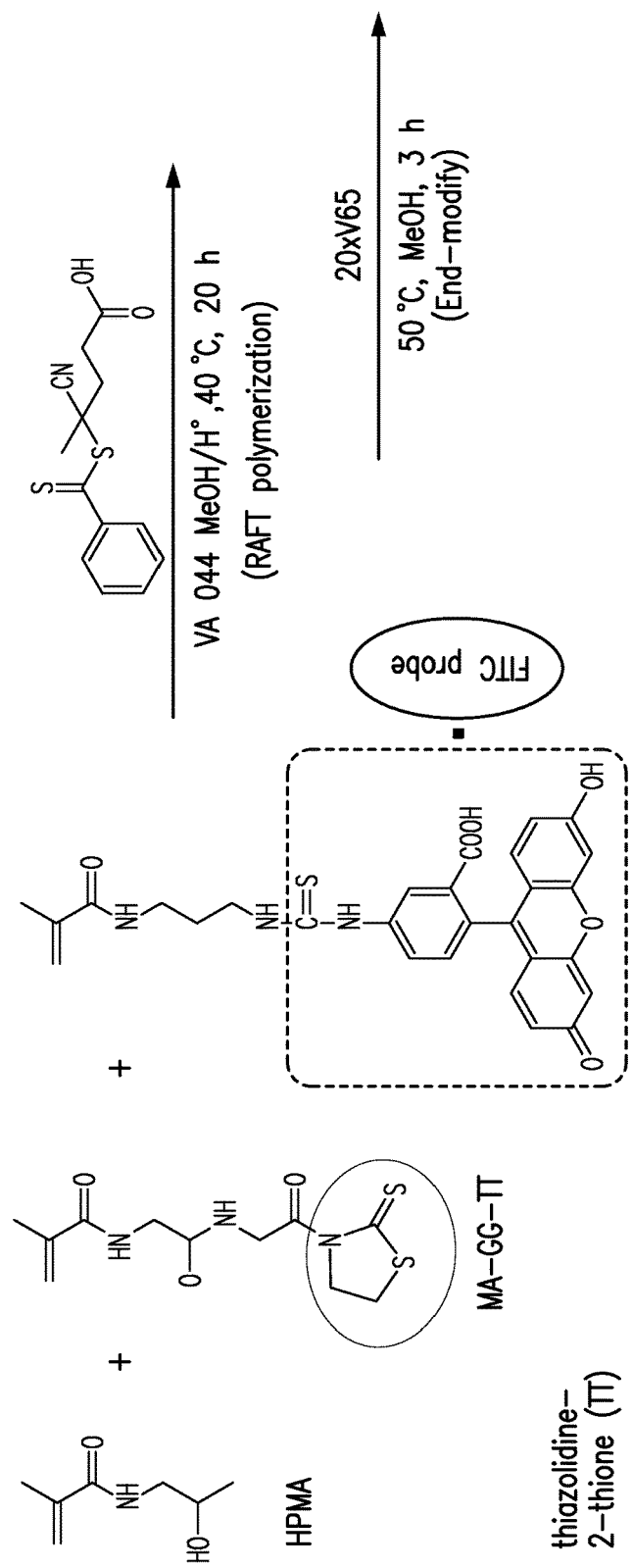
Figure 3B:
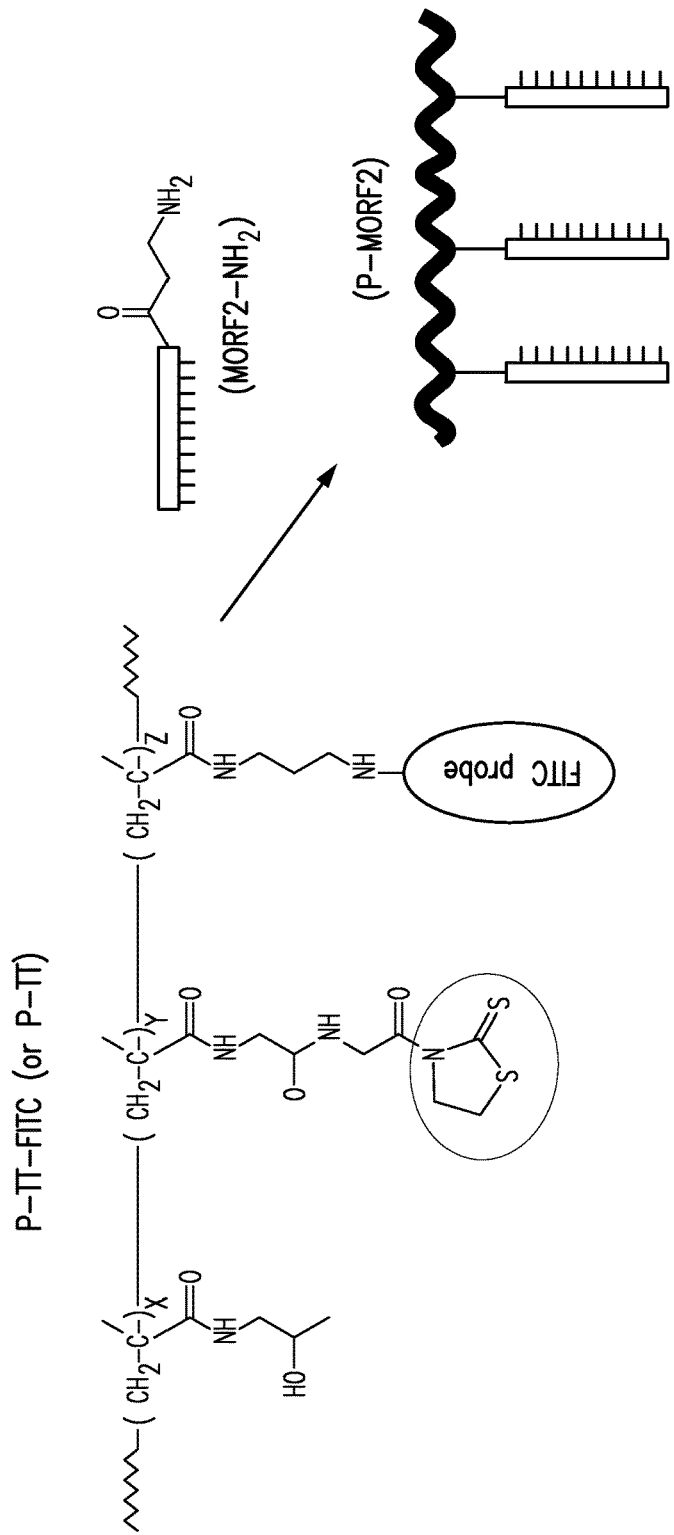

An HPMA copolymer that contained side-chains with amine-reactive thiazolidine-2-thione (TT) groups was synthesized by reversible addition-fragmentation chain transfer (RAFT) polymerization. RAFT polymerization is well known in the art. (FIG. 3B). N-methacryloylglycylglycine-TT (MA-GG-TT) monomer was used to introduce TT via a glycine-glycine spacer. Small amount of co-monomer containing FITC (fluorescein isothiocyanate), which was option, was added for imaging purposes. Using RAFT polymerization, the polymer backbone, which had narrow molecular weight distribution, was reproducibly synthesized. Reaction of the TT groups of the side-chains with the amine-derivatized MORF2 (SEQ ID NO:26) produced an HPMA copolymer grafted with multiple copies of MORF2 via stable amide linkage. The resulting product was a Copolymer-MORF2 complex. Copolymer-MORF2 complexes with differing valences (i.e., the number of morpholinos grafted with the copolymer chain) were synthesized to enable the comparison of the biological effects of these complexes. The Copolymer-MORF2 complex was labeled with FITC for imaging purposes (FIG. 3B).

d. In Vitro Evaluation of Complexes

The in vitro hybridization of the Fab'-MORF1 complex and the Copolymer-MORF2 complex was determined by the following three methods: (1) UV-Vis spectroscopy (hybridization causes a hypochromic effect at absorbance 260 nm upon), (2) SDS-PAGE (hybridization causes gel retardation), and (3) dynamic light scattering (hybridization causes a change of hydrodynamic effective diameter). At the cellular level, human Burkitt's B-cell Non-Hodgkin's Lymphoma Raji cells (ATCC, Bethesda, Md.) were used to study the biorecognition of the Fab'-MORF1 complex and the Copolymer-MORF2 complex. The recognition and binding of the complexes at the cell surface of the Raji cells was determined by confocal fluorescence microscopy. Apoptosis induction was analyzed by using three different measures: (1) caspase-3 activity (i.e., apoptotic gene expression), (2) Annexin V/propidium iodide (PI) binding (i.e., membrane flipping as an early apoptosis event), and (3) terminal deoxynucleotidyl transferase dUTP nick end-labeling (TUNEL) assay (i.e., genomic DNA fragmentation as a late apoptosis event). Throughout these studies, 1F5 mAb hyper-cross-linked with a goat anti-mouse (GAM) secondary Ab was used as a clinically relevant positive control. In addition, human NHL DG-75 B-cells with low or no CD20 expression were used as a negative control cell line.

To evaluate the hybridization of the Fab'-MORF1 complex and the Copolymer-MORF2 complex as well as the direct effect of such hybridization on apoptosis induction, a series of control experiments were performed. Specifically, the following experiments were performed: (1) a single-component treatment with the Fab'-MORF1 complex, (2) single-component treatment with the Copolymer-MORF2 complex, (3) two-component treatment with the Fab'-MORF1 complex plus free copolymer, (4) two-component treatment with the Copolymer-MORF2 complex plus free Fab' fragment, and (5) the "blocking" controls treated with excess (i) free and unconjugated MORF1 and (ii) free and unconjugated MORF2 (e.g., free MORF1 and free MORF2 competed with the binding of the complexes).

Figure 4:
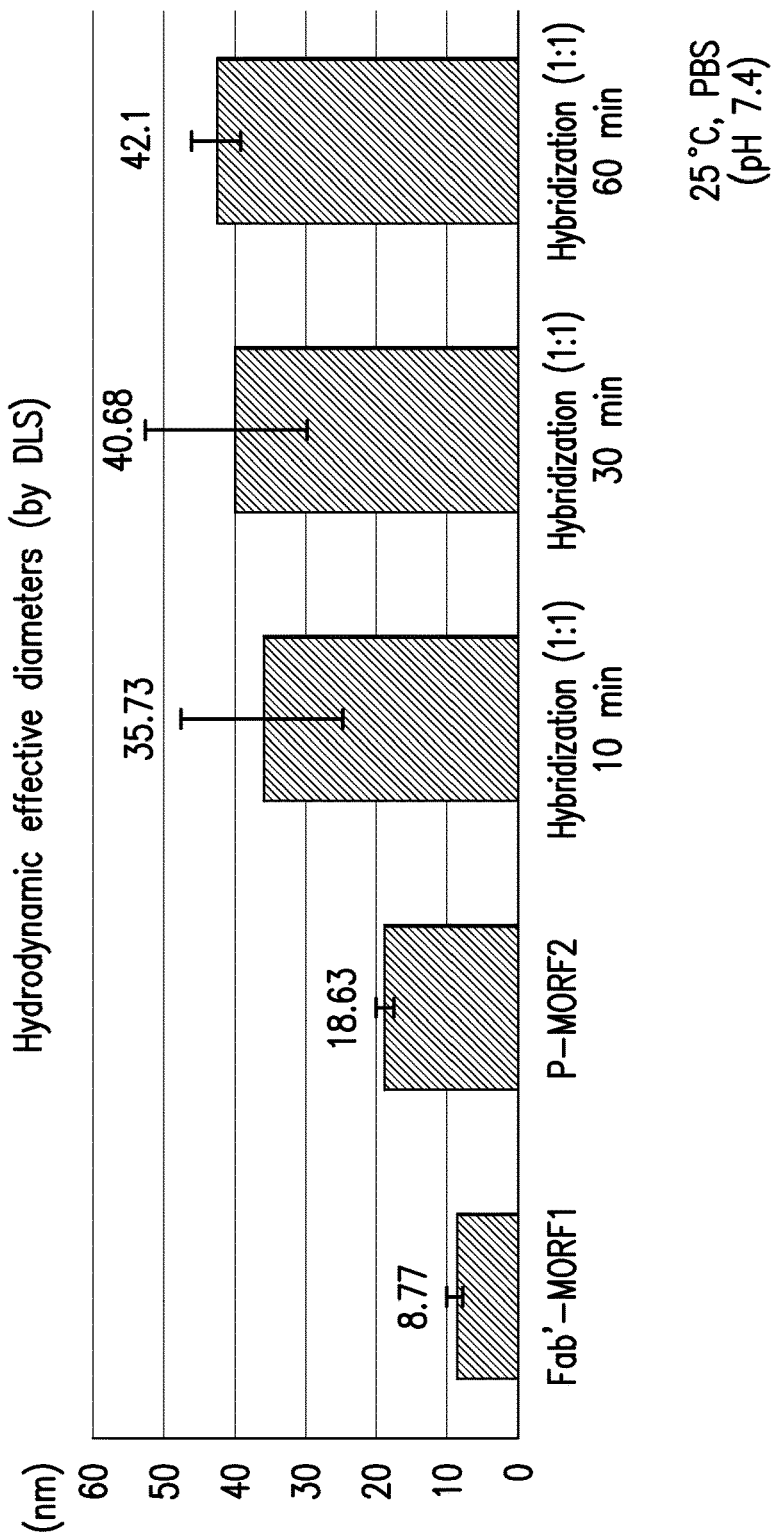
FIG. 4 shows the in vitro hybridization of the Fab'-MORF1 complex with the Copolymer-MORF2 complex as characterized by dynamic light scattering (DLS).

As confirmed by FPLC, HPLC, UV-Vis spectroscopy, and MALDI-ToF mass spectrometry, the Fab'-MORF1 complex and the Copolymer-MORF2 complex were successfully synthesized. The in vitro hybridization of the Fab'-MORF1 complex and the Copolymer-MORF2 complex was confirmed via (1) UV-Vis spectroscopy (hybridization causes a hypochromic effect at 260 nm), (2) SDS-PAGE (hybridization causes gel retardation), and (3) dynamic light scattering (DLS) (FIG. 4). The fast binding kinetics of the hybridization between the Fab-MORF1 complex and the Copolymer-MORF2 complex (~10 min) was demonstrated by the significant and rapid increase of hydrodynamic effective diameters of particles upon mixing the two complexes (as characterized by DLS). In these experiments, hydrodynamic particle sizes of each MORF complex as well as the mixture of the two MORF complexes (molar ratio of MORF1:MORF2 being 1:1) were analyzed. The rapid hybridization (~10 min) of the Fab'-MORF1 complex and the Copolymer-MORF2 complex was reflected by similar particles sizes measured at 10 minutes, 30 minutes, and 60 minutes after mixing. Measurements were triplicated. The hybridization was very fast as compared to the hybridization of the coiled-coil peptide formation (~60 min) (See Wu et al., 2010, showing the self-assembly of an anti-CD20 Fab'-CCE peptide with an HPMA copolymer-CCK peptide).

e. Experimental Results

Figure 5:
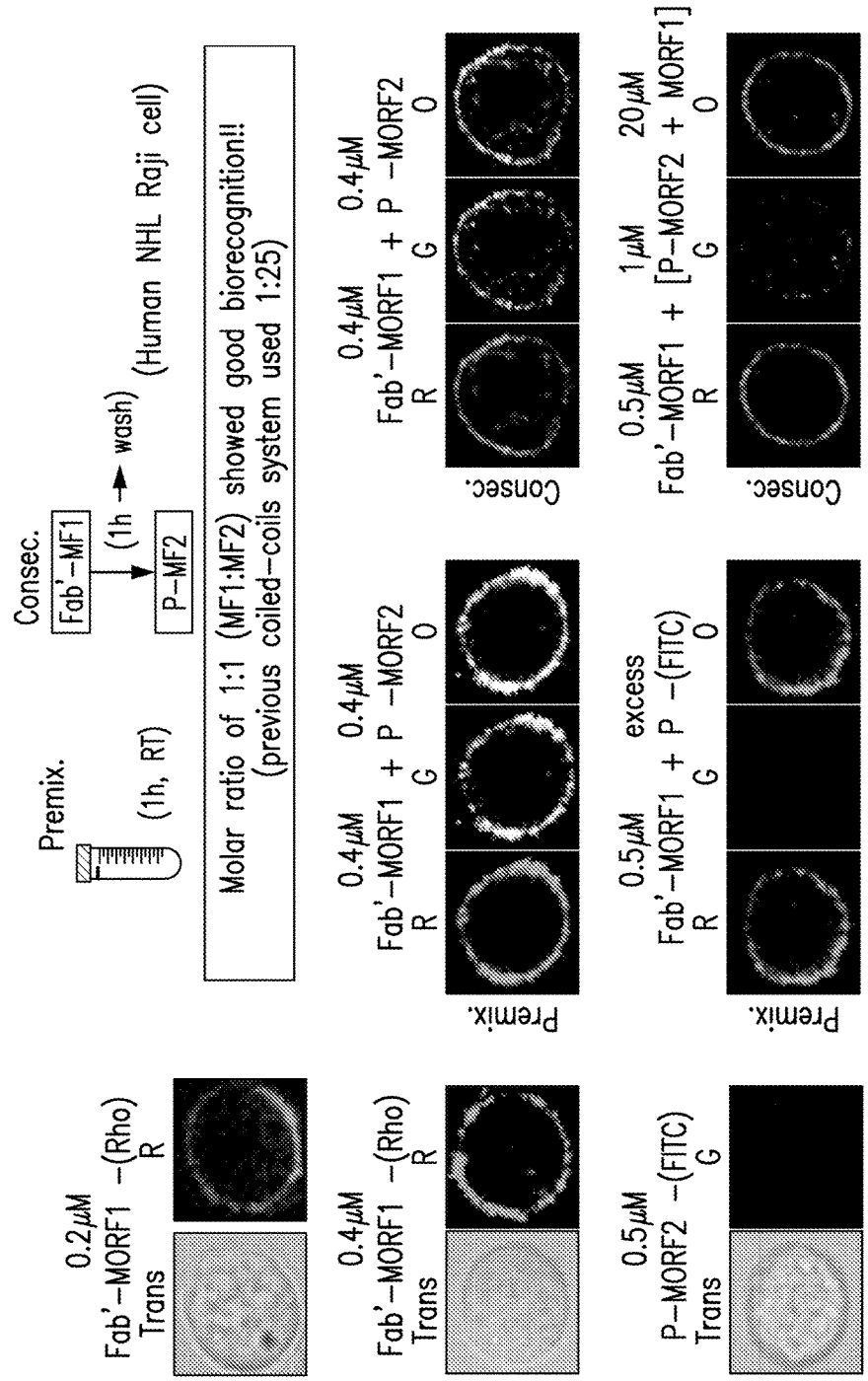
FIG. 5 shows biorecognition of the Fab'-MORF1 complex and the Copolymer-MORF2 complex at the surface of Raji B-cells as analyzed by confocal fluorescence microscopy.

Non-Hodgkin's lymphoma (NHL) is a prevalent cancer worldwide with a high mortality rate. About 85% of NHLs are of B-cell origin, and more than 95% of B-cell lymphomas bear the cell surface antigen CD20. Therefore, the biorecognition of two MORF complexes at cell surface of Raji B-cells (i.e., cells with high CD20 expression) was evaluated by confocal fluorescent microscopy (FIG. 5). In FIG. 5, the following abbreviations apply: Trans—cell images acquired under transmitted light; R—red channel; G—green channel; O—overlay of R and G. The exposure of the B-cells to the Fab'-MORF1 complex (labeled with rhodamine) resulted in the "decoration" of the surface of the B cell with the Fab'-MORF1 complex via the binding of the Fab'-MORF1 complex to CD20 (as indicated by the red signal). Cells exposed to the Copolymer-MORF2 complex (labeled with FITC) did not show any observable fluorescence signal, which was expected due to the absence of a biorecognition pair. However, when both complexes were used (Fab'-MORF1 complex and Copolymer-MORF2 complex), both treatment protocols (i.e., treatment with simultaneous exposure of both complexes ("premixed") or treatment with consecutive exposure to each complex) led to co-localization of both complexes at the B-cell surface and therefore led to the hybridization of the Fab'-MORF1 complex and the Copolymer-MORF2 complex (shown in yellow fluorescence). This hybridization is indicated by the overlay of fluorescent signals on the surface of the B-cell.

The simultaneous or premixed treatment protocol appeared to generate a stronger fluorescent signal at the cell surface, which is the result of the multivalency of the premixed complexes possessing higher binding affinities. In control experiments, the premixture of the Fab'-MORF1 complex and free polymer labeled with FITC (i.e., no Copolymer-MORF2 complex) resulted in only red signal at the B-cell surface. Similarly, in control experiments, the premixture of the Fab'-MORF1 complex and an excess of free, unconjugated MORF1 resulted in only red signal at B-cell surface. These results confirmed that the hybridization of the MORF1 complex with the MORF2 complex conferred excellent biorecognition.

The efficacy of the hybridization between the two MORF complexes was proven to be much better than that of other molecules (e.g., coiled-coil peptides). For example, a molar ratio of 1:1 (MORF1:MORF2) was applied. In contrast to the excellent hybridization efficacy and biorecognition provided by the compositions and methods disclosed herein, the coiled-coil peptides required a 25× excess of the second peptide to achieve observable biorecognition. These experiments demonstrated that there was better accessibility of morpholinos on the copolymer chain than there was with the coiled-coil peptides. The improved accessibility of the morpholinos coupled with the faster binding kinetics (as demonstrated by the DLS results in FIG. 4), indicate that the presently disclosed compositions comprising morpholinos are advantageous with respect to apoptosis induction and in vivo therapeutic efficacy.

Figure 6A:
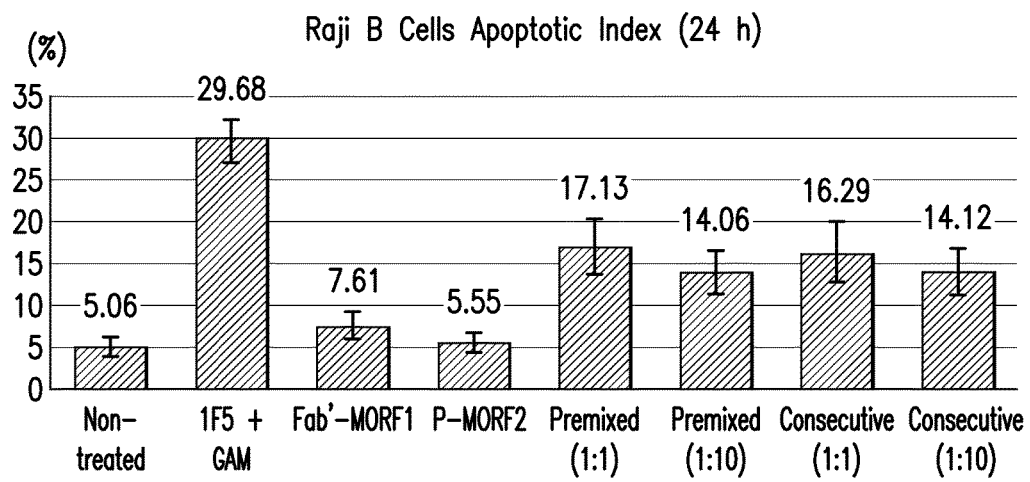
FIG. 6A-FIG. 6C shows apoptosis induction of Raji B-cells utilizing the Fab'-MORF1 complex and the Copolymer-MORF2 complex as analyzed by three methods.
Figure 6B:
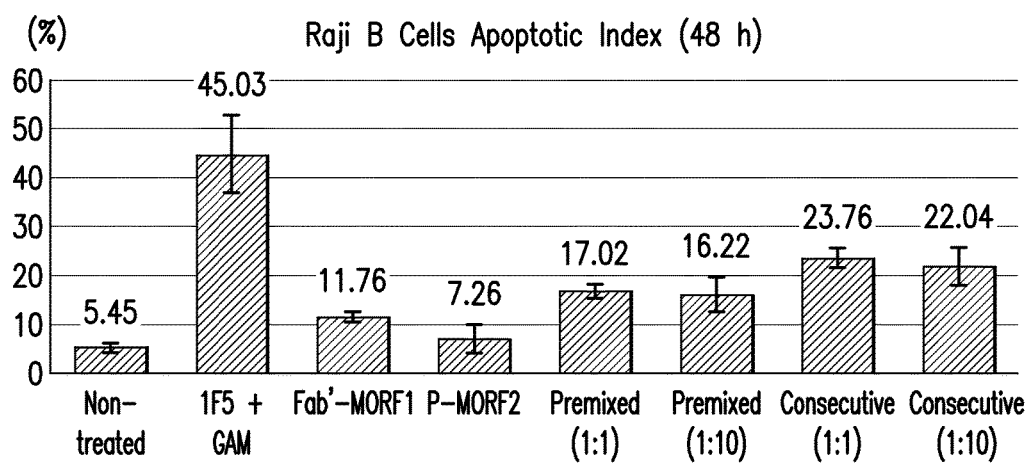
Figure 6C:
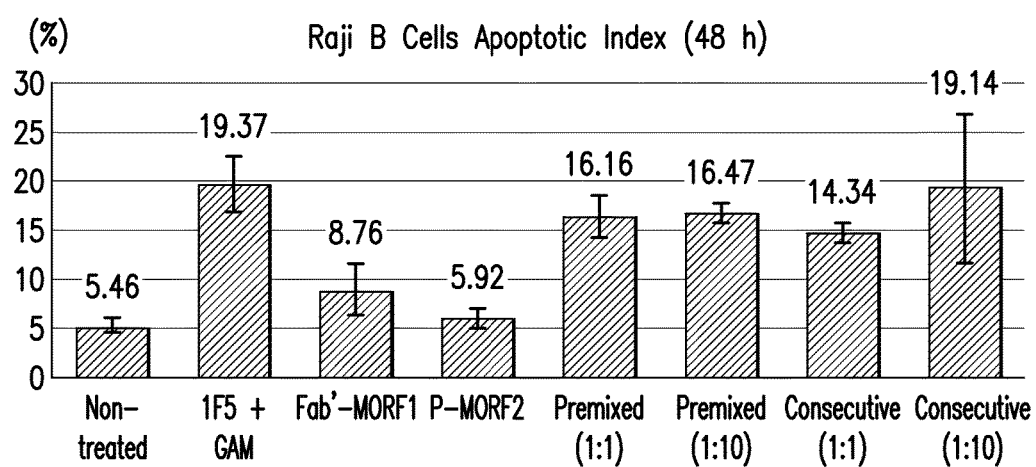

The induction of apoptosis of Raji B-cells following treatment with the disclosed complexes comprising morpholinos was confirmed by three distinct methods: (A) Caspase-3 activation, (B) Annexin V/Propidium Iodide (PI) binding, and (C) TUNEL assay. (FIGS. 6A-FIG. 6C). Treatment with both complexes (Fab'-MORF1 complex and Copolymer-MORF2 complex), either administered consecutively or administered as a premixture, induced detectable cell apoptosis. The level of apoptosis induction in the control groups (i.e., both single-treatment groups (Fab'-MORF1 complex alone or Copolymer-MORF2 complex alone) were not statistically different from that of the non-treated cells. When the molar ratio of MORF1:MORF2 was 1:10, the levels of apoptosis induction were not distinguishable from those groups using 1:1 as the molar ratio of MORF1:MORF2. These data indicate a potential saturation of MORF1 binding sites on the cell surface. These data also confirmed the excellent accessibility of morpholinos on the copolymer chain. For the experiments shown in FIG. 6A-FIG. 6C, 0.5 μM of the two different morpholino complexes or 1F5 mAb were used to treat $2\times10^5$ cells/0.4 mL (for caspase-3 (FIG. 6A) and Annexin V/PI assays (FIG. 6B)) or $10^6$ cells/0.5 mL (for TUNEL assay (FIG. 6C)). All experiments were triplicated.

Table 3 shows the side-by-side comparison of apoptosis induction between the presently disclosed morpholino complexes and coiled-coil peptides. In these experiments, the apoptotic index (%) of human NHL Raji B-cells was assessed under identical cell number and concentration ($2\times10^5$ cells in 400 μL of culture medium). The molar ratio between two components are both 1:1 (CCE:CCK or MORF1:MORF2). The molecular weight of the polymer backbones is also very similar (~100 kDa). These data indicate that the morpholino based compositions and methods (which were tested under lower concentration or lower valence of the polymer conjugates) induced higher levels of apoptosis when compared to the coiled-coil peptide system. The data were observed in both of the treatment protocols (i.e., wherein complexes are consecutively administered or wherein complexes are administered as a premixed composition).

TABLE 3

Comparison of Apoptosis Induction

| | Coiled-Coil Peptides | MORF1-MORF2 Hybridization | |
|---|---|---|---|
| Consecutive | (1 μM, valence = 10) 12% | (1 μM, valence = 3) 37% | (0.5 μM, valence = 10) 50% |
| Premixed | (1 μM, valence = 10) 16% | (1 μM, valence = 3) 39% | (0.5 μM, valence = 10) 43% |

In Table 3, the apoptotic index (%) was assessed by Annexin V/PI binding assay and was quantified by flow cytometry. The two systems were compared at the time intervals corresponding to maximum apoptosis (i.e., 12 hours for coiled-coil peptides (CCE-CCK) and 48 hours for MORF1-MORF2 hybridization). The molar concentration of Fab' (CCE- or MORF1-equivalent) and the valence of the polymer conjugates (# CCK or # MORF2/chain) are listed.

Figure 7:
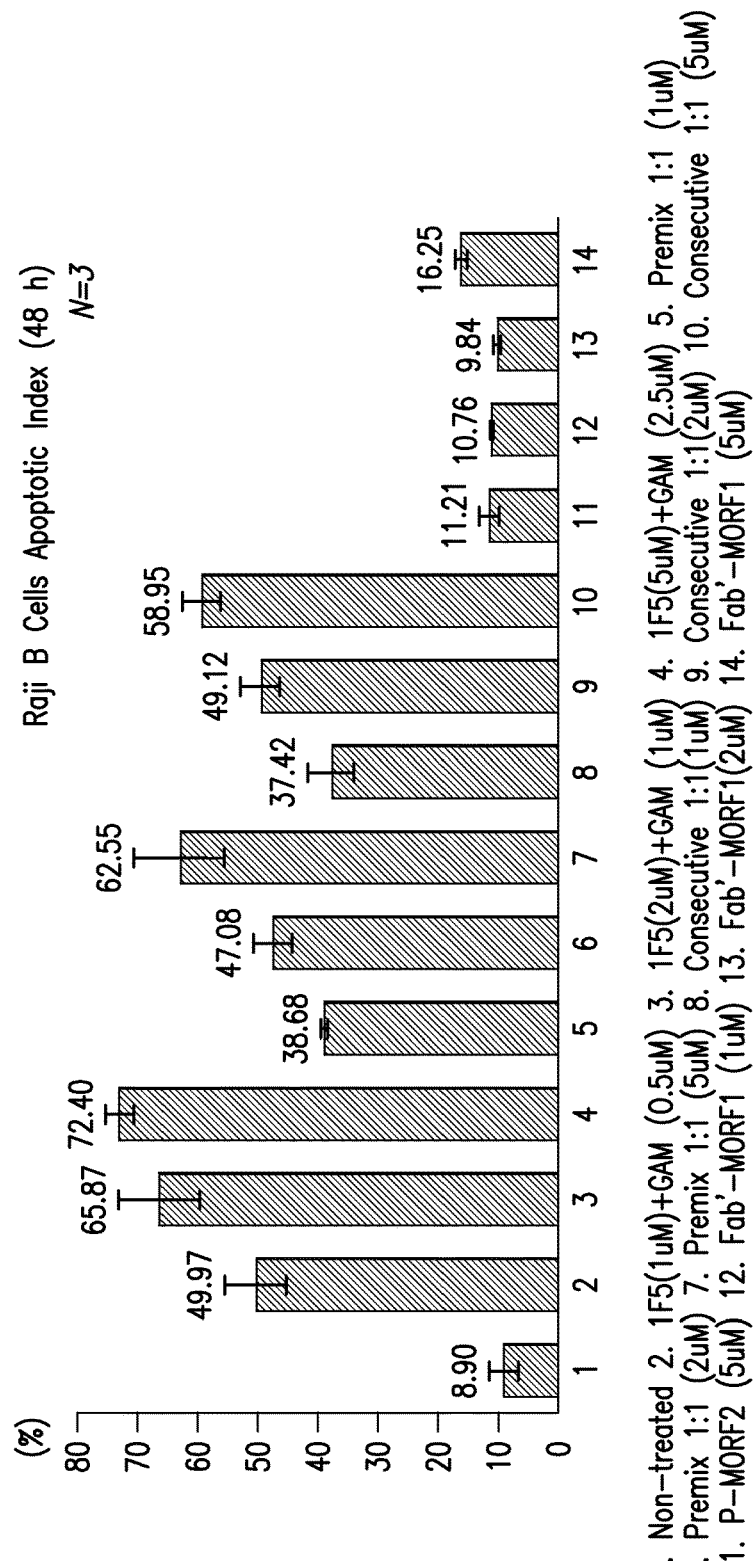
FIG. 7 shows concentration-dependent apoptosis induction of Raji B-cells analyzed by Annexin V/Propidium Iodide (PI) binding assay.

As shown in FIG. 7, increasing the concentrations of the complexes (from 0.5 μM in FIG. 6 to 1 μM, 2 μM, and 5 μM) resulted in the induction of high levels of apoptosis (FIG. 7). The dose-dependent level of apoptosis induction was observed in both treatment protocols (i.e., two complexes were administered as premixed composition or two complexes were administered consecutively) as well as the positive control (1F5 mAb+goat anti-mouse secondary antibody). When the concentration was increased from 2 to 5 μM, the apoptotic index of positive control cells began to saturate. However, saturation was not observed in treatment protocols utilizing the hybridization of the Fab'-MORF1 complex and Copolymer-MORF2 complex. In FIG. 7, morpholino complexes or 1F5 mAb at a concentration of 1 μM, 2 μM, or 5 μM were used to treat $2 \times 10^5$ cells in 0.4 mL medium. The incubation time was 48 hours and analysis occurred via flow cytometry.

Figure 8A:
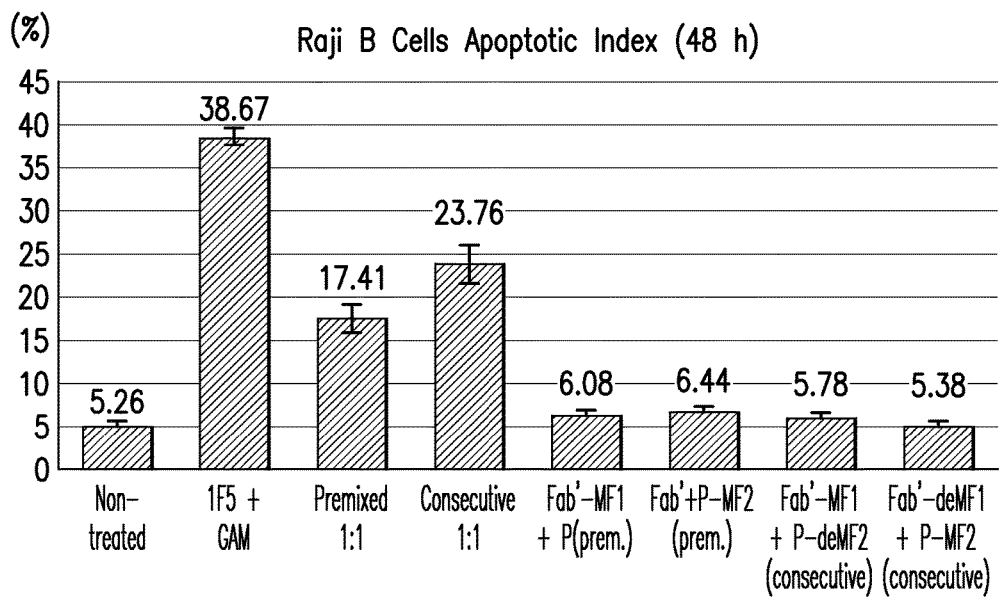
FIG. 8A-FIG. 8B shows Annexin V/propidium iodide binding assay control studies in Raji B-cells (CD20$^+$) and DG-75 cells (CD20$^-$).
Figure 8B:
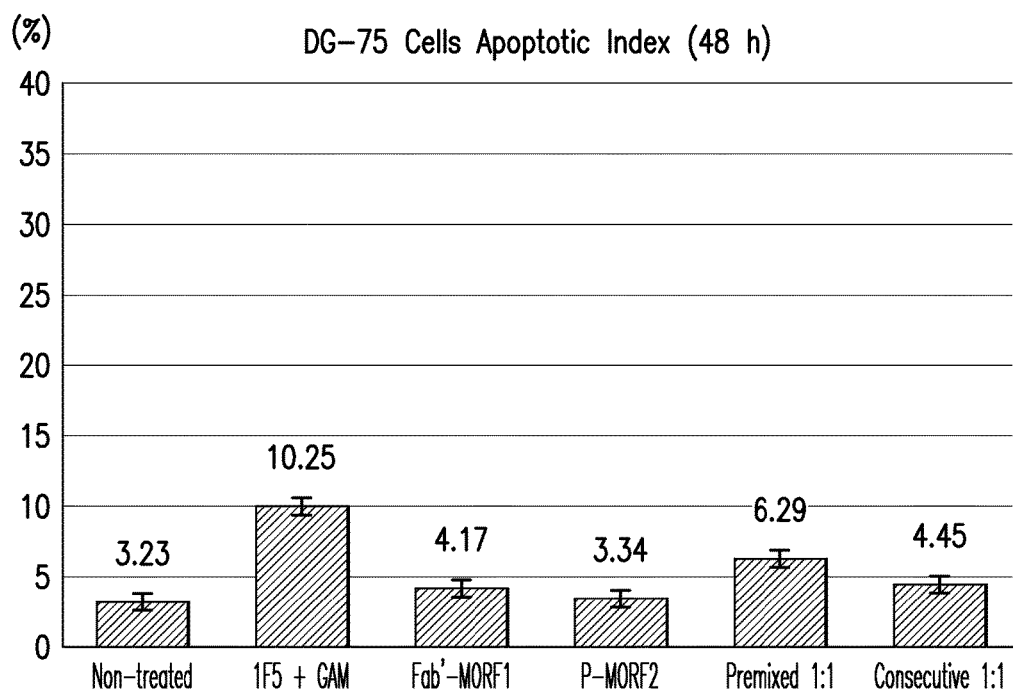

FIG. 8A-FIG. 8B shows results of several control experiments. The treatment protocol utilizing either (i) premixed Fab'-MORF1 complex with free copolymer (i.e., lacking MORF2) or (ii) premixed Copolymer-MORF2 complex with free Fab' fragment (i.e., lacking MORF1) both resulted in similar apoptotic indices when compared to the apoptotic indices of the non-treated cells. Protocols utilizing consecutively treated "blocking" control groups (i.e., complex premixed with excess free MORF1 or excess free MORF2 to compete with the binding sites for hybridization) also produced no observable apoptosis induction. These results proved that the hybridization of MORF1-MORF2 was required for apoptosis induction. Finally, as a negative control (FIG. 8B), the NHL B-cell line DG-75, which lacks cell surface CD20 expression, was used and analyzed with the Annexin V/propidium iodide assay. DG-75 cell exposure resulted in very low apoptotic induction or no apoptosis induction. This result demonstrated that in vitro efficacy of the disclosed morpholino based approach was mediated by CD20 crosslinking. In FIG. 8A-FIG. 8B, P-deMF2 indicates Copolymer-MORF2 complex premixed with free MORF1 (20× excess, 1 hour at room temperature and Fab'-deMF1 indicates Fab'-MORF1 complex premixed with free MORF2 (20× excess, 1 hour at room temperature).

ii) In Vivo Evaluation a. In Vivo Experiment #1

To provide an animal model of advanced NHL, female SCID (C.B-17) mice can be intravenously transplanted with Raji B-cells. This model represents dissemination, infiltration, and growth of malignant (NHL) B-cells in various organs, especially spinal cord and bone marrow. The subject develops hind-limb paralysis and death. Thus, the amount of time that lapses after the subject receives treatment with a disclosed composition or a disclosed complex and the onset of hind-limb paralysis can be determined Here, the amount of time that elapses following treatment and prior to the onset of paralysis can be used as an indicator of therapeutic efficacy.

The immunogenicities of the Fab'-MORF1 complex and the Copolymer-MORF2 complex can be evaluated in immunocompetent (e.g., Balb/c) mice. Enzyme-linked immunosorbent assay (ELISA) can detect early cytokine release (e.g., IFNα, TNFα) in the blood of mice upon i.v.-injection of the conjugates, and can detect long-term antibody production in the blood and spleen of immunized Balb/c mice.

b. In Vivo Experiment #2

Hybrid nanomaterials composed of synthetic and biological building blocks possess high potential for the design of nanomedicines. A therapeutic platform that mimics the mechanism of immune effector cells to crosslink surface receptors of target cells and induce apoptosis was designed. This platform was tested against B-cell lymphomas that highly express the surface antigen CD20. Two nanoconjugates were synthesized: (1) an anti-CD20 Fab' fragment covalently linked to a single-stranded morpholino oligonucleotide (MORF1), and (2) a linear polymer of N-(2-hydroxypropyl)methacrylamide (HPMA) grafted with multiple copies of the complementary oligonucleotide MORF2. The two conjugates self-assembled via MORF1-MORF2 hybridization at the surface of $CD20^+$ malignant B-cells, which cross-linked CD20 antigens and initiated apoptosis. When tested in a murine model of human non-Hodgkin's lymphoma, the two conjugates, either administered consecutively or as a premixture, eradicated cancer cells and produced long-term survivors. The experiment described herein demonstrate that the disclosed methods and disclosed compositions and complexes contained no small-molecule cytotoxic compounds and was immune-independent.

Molecular biorecognition is a fundamental feature of life—many biological processes are governed by the complex yet specific interactions between macromolecules, e.g., antibody-antigen binding and DNA base pairing. These high-fidelity recognition motifs from nature can be employed to design self-assembling nanobiomaterials for applications in drug delivery (Douglas et al., 2012; Mulvey et al., 2013; Lu et al., 1999), tissue engineering (Gungormus et al., 2010; Holmes et al., 2000), bio-detection (Yuan et al., 2008; Ehrick et al. 2005; Liu et al., 2006), etc. A new direction of research is to use such precisely defined "smart" materials to incite or control cellular activities (Wu et al., 2010; Cho et al., 2012; Kopecek et al., 2012) As described herein, the use of the materials alone, without any conventional drug, provided therapeutic effects.

Non-Hodgkin's lymphoma (NHL) is a prevalent cancer worldwide with a high mortality rate (Siegel et al., 2013). Conventional chemotherapy and radiotherapy are accompanied by significant adverse reactions, particularly cytopenias leading to increased risk of infection and need for transfusions. Because most NHLs are of B-cell origin, immunotherapies using monoclonal antibodies (mAbs) targeted to the B-cell surface antigen CD20 have become common treatments (Cheson et al., 2008). However, large populations of patients exist who are not responsive to immunotherapies, especially in the relapse setting. For example, rituximab, the most commonly used anti-CD20 mAb, has a less than 50% overall response rate for relapsed/refractory NHL (Molina et al., 2008). This is largely attributed to the inactivity of immune effector cells to hyper-crosslink ligated mAbs (Cartron et al., 2002; Smith et al., 2003). Moreover, mAb treatments cause rare but lethal side effects such as progressive multifocal leukoencephalopathy (Allison 2010) and lung injuries (Lands 2010; Kamei et al., 2010), which are due to Fc-mediated effector cellular events (e.g. complement activation) (van der Kolk, et al., 2001).

Figure 9:
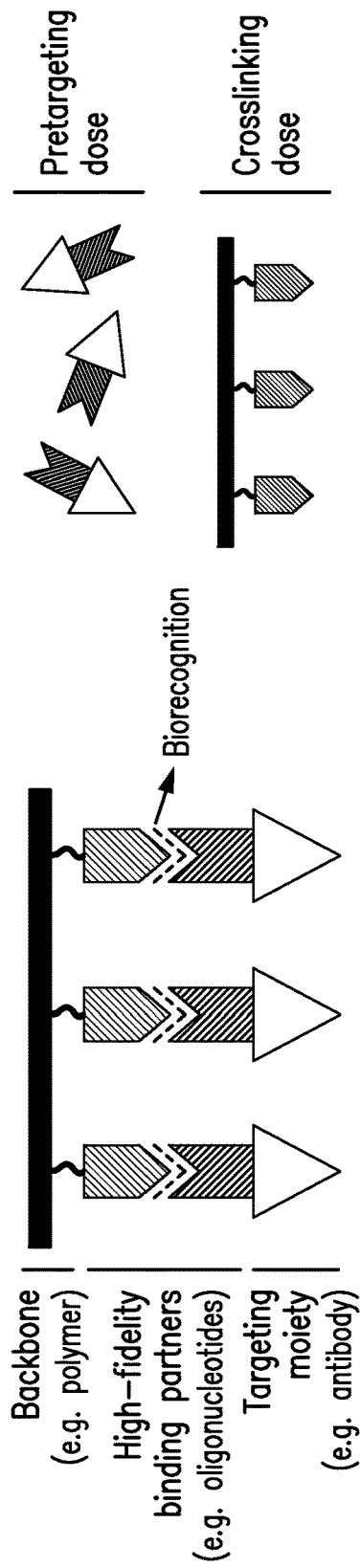
FIG. 9 shows a schematic of self-assembling hybrid nanoconjugates for apoptosis induction.

A biomimetic material platform composed of self-assembling hybrid nanoconjugates (FIG. 9) was designed as a therapeutic system against B-cell lymphomas (FIG. 1). It comprised an anti-CD20 Fab' antibody fragment, a pair of complementary phosphorodiamidate morpholino oligomers (MORF1 and MORF2), and a linear polymer (P) of N-(2-hydroxypropyl)methacrylamide (HPMA). The experiments described herein demonstrate that (1) the exposure of malignant $CD20^+$ B-cells to the conjugate of anti-CD20 Fab' and MORF1 (Fab'-MORF1) decorated the cell surfaces with MORF1; and (2) the further treatment of decorated B-cells with HPMA copolymer grafted with multiple copies of MORF2 (P-MORF2) resulted in MORF1-MORF2 hybridization at the cell surface with concomitant CD20 crosslinking, which triggered apoptosis (FIG. 1). Specifically, FIG. 1 shows apoptosis induction of B-cells by crosslinking of the CD20 antigens that is mediated by extracellular hybridization of complementary morpholino oligonucleotides (MORF1-MORF2). Specifically, FIG. 9 shows a general design concept of the therapeutic platform. Two nanoconjugates that self-assemble via biorecognition can be administered consecutively as pretargeting and crosslinking doses, or premixed to form a multivalent construct and used as a single dose.

When CD20-bound antibodies are hyper-cross-linked by Fc receptor (FcR)-expressing immune effector cells (e.g. macrophages, natural killer cells), CD20 clustering occurs within lipid rafts and induces apoptosis (Deans et al., 2002). Each component (e.g., Fab', morpholino oligo, HPMA polymer) of the disclosed system, when used individually, did not have any pharmacological effect. The apoptosis induction was direct (i.e., independent of immune function) and specific (i.e., targeted to CD20); thereby avoided the side effects and problems of currently used immunotherapy, chemotherapy, and radiotherapy.

The disclosed system is based on a pair of morpholino (MORF) oligonucleotides with complementary sequences. The MORF oligos form double helixes by Watson-Crick base pairing (hybridization) and serve as physical cross linkers. MORF oligos have a charge-neutral phosphorodiamidate backbone resulting in much stronger binding affinity than DNA or RNA (Nielsen 1995). The MORF oligos are biocompatible and nuclease resistant; this ensures in vivo stability and safety (Summerton et al., 1997). Due to these advantages, MORF oligos have been successfully used as macromolecular binders to enhance therapeutic delivery (Mulvey et al., 2013; Liu et al., 2004; Mang'era et al., 2001). The HPMA copolymers described herein are water-soluble and long circulating in the bloodstream. The disclosed copolymers have well-established safety profiles and are used extensively as therapeutic carriers (Kopecek et al., 2010). In aqueous solutions, linear HPMA copolymers have a random coil conformation and are able to effectively present targeting moieties that are grafted to the side chains (Ulbrich et al., 2010).

In the experiments described herein, the development and preclinical evaluation of the proposed anti-lymphoma compositions and complexes (i.e., a nanomedicine) was undertaken. Biorecognition of the two nanoconjugates (Fab'-MORF1 and P-MORF2) was characterized. The therapeutic system was optimized to achieve efficient apoptosis induction of malignant B-cell lines. Excellent anticancer efficacy (100% survival without residual tumors) was demonstrated in a mouse model of human NHL.

To verify the concept of hybridization-mediated drug-free macromolecular therapeutics, CD20 was selected as a pharmacological target. CD20 is a non-internalizing receptor expressed on most NHL malignant B-cells as well as on normal B-cells (Stashenko et al., 1980). However, CD20 is not expressed on plasma cells (effector B-cells) and stem cells. Consequently, humoral immunity of patients is not severely affected and normal numbers of B-cells can be restored after treatment (Anderson et al., 1984; Kimby et al., 2005).[3] Here, an anti-CD20 Fab' fragment was employed in the therapeutic system, which used NHL as a disease model to demonstrate the first example of the disclosed system.

(1) Design of MORF1 and MORF2

Figure 2:
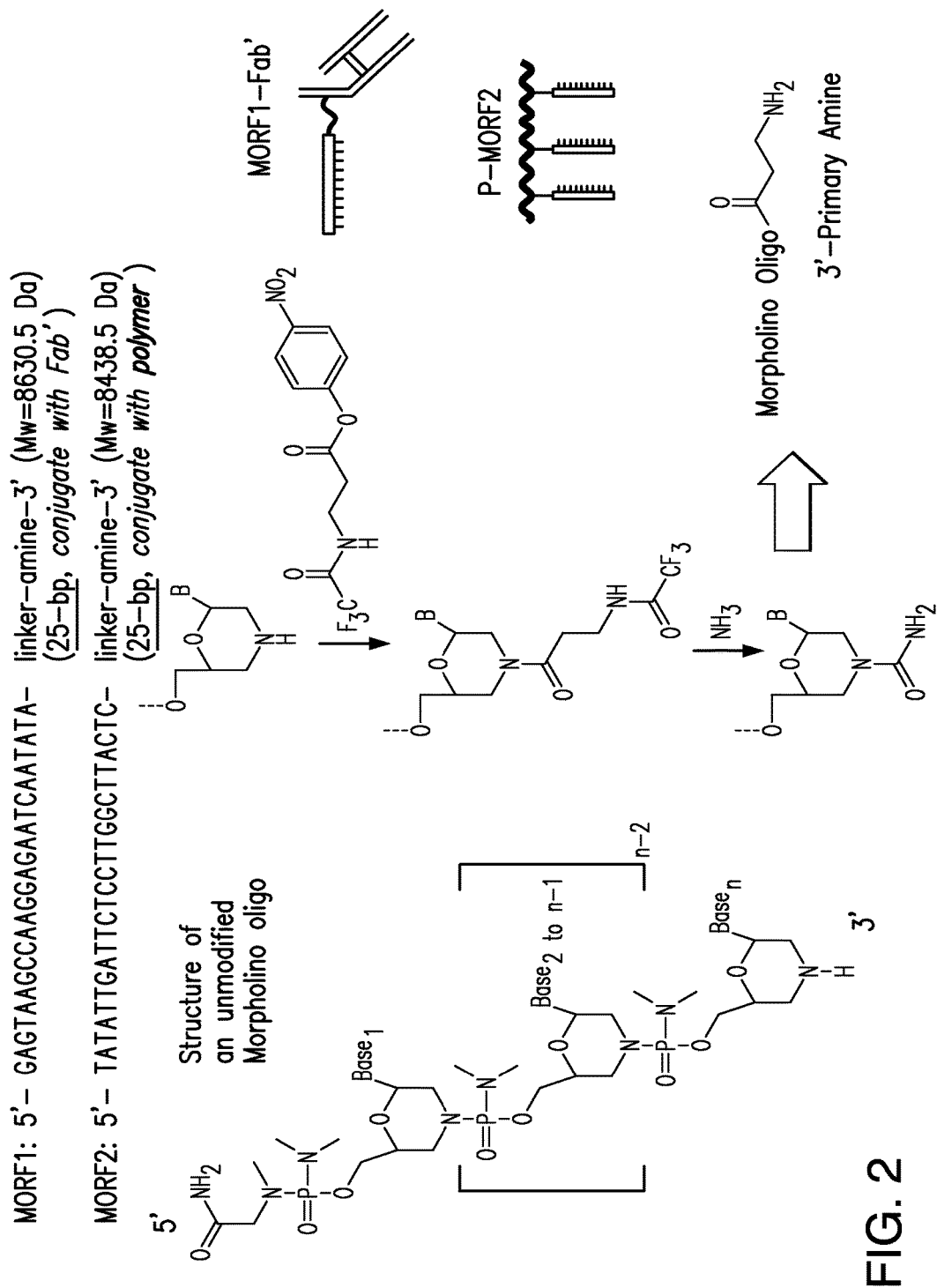
FIG. 2 shows the chemical structure and nucleobase sequences for an exemplary pair of complementary morpholinos—MORF1-m (SEQ ID NO:25) and MORF2-m (SEQ ID NO:26).
Figure 10A:
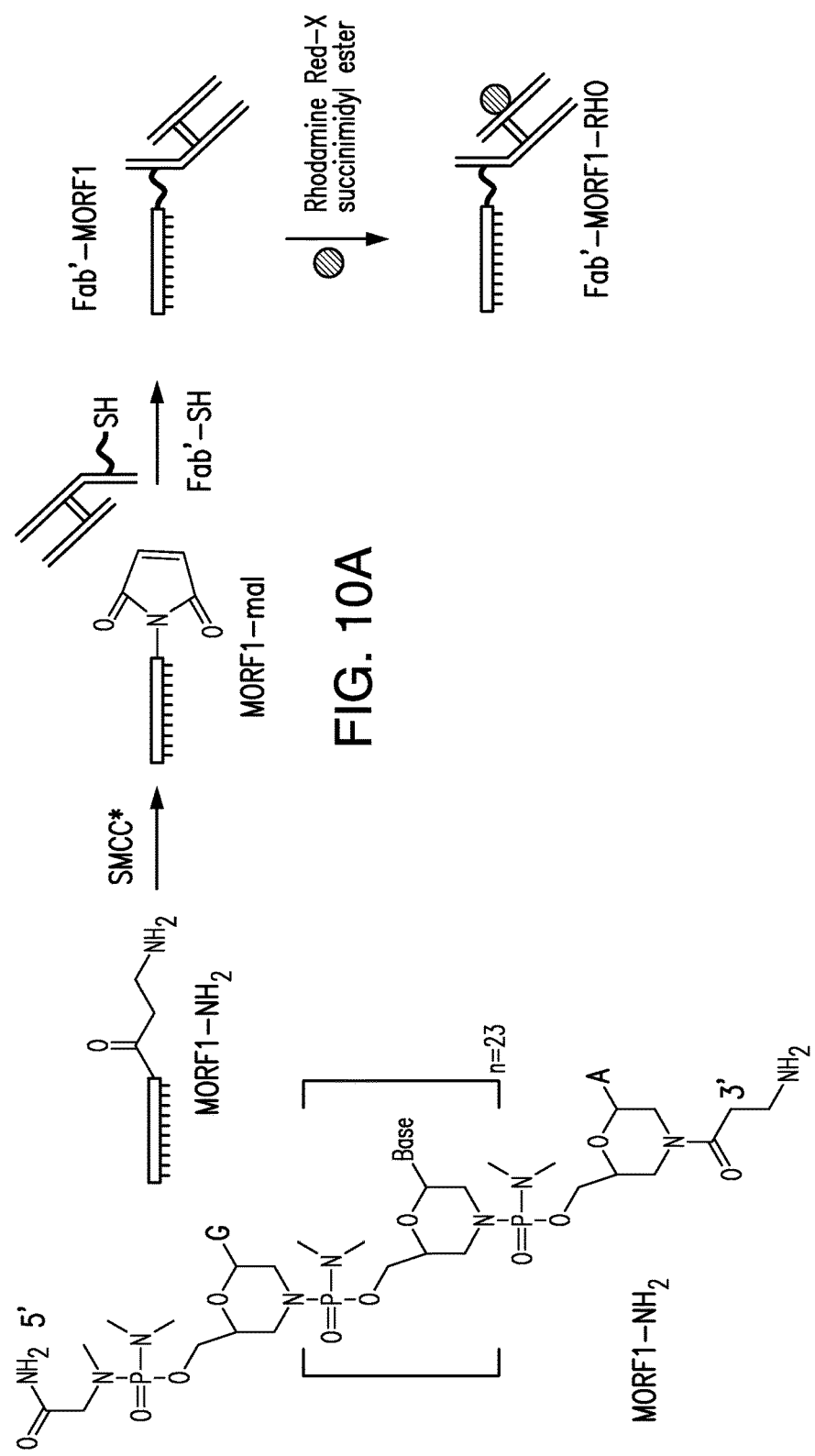
FIG. 10A-FIG. 10D shows synthesis and characterization of Fab'-MORF1 complex and P-MORF2 complex.
Figure 10B:
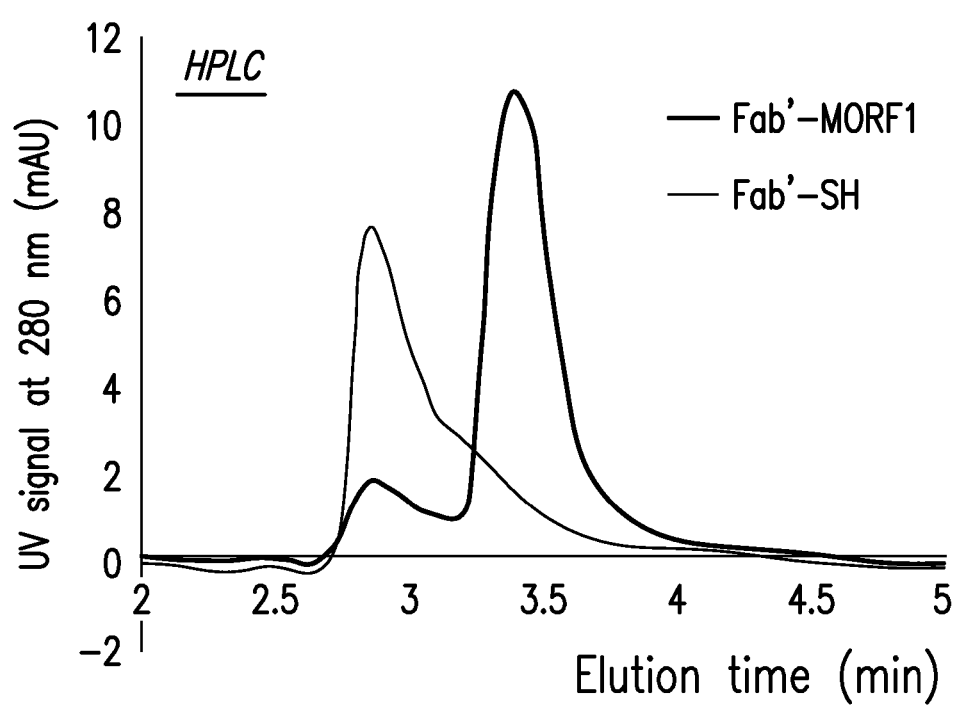
Figure 10C:
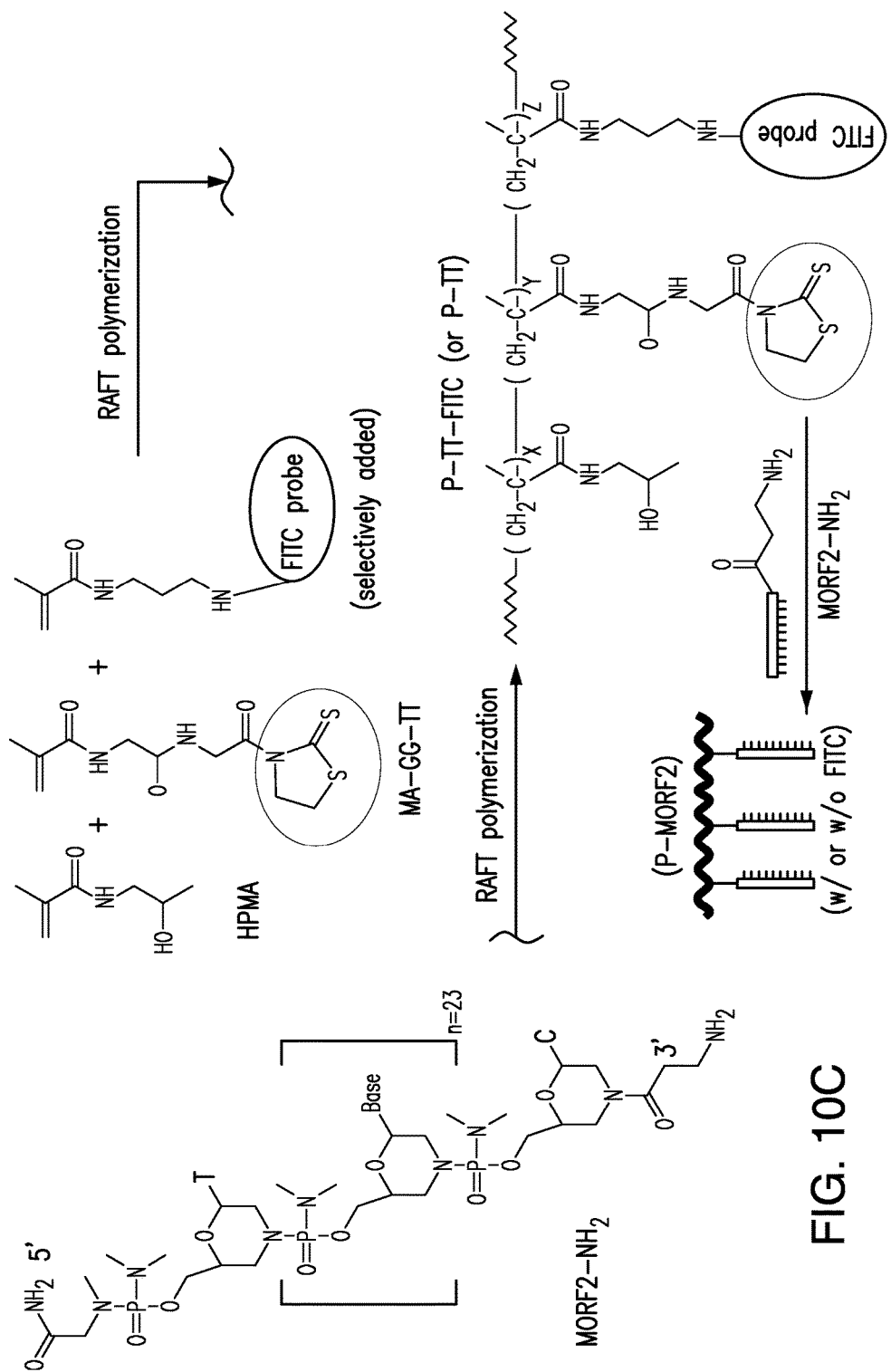

The MORF oligos used were 25 bp and about 8.5 kDa (FIG. 10A, FIG. 10C, and FIG. 2). Their 3' termini were modified with a primary amine used for conjugation. The A/T/C/G content was selected to achieve optimal binding efficacy and specificity (GC=35-65%), maintain aqueous solubility (G<36% (Summerton, et al., 1997)), and provide favorable pharmacokinetics (number of C<7 to avoid rapid kidney uptake (Liu et al., 2004)). After the base composition was determined, the sequences were generated by a scrambling software to minimize off-target binding with human and murine mRNA and further optimized to prevent self-complementarity.

(2) Synthesis and Characterization of Fab'-MORF1 and P-MORF2

Figure 17A:
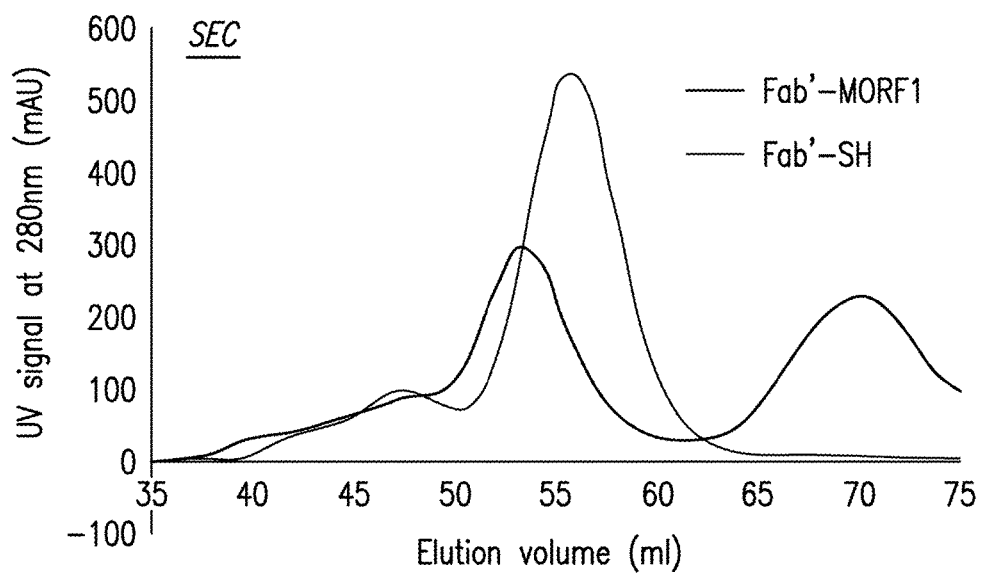
FIG. 17A-FIG. 17E shows the characterization of Fab'-MORF1 complex.
Figure 17B:
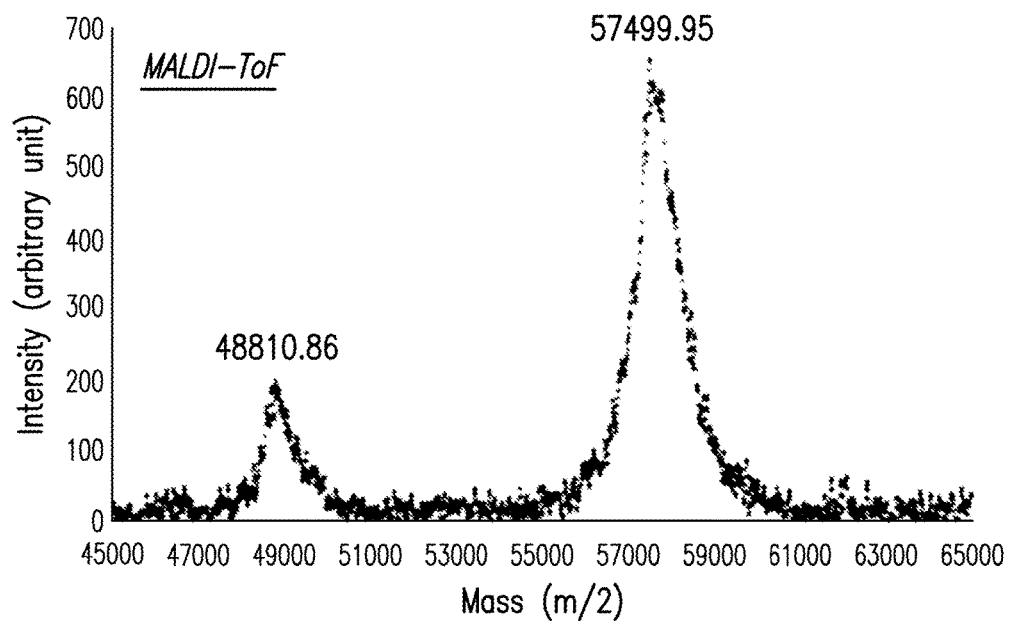
Figure 17C:
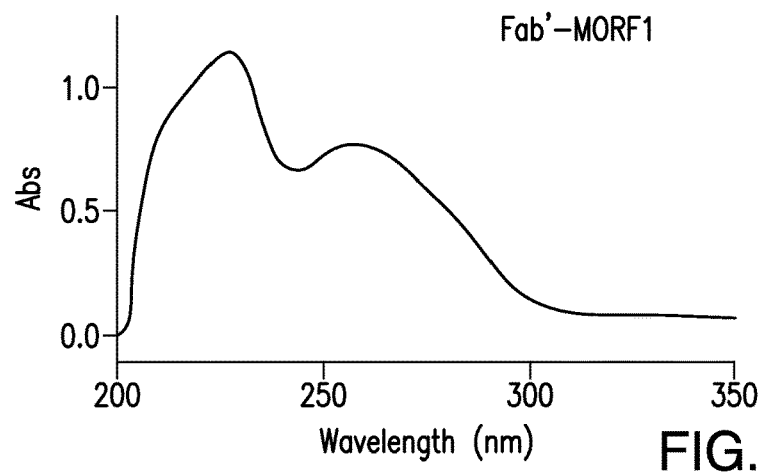
Figure 17D:
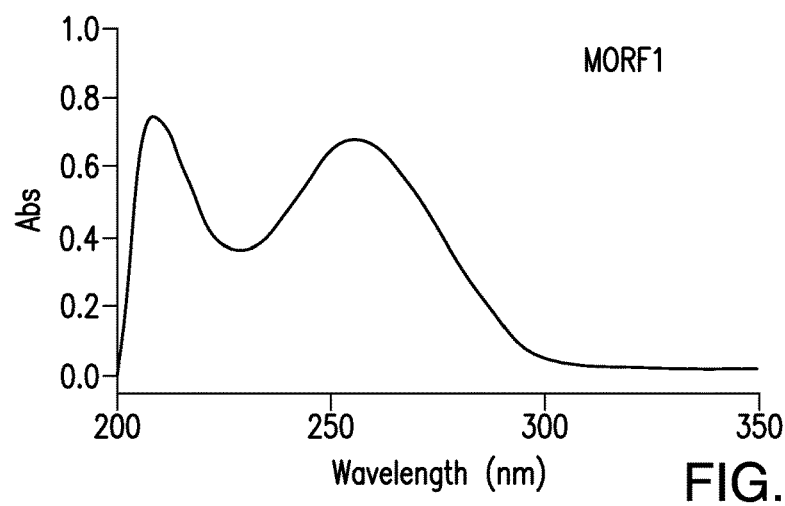
Figure 17E:
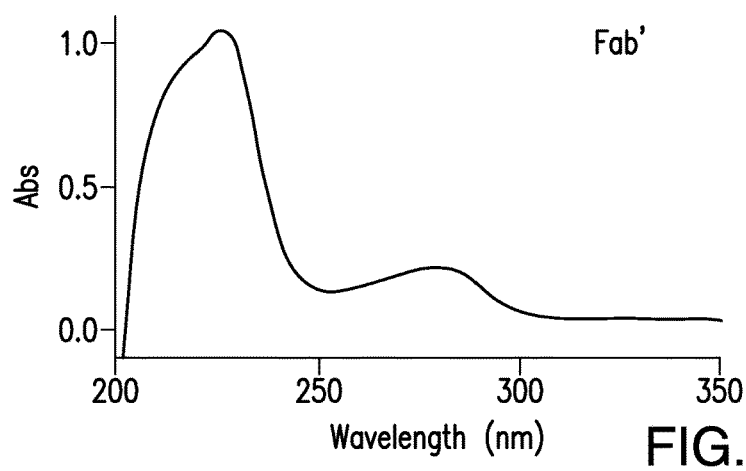
Figure 18A:
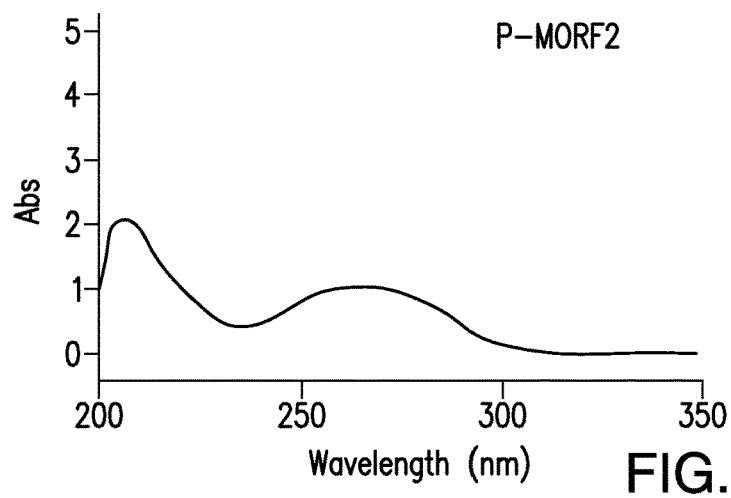
FIG. 18A-FIG. 18E shows the characterization of P-MORF2 complex.
Figure 18B:
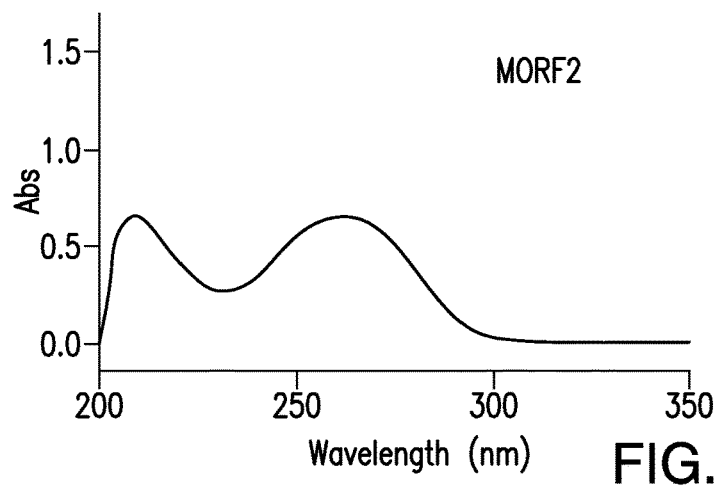
Figure 18C:
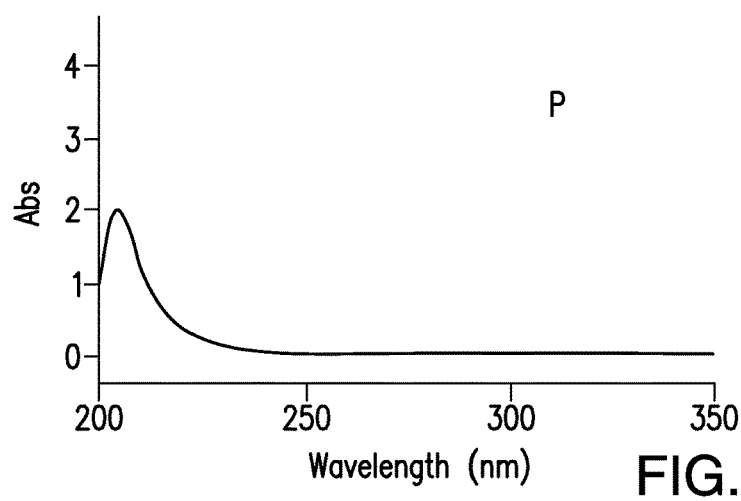
Figures 18D, 18E:
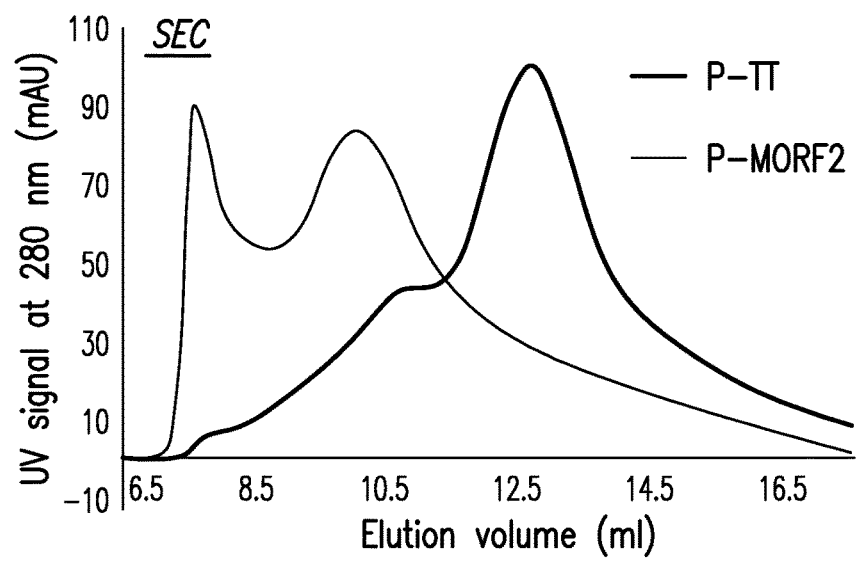

To prepare the Fab'-MORF1 conjugate (FIG. 10A), the Fab' fragment from a mouse anti-human CD20 IgG2a mAb (1F5) (Press et al., 1987) was tethered to the 3' end of MORF1 via a thioether bond. In FIG. 10A, * indicates SMCC or succinimidyl-4-(N-maleimidomethyl)cyclohexane-1-carboxylate heterobifunctional linker. The conjugates were optionally labeled with rhodamine (RHO) for imaging studies. Fab'-MORF1 was successfully synthesized as confirmed by HPLC (FIG. 10B, which utilized Agilent Zorbax 300SB-C18 column (4.6×250 mm) eluted with a gradient of buffer A ($H_2O$+0.1% trifluoroacetic acid v/v) and buffer B (acetonitrile+0.1% trifluoroacetic acid v/v) and size exclusion chromatography (SEC) (FIG. 17A, using Sephacryl S-100 HR16/60 column eluted with PBS); the coupling reaction followed a 1:1 stoichiometry as characterized by MALDI-ToF mass spectrometry (FIG. 17B) and UV-visible spectroscopy (FIG. 17C-FIG. 17E). The molecular weight (MW) of Fab'-MORF1 was about 57.5 kDa. In FIG. 17, the profile of Fab'-MORF1 demonstrated the process of purification by ÄKTA FPLC—the first peak (eluted at 53 mL) represented the conjugate (collected during purification); the second peak (eluted at 70 mL) indicated unconjugated MORF1 (removed). Fab'-MORF1 was characterized by an earlier elution volume comparing to Fab'-SH (56 mL). In FIG. 17B, the major fraction shows that the molecular weight was about 57.5 kDa (Fab': ~48.8 kDa, MORF1: ~8.6 kDa); a small fraction of unconjugated Fab' was observed. The UV-Vis spectra of the purified Fab'-MORF1 (FIG. 17C), the unconjugated MORF1 (FIG. 17D), and the Fab' fragment (FIG. 17E) are also shown. Concentrations of all components were 2.5 µM. The Fab'-MORF1 conjugate was characterized by a combination of absorbance at 260 nm (contributed by MORF1) and 280 nm (contributed by Fab').

Figure 10D:
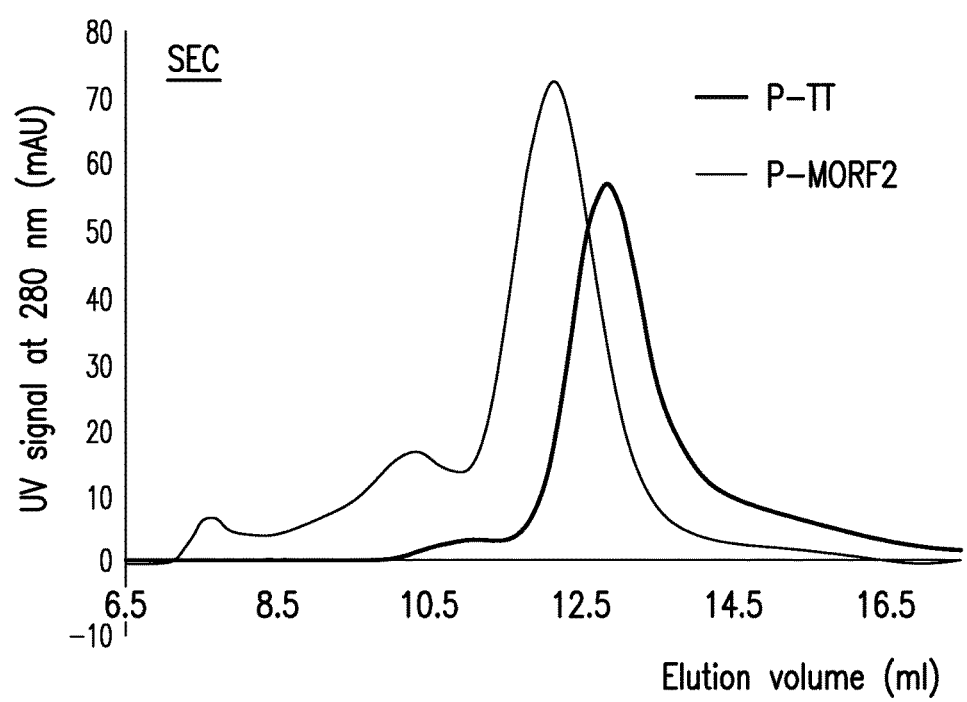

To prepare the multivalent P-MORF2 conjugates (FIG. 10C), HPMA copolymers containing glycyl-glycine (GG; spacer) side-chains terminated in (amine-reactive) thiazolidine-2-thione (TT) groups were synthesized. In FIG. 10C, MA-GG-TT indicates N-methacryloylglycylglycine thiazolidine-2-thione (MA-GG-TT). These polymer precursors (P-TT) were synthesized by reversible addition-fragmentation chain transfer (RAFT) polymerization. A polymerizable fluorescein isothiocyanate (FITC) derivative was optionally added for imaging studies. Using RAFT polymerization, polymer backbones with narrow MW distribution (polydispersity index ≤1.15, as determined by SEC) were reproducibly synthesized. Furthermore, the amine-derivatized MORF2 oligos (MORF2-$NH_2$) were grafted via stable amide linkage to the side chains of the HPMA copolymers to produce multivalent P-MORF2. The conjugates were purified and characterized by SEC (FIG. 10D). FIG. 10D shows an SEC analysis of representative P-TT and P-MORF2 (valence=3) using a Superose 6 HR10/30 column (acetate buffer+30% acetonitrile v/v). Three different P-MORF2's with varying backbone MW and valences (i.e., number of MORF2 per polymer chain) were synthesized (FIG. 18A-FIG. 18E). The backbone number average molecular weights (Mn) of these conjugates ranged from 70 to 136 kDa. Valences of the three P-MORF2 preparations were 2, 3, and 10, respectively.

FIG. 18 shows the UV-Vis spectra of the SEC-purified P-MORF2 conjugate (1 mg/mL (FIG. 18A)), unconjugated MORF2 (2.5 µM (FIG. 18B)), and HPMA polymers (P) (1 mg/mL (FIG. 18C)). The multivalent P-MORF2 conjugates were characterized by UV absorbance at 260 nm (contributed by MORF2). FIG. 18D provides a table summarizing physicochemical properties of different P-MORF2 conjugates and their polymer precursors (P-TT) that were synthesized and used in the experiments described herein. Number average molecular weight (Mn) and polydispersity (Pd) were determined by SEC. Number of thiazolidine-2-thione (TT) groups per polymer chain (TT/P) was determined by UV absorbance at 305 nm; number of FITC per chain (FITC/P) was determined by absorbance at 495 nm; number of MORF2 oligo per chain (MORF2/P) was determined by UV absorbance at 260 nm. FIG. 18E shows size exclusion chromatography (SEC) analysis of P-MORF2 #3 and its P-TT polymer precursor by ÄKTA FPLC; Superose 6 HR10/30 column (acetate buffer pH 6.5+30% acetonitrile v/v). The retention limit of this column is about 7 mL.

(3) In Vitro Hybridization of Fab'-MORF1 and P-MORF2

Figure 11A:
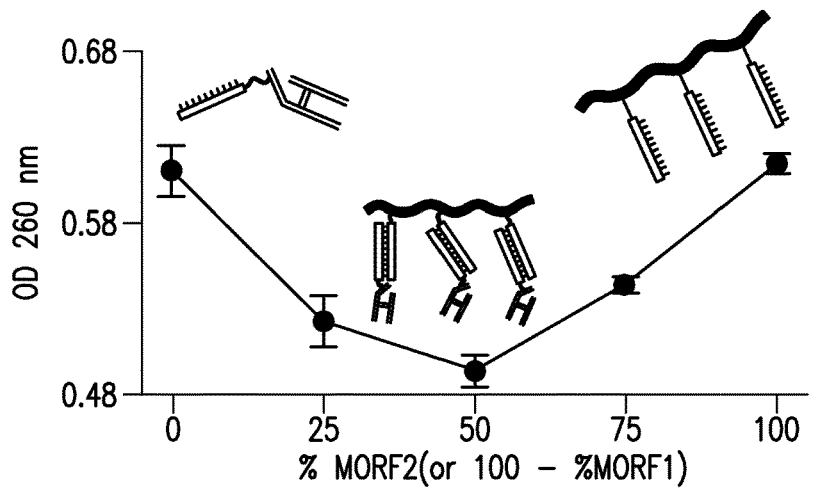
FIG. 11A-FIG. 11C shows in vitro hybridization of Fab'-MORF1 and P-MORF2 complexes.
Figure 19:
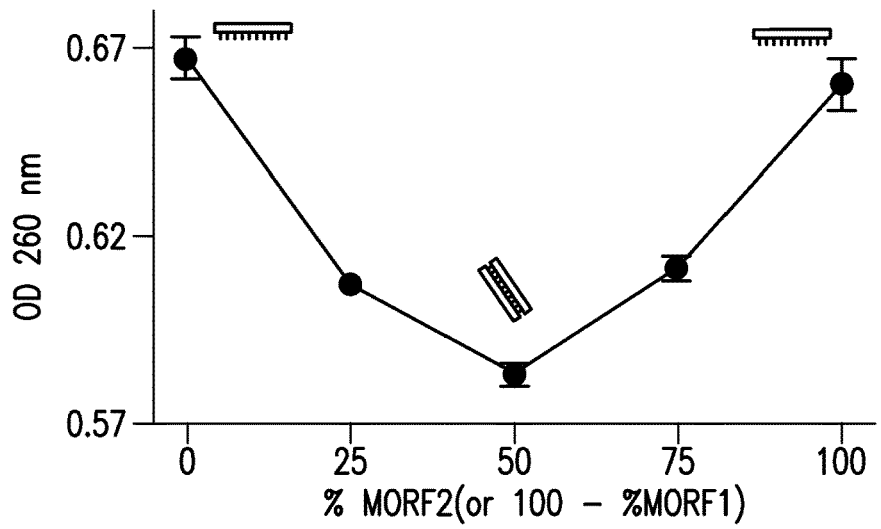
FIG. 19 shows the hypochromic effect upon hybridization of free, unconjugated MORF1 and MORF2.

Hybridization of the two conjugates via MORF1-MORF2 biorecognition was first evaluated by UV-visible spectroscopy. The two conjugates were mixed in different ratios, and the optical density at 260 nm (contributed by bases) was measured. Upon mixing Fab'-MORF1 and P-MORF2, a "hypochromic effect" was observed (FIG. 11A); the OD260 nm reached a minimum when a molar ratio of 1:1 (MORF1: MORF2) was used. Such decrease was due to hydrogen bonding between complementary bases that limited the resonance of the aromatic rings. Using the same method, the hybridization of the free, unconjugated MORF1 and MORF2, and the same hypochromicity was observed (FIG. 19). In FIG. 19, the optical density (OD) at 260 nm decreased when the two MORFs (in PBS, pH=7.4) were mixed (in different %). Data are presented as mean±SD (n=3). These results indicated that the function of MORF1-MORF2 hybridization was preserved after conjugation to Fab' or polymers.

Figure 11B:
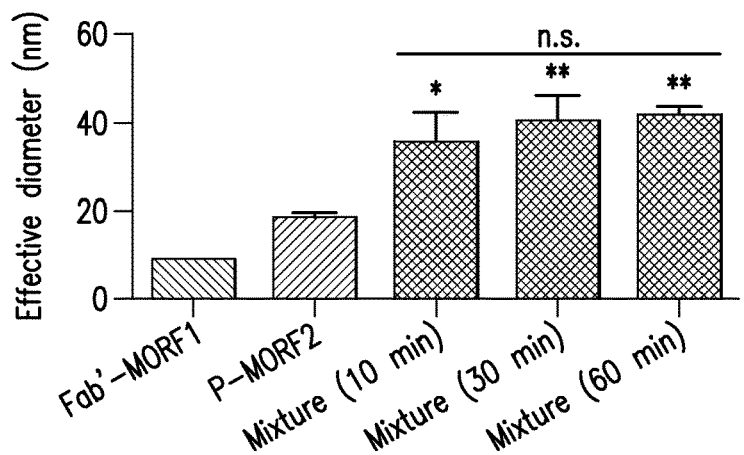
Figure 20:
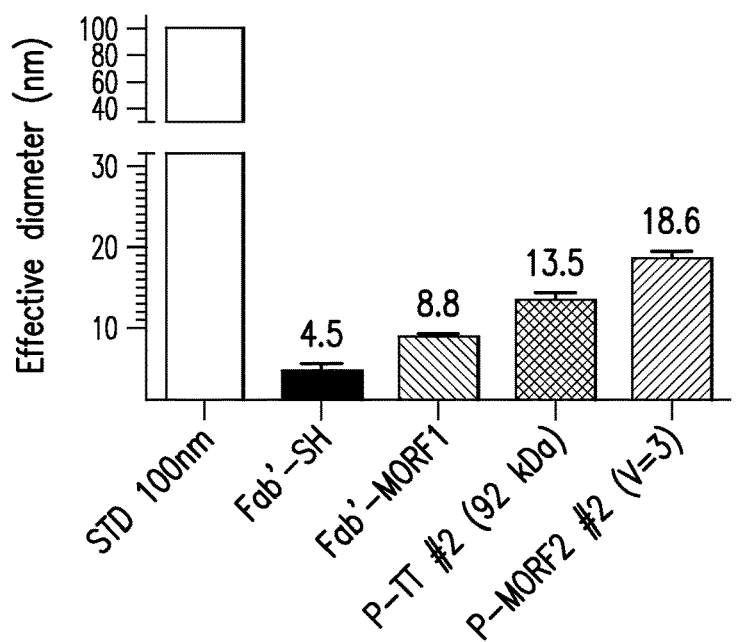
FIG. 20 shows the hydrodynamic effective diameters of Fab'-MORF1 and P-MORF2 and precursors Fab'-SH and P-TT.
Figure 21A:
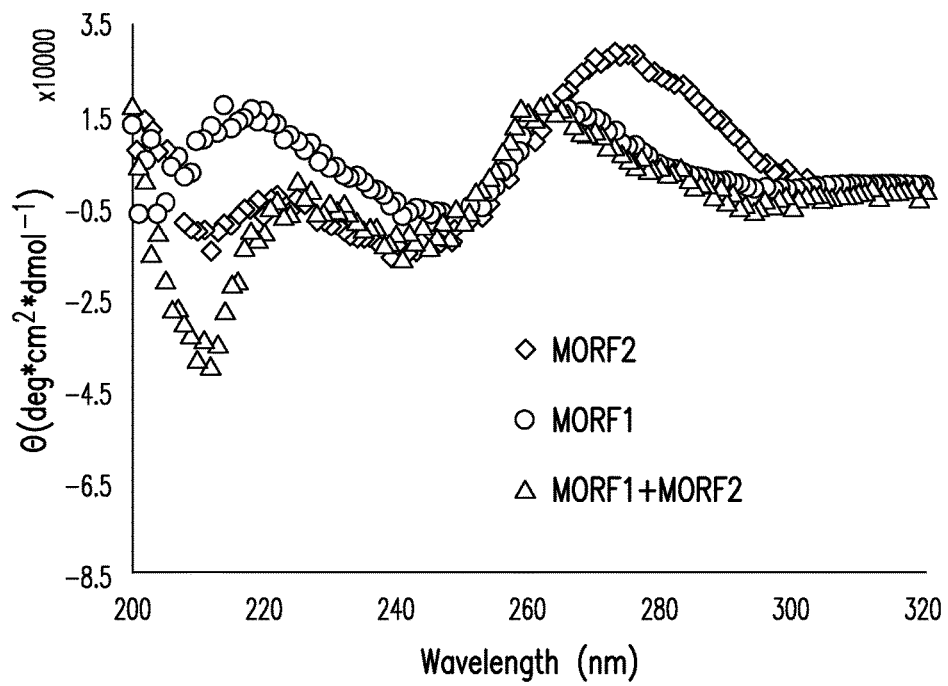
FIG. 21A-FIG. 21D show analysis of hybridization of free, unconjugated MORFs, the conjugates, and their mixtures by CD spectroscopy.
Figure 21B:
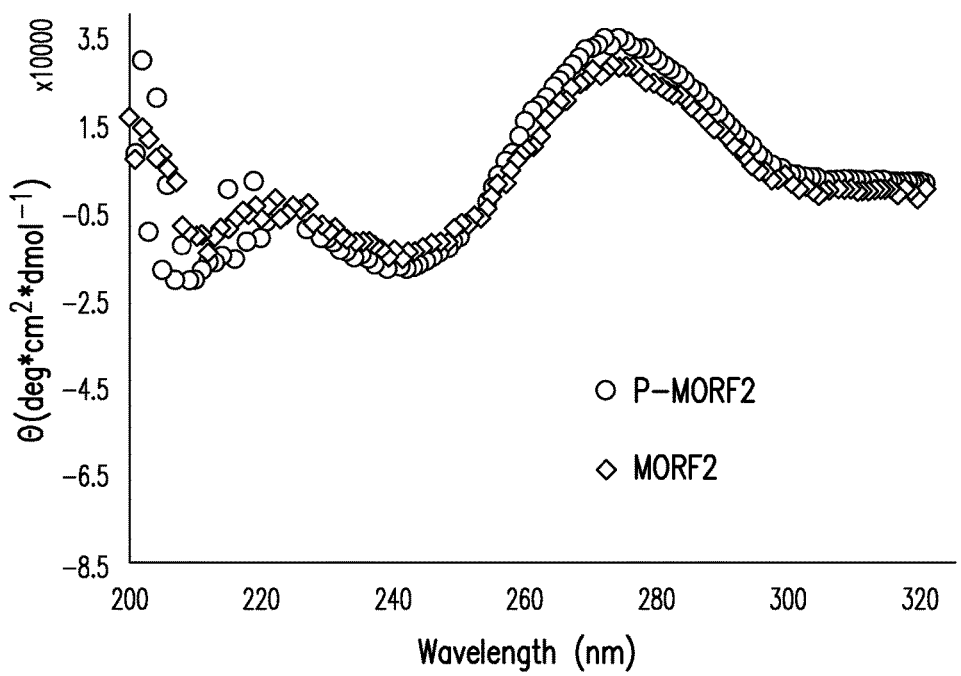
Figure 21C:
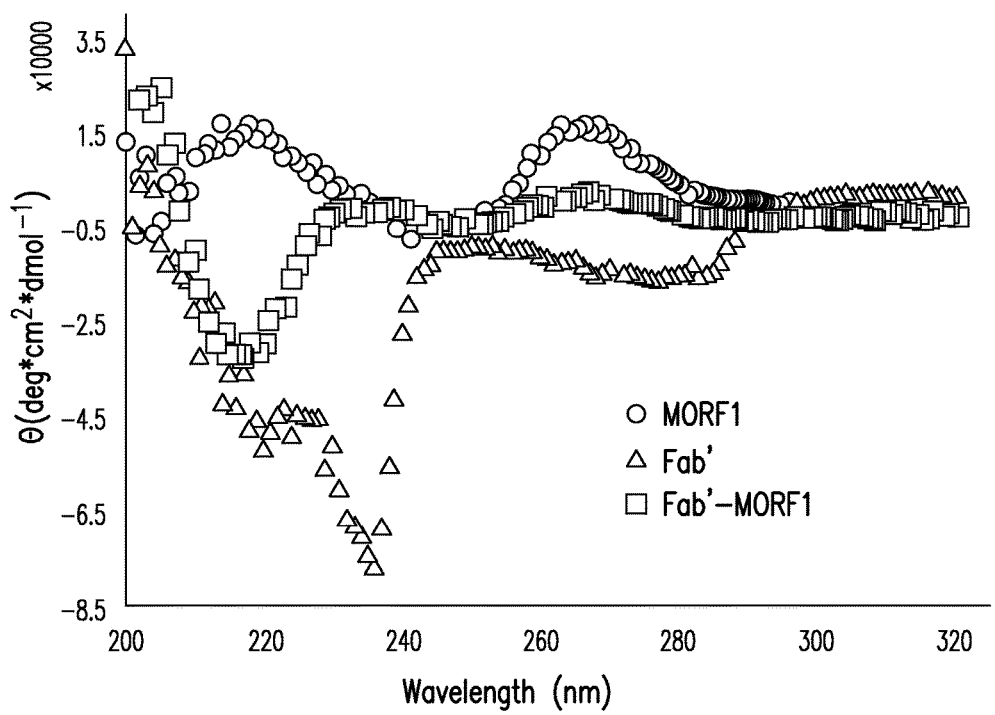
Figure 21D:
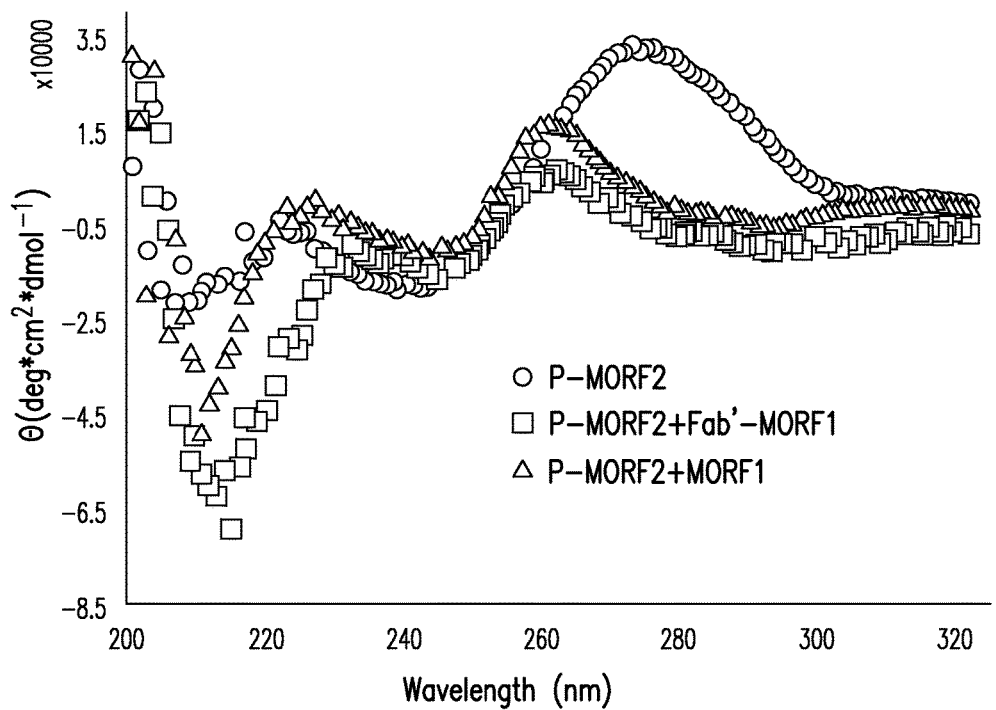

Furthermore, the binding of Fab'-MORF1 and P-MORF2 was characterized by dynamic light scattering (DLS) (FIG. 11B, FIG. 20). As shown in FIG. 11B, a significant and rapid increase of hydrodynamic size upon mixing the two conjugates (at equimolar MORF1/MORF2) was revealed. The fast attainment of stable diameter (~40 nm) reflected a fast binding kinetics (<10 min) of MORF1-MORF2 hybridization of the conjugates. This characteristic is favorable for the design of drug-free macromolecular therapeutics. In FIG. 11B, the valence of P-MORF2 was 3. Statistics, unless otherwise indicated, were performed by comparing the mixture with P-MORF2 (*$p<0.05$, **$p<0.005$, n.s.=no significant difference). In FIG. 20, all components were dissolved in PBS (pH=7.4) and measured in line with a Nanosphere™ polystyrene size standard with a diameter of 102±3 nm (STD100 nm). Data are presented as mean±SD (n=3).

Figure 11C:
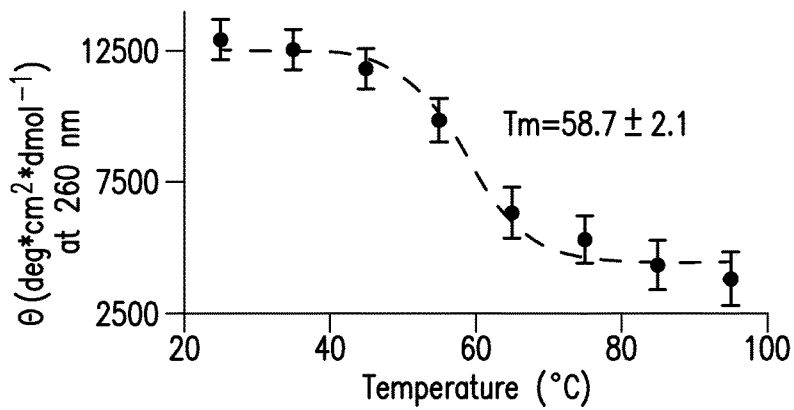

Circular dichroism (CD) spectroscopy was used to determine the melting temperature (Tm) of the Fab'-MORF1/P-MORF2 complex in physiological conditions (PBS pH=7.4) (FIG. 11C). First, a pronounced optical signature (maximum at 260 nm, minimum at 210 nm) indicating A-form double helixes (Johnson et al., 2000) was obtained upon mixing the two conjugates; a similar CD profile was observed when unconjugated MORF1 and MORF2 were mixed (FIG. 21A-FIG. 21D).

For example, FIG. 21 sows the CD spectra of free, unconjugated MORFs, the conjugates, and their mixtures for analysis of hybridization. All components were dissolved in PBS (pH 7.4) at 50 µM MORF equivalent concentration. The y-axis shows molar ellipticity (θ). FIG. 21A shows free MORF1, MORF2, and the equimolar mixture of both. When mixed, an optical signature (maxima at 260 nm, minima at 210 nm) indicates that A-form double helixes were obtained. FIG. 21B shows a comparison of P-MORF2 (valence=3) with free MORF2. An identical spectrum was observed. FIG. 21C shows a comparison of the Fab'-MORF1 conjugate with free Fab' fragment and free MORF1. The conjugate appears to have the combined optical signatures of Fab' and MORF1. FIG. 21D shows that the mixing P-MORF2 with either free MORF1 or Fab'-MORF1 (equimolar MORF1/MORF2) shifted the CD spectrum from that of the single-stranded MORF2 to that indicating A-form double-stranded oligos. Such spectral shift indicated that the function of MORF1-MORF2 hybridization was preserved after conjugation to Fab' or polymers.

Second, a thermal melting study was performed to analyze the mixture of Fab'-MORF1 and P-MORF2. Data showed that the aforementioned CD signature no longer existed at 95° C.; the positive band at 260 nm underwent a significant bathochromic shift that produced a peak centered around 275 nm (FIG. 22A-FIG. 22B, FIG. 23A-FIG. 23C). The thermo-melting curve shown in FIG. 11C demonstrates that the signal at 260 nm decreased in a sigmoidal pattern as temperature increased. Results of nonlinear regression indicated a Tm value of about 57 to 62° C. The Tm is well above body temperature, indicating in vivo stability of the binding. In FIG. 11C, the melting temperature (Tm) resulted from fitting the data to a logistic function using nonlinear regression (GraphPad Prism 5 software). All experiments were performed at physiological conditions (PBS, pH=7.4). Data are presented as mean±SD (n=3).

Figure 22A:
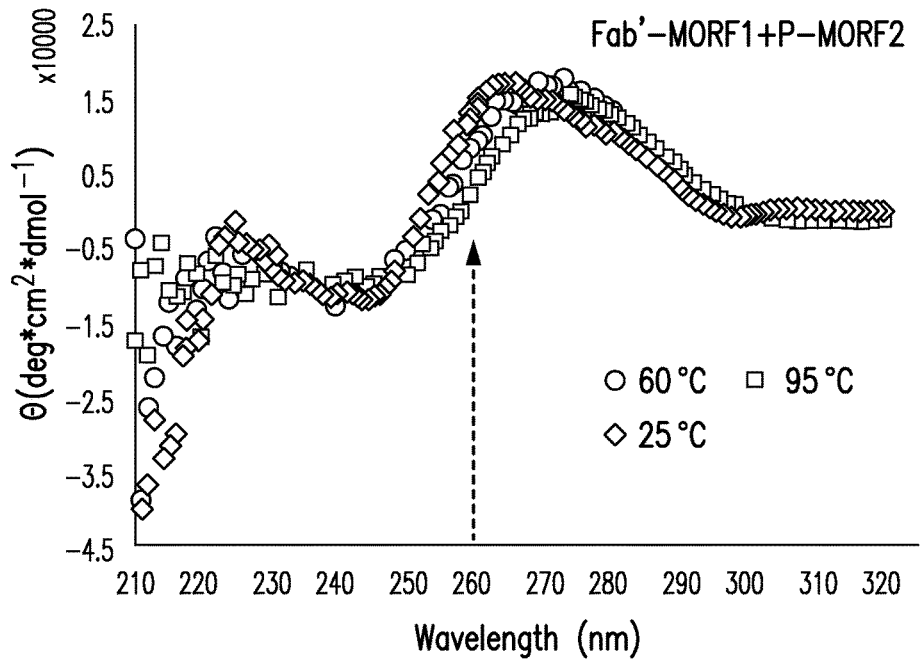
FIG. 22A-FIG. 22B show analysis of melting temperature (Tm) of the Fab'-MORF1/P-MORF2 hybridization by CD spectroscopy.
Figure 22B:
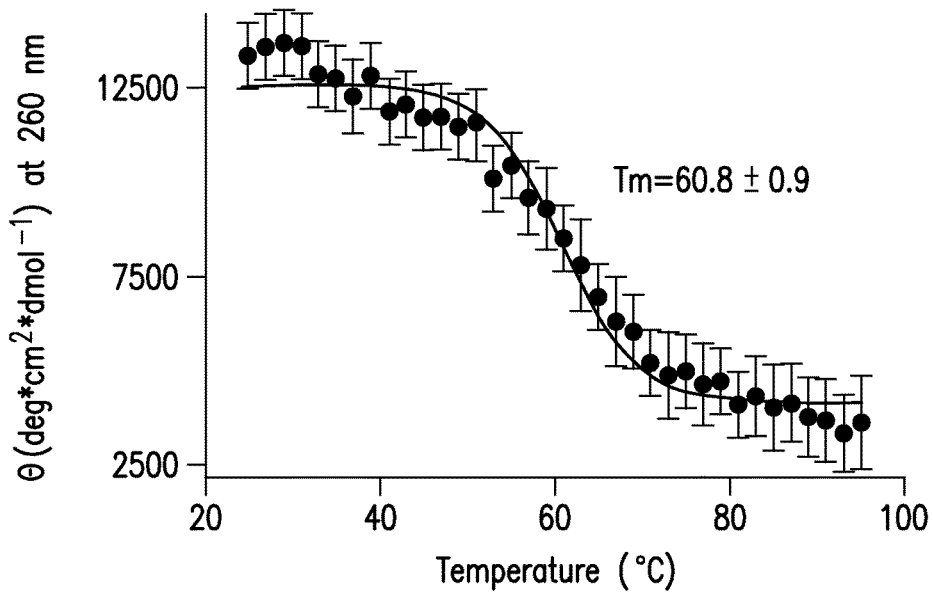

FIG. 22A-FIG. 22B show an analysis of melting temperature (Tm) of the Fab'-MORF1/P-MORF2 hybridization by CD spectroscopy. FIG. 22A shows a CD spectra of the mixture of Fab'-MORF1 (5 µM MORF1-eqv.) and P-MORF2/v3 (5 µM MORF2-eqv.; valence=3) in PBS (pH 7.4) at different temperatures. When temperature increased from 25° C. to 60° C. and 95° C., the positive band at 260 nm underwent a bathochromic shift that produced a peak centered around 275 nm. Molar ellipticity (θ) at 260 nm was used in the following thermal melting studies. FIG. 22B shows a CD thermal melting curve of the hybridized Fab'-MORF1/P-MORF2. A sigmoidal decrease of θ at 260 nm was observed as temperature increased. Data are presented as mean±SD (n=3). These data were fitted to a logistic function to obtain Tm; results of nonlinear regression indicated Tm=60-62° C. The forward scan (increasing temperature) analysis as shown here gave similar results as the reverse scan (decreasing temperature—see FIG. 11C).

Figure 23A:
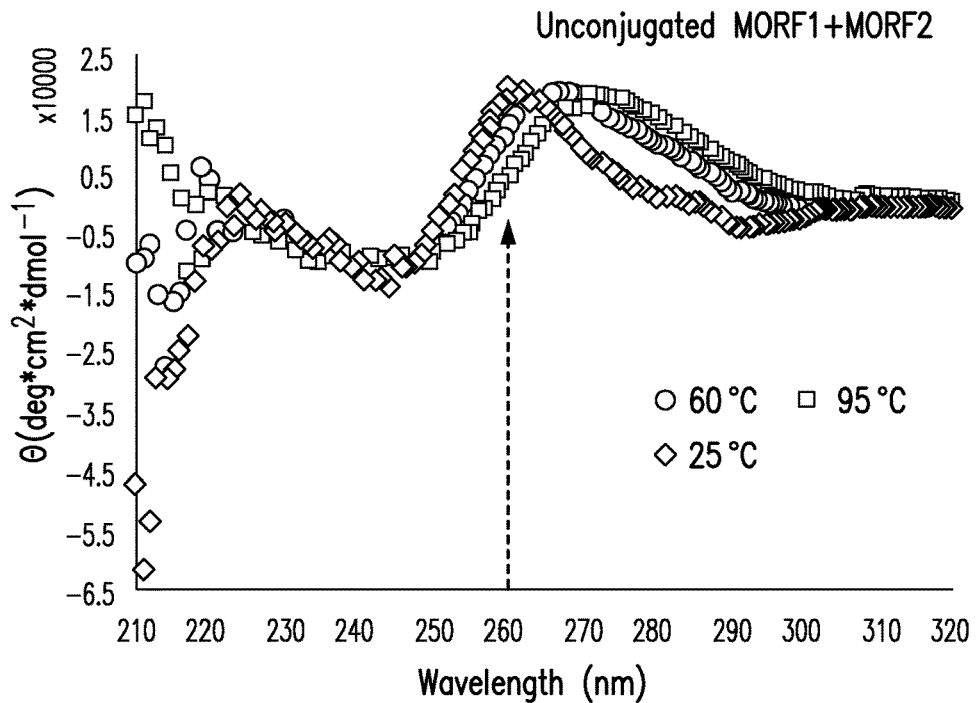
FIG. 23A-FIG. 23C show analysis of melting temperature (Tm) of the free, unconjugated MORF1/MORF2 hybridization by CD spectroscopy.
Figure 23B:
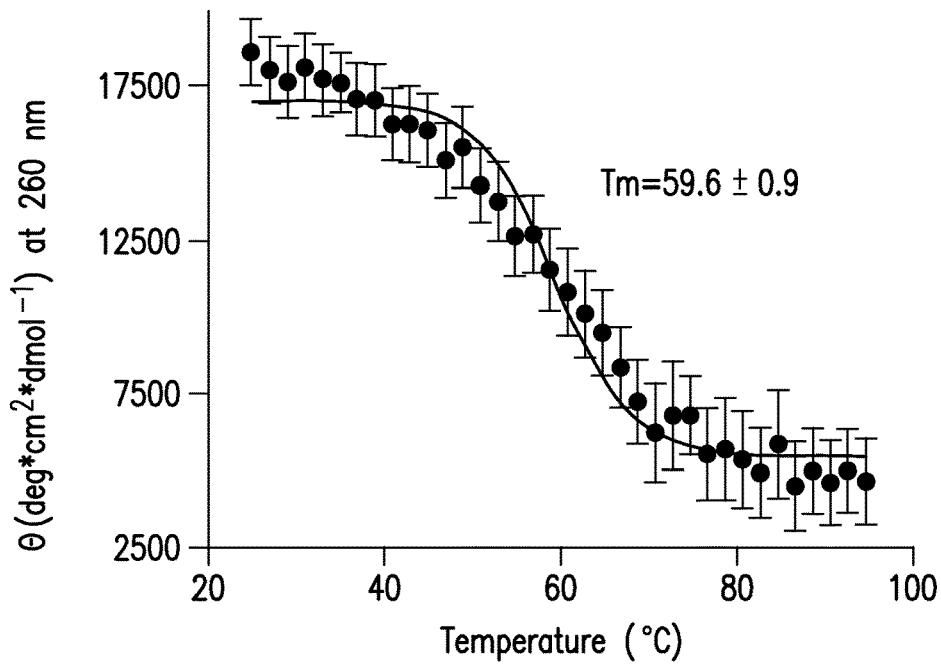
Figure 23C:
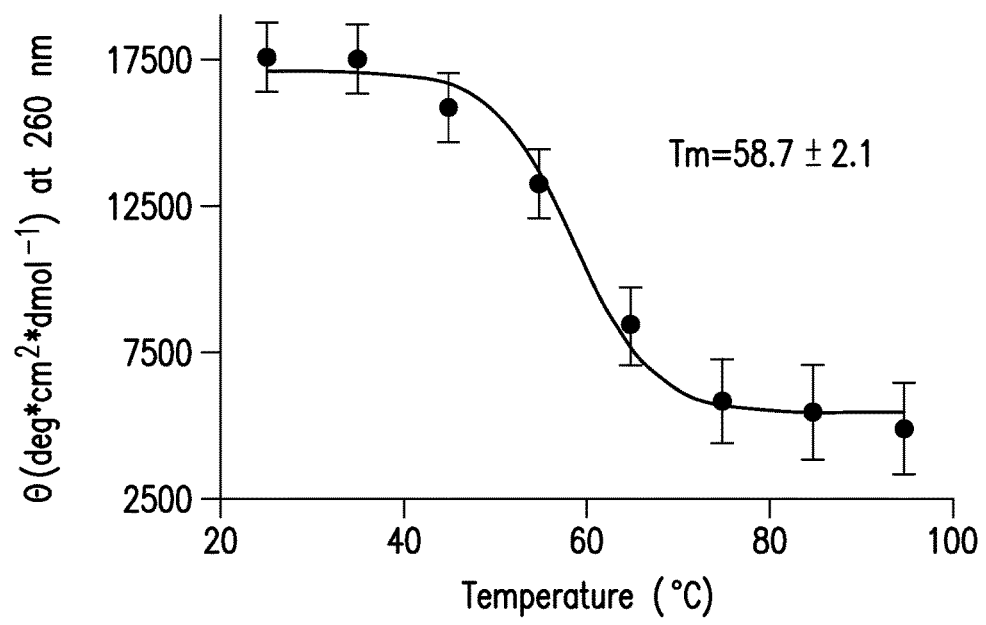

FIG. 23 shows an analysis of melting temperature (Tm) of the free, unconjugated MORF1/MORF2 hybridization by CD spectroscopy. For example, FIG. 23A shows a CD spectra of the mixture of MORF1 (5 µM) and MORF2 (5 µM) in PBS (pH 7.4) at different temperatures. When temperature increased from 25° C. to 60° C. and 95° C., the positive band at 260 nm underwent a bathochromic shift that produced a peak centered around 275 nm. Molar ellipticity (θ) at 260 nm was used in the following thermal melting studies. FIG. 23B shows a forward CD thermo-melting curve of the hybridized MORF1/MORF2 in which data were collected as temperature increased. FIG. 23C shows a reverse CD thermo-melting curve of the hybridized MORF1/MORF2 in which data were collected as temperature decreased. The profile demonstrating a sigmoidal change of θ at 260 nm was identical in both forward and reverse scans. Data are presented as mean±SD (n=3). Results of nonlinear regression using a logistic function indicated Tm=57-61° C.

(4) Biorecognition of Fab'-MORF1 and P-MORF2 at B-Cell Surface

Figure 12A:
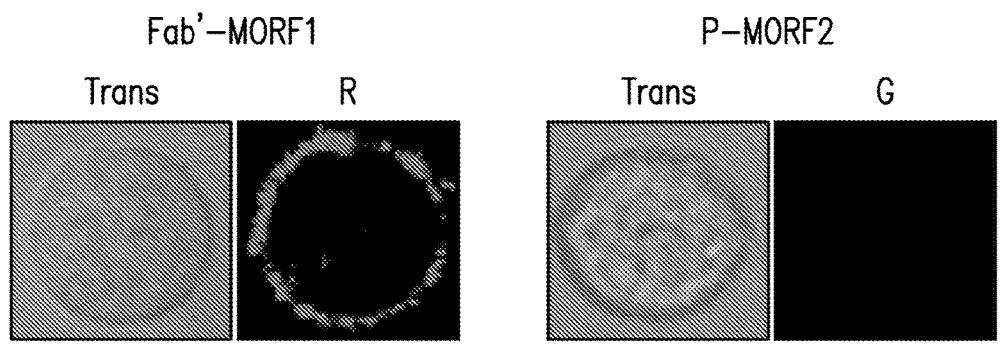
FIG. 12A-FIG. 12C shows biorecognition of Fab'-MORF1 complex and P-MORF2 complex at the cell surface.
Figure 12B:
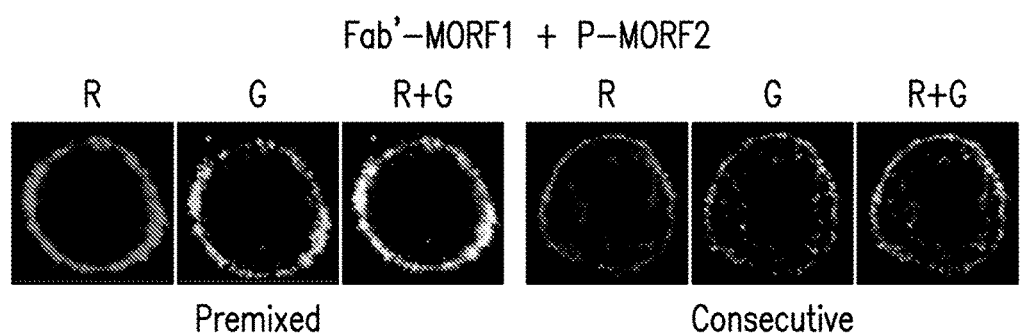
Figure 12C:
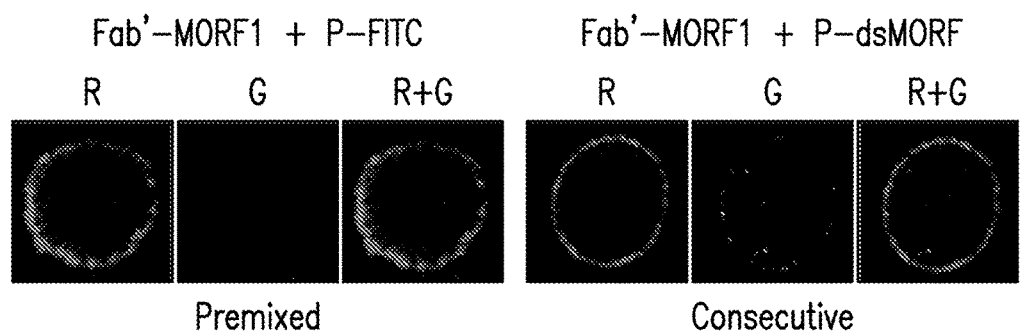

Human B-cell lymphoma Raji cell line (CD20$^+$) (Stashenko et al., 1980; Shan et al., 1998) was used to study the biorecognition of Fab'-MORF1 and P-MORF2 (valence=2) at the cell surface. This study was performed by confocal fluorescence microscopy. First, exposure of Raji cells to rhodamine-labeled Fab'-MORF1 resulted in cell surface red signal (RHO) decoration due to Fab'-MORF1 binding to CD20; cells exposed to only FITC-labeled P-MORF2 did not show any fluorescent signal (FIG. 12A, Fab'-MORF1 at 0.4 μM or P-MORF2 at 0.4 μM, MORF2 equivalent). Second, when Raji cells were exposed to both fluorescently labeled conjugates (Fab'-MORF1+P-MORF2), either consecutively (1 hour apart) or as a premixture (i.e., mixture of Fab'-MORF1 (0.4 μM) and P-MORF2 (0.4 μM, MORF2 equivalent), the red and the green (FITC) signals were well co-localized at the surfaces of B-cells (FIG. 12B). This observation indicated successful MORF1-MORF2 hybridization at cell surface. FIG. 12C shows the microscopic images obtained from two control groups: (1) cells exposed to the premixture of Fab'-MORF1(-RHO) and an HPMA copolymer carrying FITC dye but without MORF2 (P-FITC, excess amount); (2) a "pre-blocking" control achieved by exposing cells consecutively to Fab'-MORF1 (0.5 μM) (-RHO) followed by a mixture of P-MORF2(-FITC) with an excess of unconjugated MORF1 (this produced HPMA copolymers grafted with double-stranded MORF; P-dsMORF). Both control treatments resulted in only the red signal at cell surfaces (FIG. 12C) due to absence of a biorecognition pair. Results of these controls confirmed that the cell surface biorecognition of Fab'-MORF1 and P-MORF2 was indeed mediated by MORF1-MORF2 hybridization.

(5) Induction of Apoptosis of Human NHL B-Cells

Figure 24A:
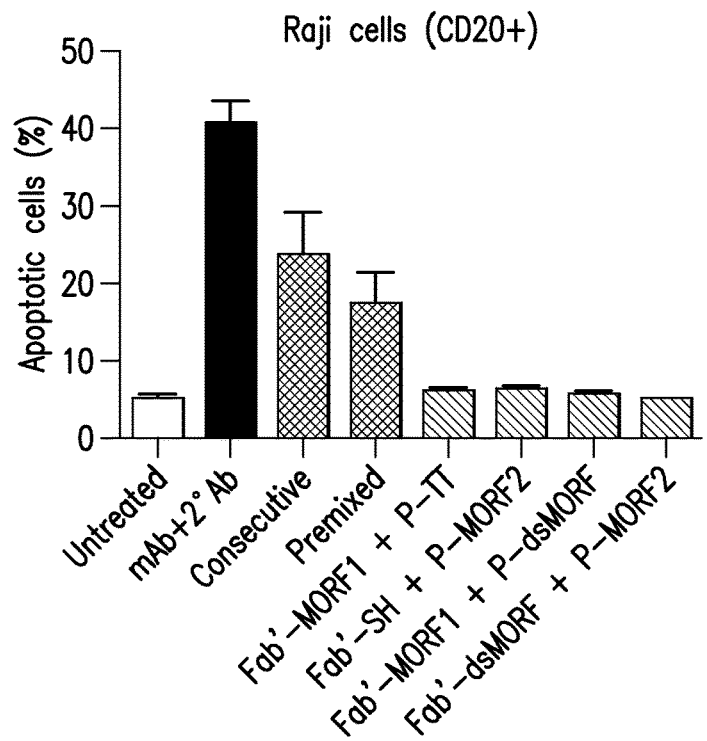
FIG. 24A-FIG. 24B show control studies of in vitro apoptosis in Raji cells and DG75 cells.
Figure 24B:
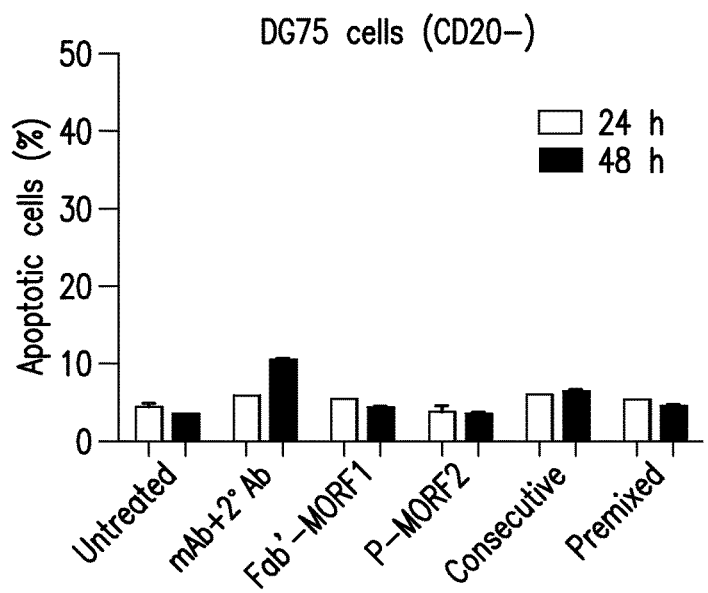

Apoptosis induction of human B-cell lines (Raji and DG75) was evaluated by three methods: caspase-3 activation assay, annexin V/propidium iodide (PI) binding assay, and terminal deoxynucleotidyl transferase dUTP nick end-labeling (TUNEL) assay. In these experiments, anti-CD20 1F5 mAb hyper-cross-linked with a goat anti-mouse secondary Ab (2° Ab) was used as a positive control to imitate the function of FcR+ immune effector cells (Shan et al., 1998). This control partly reflected the therapeutic efficacy of anti-CD20 mAbs. Results showed that co-treatment with Fab'-MORF1 and P-MORF2, either consecutively or as a premixture, effectively induced apoptosis of Raji B-cells (FIG. 13). In contrast, single-component treatments with either Fab'-MORF1 or P-MORF2 failed to initiate apoptosis. A series of control experiments (FIG. 24) validated the hypothesis that MORF1-MORF2 hybridization with concomitant crosslinking of CD20 antigens is responsible for the apoptosis induction. Raji cells were exposed to: (1) a mixture of Fab'-MORF1 and the polymer precursor P-TT; (2) a mixture of Fab' and P-MORF2; (3) "pre-blocked" conjugates whose MORF1 or MORF2 binding sites were blocked by excess unconjugated complementary MORFs prior to treatment. None of these treatments induced apoptosis, due to absence of MORF1-MORF2 hybridization (FIG. 24A). Furthermore, the apoptosis of a negative control B-cell line (DG75) that does not (or minimally) express CD20 was evaluated (Ben-Bassat et al., 1977). The levels of apoptosis after co-treatment with two nanoconjugates were very low, and similar to that of the untreated cells (FIG. 24B). This result indicated that CD20 binding is a necessary event for apoptosis induction.

For example, FIG. 24 shows control studies of in vitro apoptosis by annexin V/PI binding assay. FIG. 24A show apoptosis induction of Raji B-cells (high levels of CD20 expression). Incubation time was 48 h. FIG. 24B shows apoptosis induction of DG75 B-cells (minimal or no CD20 expression). Incubation time was as indicated. The following indications apply to FIG. 24A and FIG. 24B: Untreated: cells in culture medium; mAb+2° Ab: 1F5 mAb (0.5 μM) followed (1 h later) by goat anti-mouse secondary Ab (0.25 μM); Fab'-MORF1: single-component at 0.5 μM; P-MORF2: single-component of P-MORF2/v3 at 0.5 μM (MORF2 equivalent); Consecutive: Fab'-MORF1 (0.5 μM) followed (1 h later) by P-MORF2/v3 (0.5 μM MORF2-eqv.); Premixed: premixture of Fab'-MORF1 (0.5 μM) and P-MORF2/v3 (0.5 μM MORF2-eqv.); Fab'-MORF1+P-TT: premixture of Fab'-MORF1 (0.5 μM) and the polymer precursor P-TT #2 (1 mg/mL); Fab'-SH+P-MORF2: premixture of free Fab' (0.5 μM) and P-MORF2 (0.5 μM MORF2-eqv.); Fab'-MORF1+P-dsMORF: consecutive treatment (1-h interval) of Fab'-MORF1 (0.5 μM) and "pre-blocked" P-MORF2 (~1 mg/mL) whose MORF2 binding sites were blocked by excess free MORF1 (1 h before treatment); Fab'-dsMORF+P-MORF2: consecutive treatment (1-h interval) of "pre-blocked" Fab'-MORF1 (0.5 μM) whose MORF1 binding sites were blocked by excess free MORF2 (1 h before treatment) and P-MORF2 (0.5 μM MORF2-eqv.). Apoptotic cells percentage was quantified by flow cytometry. Data are presented as mean±SD (n=3).

(6) Optimization of Apoptosis Induction

Figure 13A:
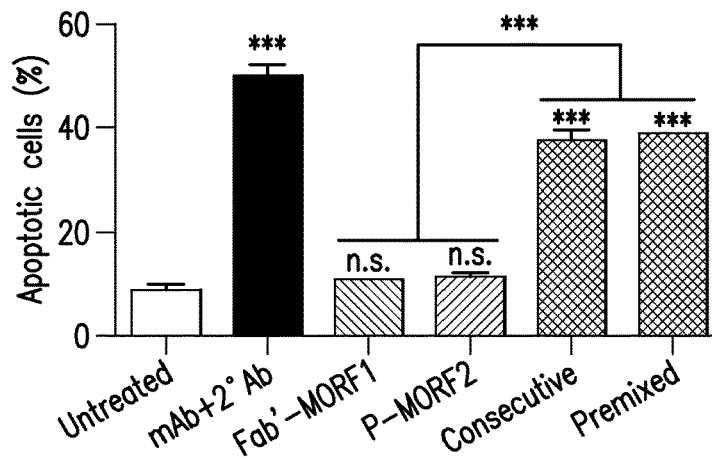
FIG. 13A-FIG. 13C shows induction of apoptosis in Raji B-cells using disclosed complexes and/or compositions.

To optimize the disclosed therapeutic system, several factors and their impact on apoptosis of Raji B-cells were examined, including concentration of conjugates, ratio between two conjugates, valence of P-MORF2, and exposure time. A P-MORF2 containing about 3 oligos per polymer chain (P-MORF2/v3) was first used. Results of annexin V/PI staining assay indicated that 1 μM Fab'-MORF1 and equimolar P-MORF2/v3 (MORF1:MORF2=1:1) induced about 40% apoptotic cells (more than 4 fold compared to untreated) (FIG. 13A). In FIG. 13A, the follow apply: Untreated: cells in culture medium; mAb+2° Ab: 1F5 mAb (1 μM) followed (1 h later) by goat anti-mouse secondary Ab (0.5 μM); Fab'-MORF1: single-component at 1 μM; P-MORF2: single-component of P-MORF2/v3 at 1 μM (MORF2-eqv.); Consecutive: Fab'-MORF1 (1 μM) followed (1 h later) by P-MORF2/v3 (1 μM); Premixed: premixture of Fab'-MORF1 (1 μM) and P-MORF2/v3 (1 μM). Statistics, unless otherwise indicated, was performed by comparing each group with untreated (***p<0.0001, n.s.=no significant difference).

Figure 13B:
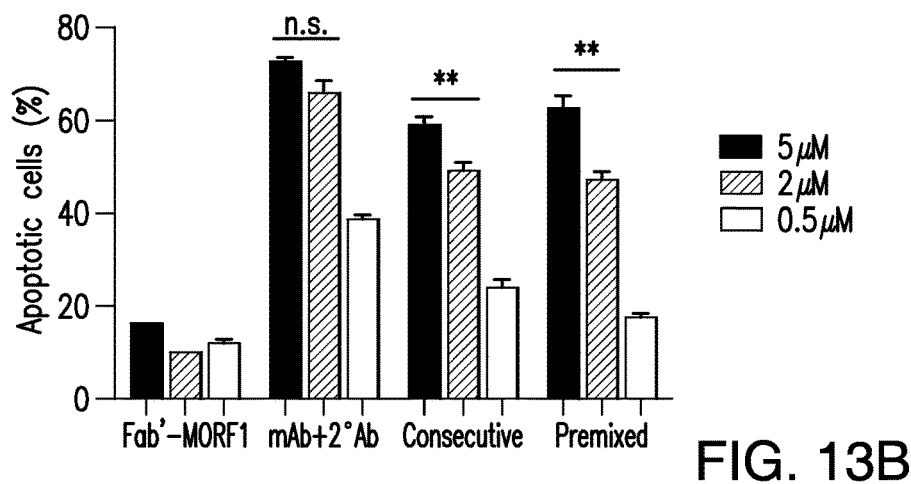

When all conditions were kept identical except different concentrations of Fab'-MORF1 (and corresponding P-MORF2/v3), a concentration-dependent apoptosis induction was observed (FIG. 13B). In FIG. 13B, the following apply: **p<0.005, n.s.=no significant difference. Data indicated that increasing concentrations of the conjugates from 0.5 μM to 2 and 5 μM (Fab' equivalent) resulted in higher levels of apoptosis. The dose-dependent trends were observed in both consecutive and premixed treatment regimens as well as in the positive control (mAb+2° Ab). At the highest concentration tested (5 μM), apoptosis induction by drug-free macromolecular therapeutics (Fab'-MORF1+P-MORF2/v3) reached about 7 fold compared to untreated controls. Furthermore, the percentage of the apoptotic cells induced by mAb+2° Ab seemed to saturate when the concentration of 1F5 mAb was increased from 2 to 5 μM; however, such saturation was not observed in the treatment groups receiving the disclosed compositions and complexes. This difference was likely due to P-MORF2 having multimeric interactions with targets, in contrast to mAbs with only two binding sites.

Figure 13C:
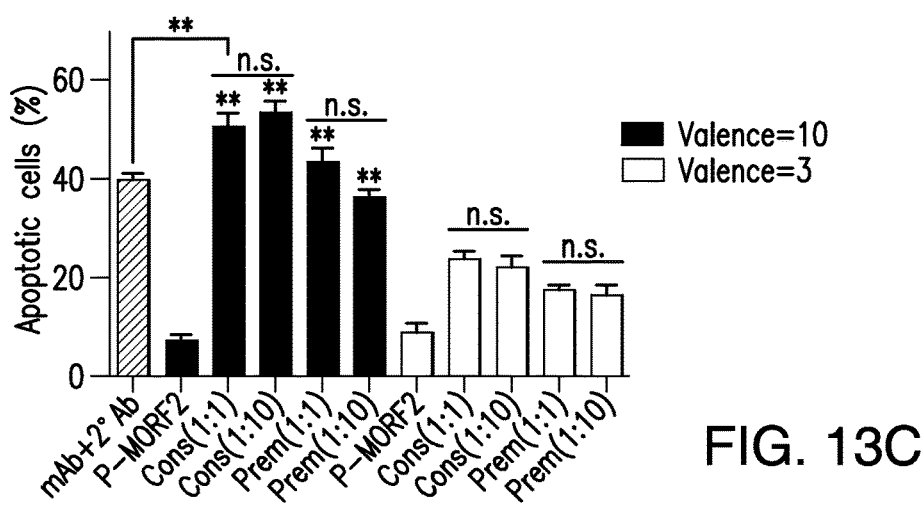

Furthermore, the influence of the valence of P-MORF2 and the ratio between Fab'-MORF1 and P-MORF2 on apoptosis induction of Raji B-cells was examined A "high-valence" P-MORF2 containing 10 oligos per chain (P-MORF2/v10) was compared with P-MORF2/v3 (3 oligos per chain). Results showed that when all treatment conditions were identical (0.5 μM Fab', MORF1:MORF2=1:1 or 1:10), the P-MORF2/v10 conjugate induced about 2-fold higher levels of apoptosis comparing to P-MORF2/v3 (FIG. 13C). The consecutive treatment of Fab'-MORF1 and P-MORF2/v10 induced apoptosis more effectively than the positive control (consecutive treatment of mAb and 2° Ab; i.e., 1F5 mAb (0.5 μM) followed by goat anti-mouse secondary Ab (0.25 μM)). The higher level of apoptosis induction observed here was due to multivalency of P-MORF2/v10, which resulted in higher avidity to B-cells as well as more effective CD20 clustering (Johnson et al., 2009, 2012; Chu et al., 2012). When Raji cells were exposed to the same concentration of Fab'-MORF1 (0.5 μM), whereas a 10-time excess P-MORF2 was used (MORF1:MORF2=1:10), the apoptotic levels were not significantly enhanced as compared to the treatment with equimolar MORF1/MORF2 (FIG. 13C). Statistics, unless otherwise indicated, were performed by comparing each "high-valence" group with the corresponding "low-valence" group (**p<0.005, n.s.: no significant difference). All data are presented as mean±SD (n=3). The MORF1 binding sites on the surfaces of the Fab'-MORF1-decorated cells were saturated, which indicates good accessibility of MORFs on the polymer chain for hybridization (minimal steric hindrance effect by the polymer chain). The same trends of apoptosis induction were observed at different exposure times and from different apoptosis assays (FIG. 25A-FIG. 25B).

Figure 25A:
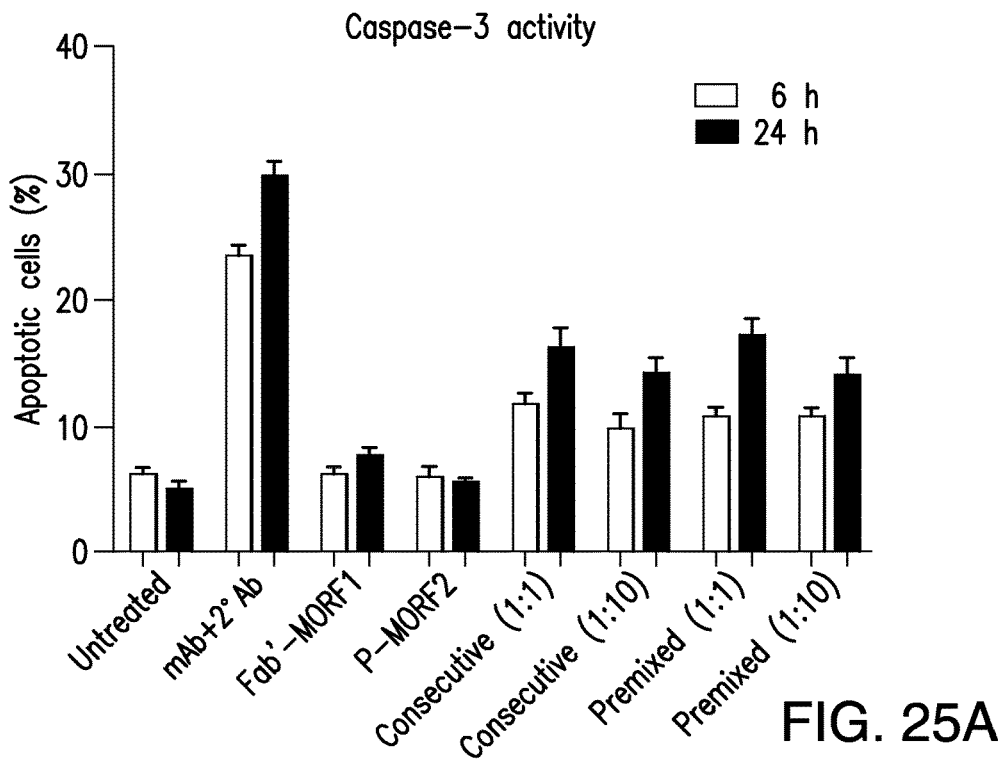
FIG. 25A-FIG. 25B show apoptosis of Raji B-cells analyzed by different assays and at different incubation times.
Figure 25B:
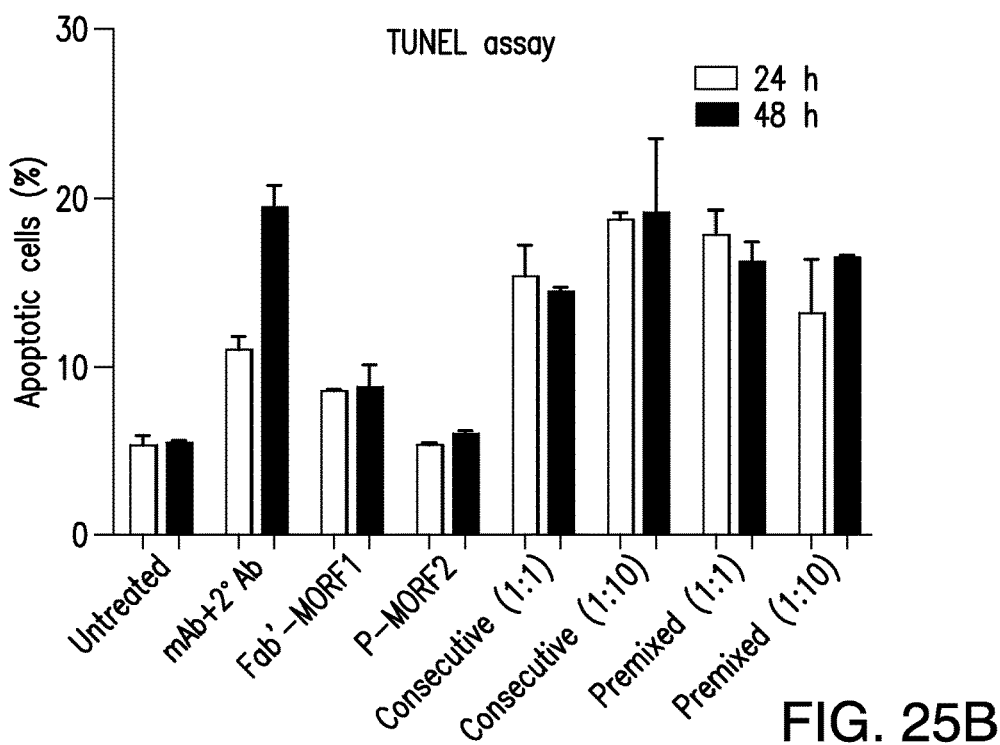

FIG. 25 shows apoptosis of Raji B-cells analyzed by different assays and at different incubation times. FIG. 25A shows caspase-3 activation assay. FIG. 25B shows TUNEL assay. Incubation time was as indicated. The following indications apply to both figures—Untreated: cells in culture medium; mAb+2° Ab: 1F5 mAb (0.5 μM) followed (1 h later) by goat anti-mouse secondary Ab (0.25 μM); Fab'-MORF1: single-component at 0.5 μM; P-MORF2: single-component of P-MORF2/v3 at 5 μM (MORF2 equivalent); Consecutive (1:1): Fab'-MORF1 (0.5 μM) followed (1 h later) by P-MORF2/v3 (0.5 μM MORF2-eqv.); Consecutive (1:10): Fab'-MORF1 (0.5 μM) followed (1 h later) by P-MORF2/v3 (5 μM MORF2-eqv.); Premixed (1:1): premixture of Fab'-MORF1 (0.5 μM) and P-MORF2/v3 (0.5 μM MORF2-eqv.); Premixed (1:10): premixture of Fab'-MORF1 (0.5 μM) and P-MORF2/v3 (5 μM MORF2-eqv.). Apoptotic cells percentage was quantified by flow cytometry. Data are presented as mean±SD (n=3). The apoptotic levels of Raji cells resulted from treatments of equimolar MORF1/MORF2 (1:1) were similar as those using 10-time excess P-MORF2 (1:10). This indicated saturation of the MORF1 binding sites on the surfaces of the Fab'-MORF1-decorated cells.

(7) Preclinical Evaluation in a Murine Model of Human NHL

Figure 14:
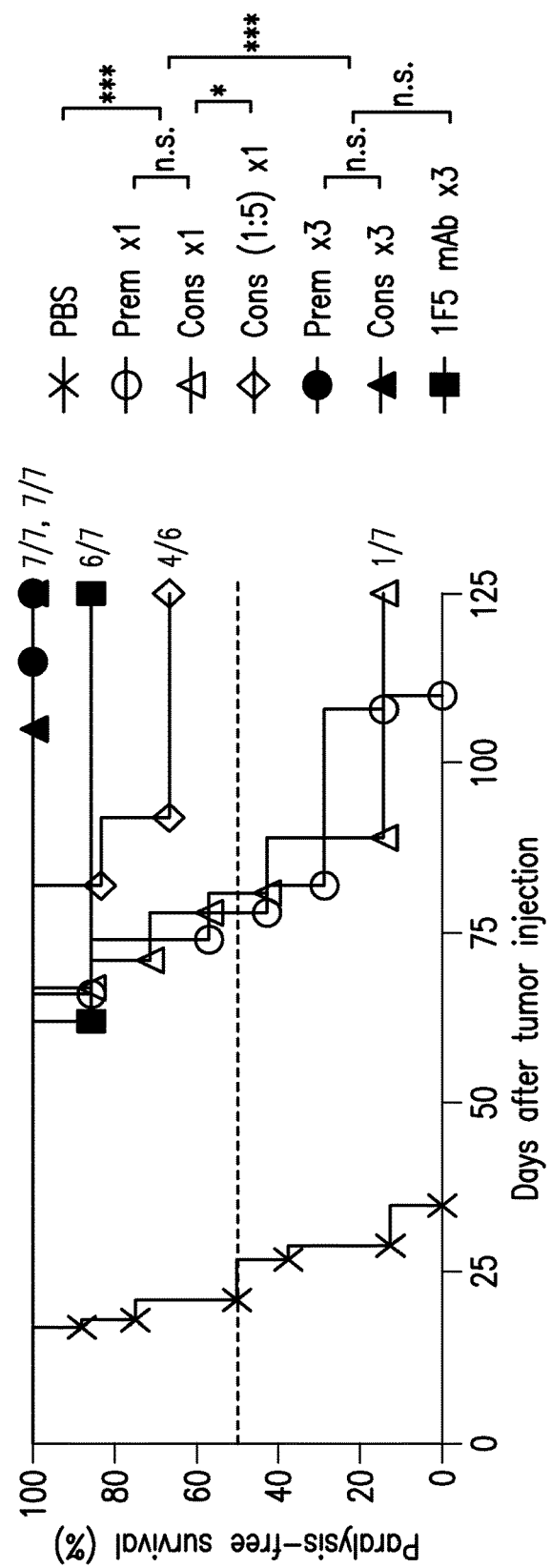
FIG. 14 shows therapeutic efficacy of the disclosed complexes and/or compositions against lymphoma in SCID mice.

In vivo therapeutic efficacy of the hybridization-mediated drug-free macromolecular therapeutics was evaluated in SCID (C.B-17) mice bearing systemically disseminated Raji B-cells. This animal model has a near 100% tumor engraftment rate (Ghetie et al., 1990), and the hind-limb paralysis-free survival time after treatment accurately reflects anticancer efficacy (Ghetie et al., 1992; Griffiths et al., 203). Four million Raji B-cells were injected via tail vein on day 0; incidence of hind-limb paralysis or survival of mice was monitored until day 125. The conjugates, Fab'-MORF1 and P-MORF2/v10, were injected via the tail vein of mice either consecutively or as a premixture. Mice divided into different groups (n=6-7) received either one or three doses of the treatment comprising disclosed compositions and complexes, starting at 24 h after tumor injection. One-dose treatment on day 1; three-dose treatment on days 1, 3, and 5. The animal survival curve is shown in FIG. 14. The negative control mice treated with PBS (n=8) developed hind-limb paralysis in 17-35 days after injection of cancer cells; the median survival time was 24 days. This observation was in agreement with the literature (Griffiths et al., 2003; Wu et al., 2012). A single administration of the consecutive treatment (Cons×1; MORF1:MORF2=1:1) substantially extended the animal survival (median survival time: 81 days). A single premixed dose (Prem×1; MORF1:MORF2=1:1) had similar efficacy as the consecutive treatment, resulting in a median survival of 78 days. When the same dose of Fab'-MORF1 (57.5 μg/20 g) was given but followed by a 5-time excess P-MORF2/v10 (MORF1:MORF2=1:5), the efficacy significantly improved over the treatment with equimolar MORF1/MORF2. A single administration of such treatment (Cons (1:5)×1) produced a 67% survival rate (4/6 long-term survivors; 125 days). The discrepancy between in vivo and in vitro data (FIG. 13C), when excess P-MORF2 was used, can be explained by blood dilution of the conjugates, which interferes with binding saturation. To summarize, in FIG. 14, the following apply: PBS: mice injected with PBS (n=8); Cons×1: consecutive treatment of Fab'-MORF1 and P-MORF2/v10, 1-dose (n=7); Prem×1: premixture of Fab'-MORF1 and P-MORF2/v10, 1-dose (n=7); Cons (1:5)×1: consecutive treatment, MORF1:MORF2=1:5, 1-dose (n=6); Cons×3: 3 doses of consecutive treatment (n=7); Prem×3: 3 doses of premixture (n=7); 1F5 mAb×3: 3 doses of 1F5 mAb (n=7). The paralysis-free survival of mice is presented in a Kaplan-Meier plot. Numbers of long-term survivors in each group are indicated (if any). Statistics was performed with log-rank test (*p<0.05, ***p<0.0001, n.s.=no significant difference).

Excellent therapeutic efficacy was observed with the groups of mice that received 3 consecutive administration doses (Cons×3; n=7) or 3 premixed administration doses (Prem×3; n=7). All mice survived until the experimental endpoint (day 125). The positive control group (n=7) that received 3 equivalent doses of 1F5 mAb (i.v.) had an 86% survival rate. Although the difference to the 3-dose treatment groups (i.e., receiving disclosed compositions and complexes) is not statistically significant, the anticancer activity of the disclosed compositions and complexes, unlike mAbs, is independent of immune effector mechanisms such as antibody-dependent cellular cytotoxicity (ADCC) and complement-dependent cytotoxicity (CDC) (Okroj et al., 2013). These data indicated that the disclosed direct apoptosis induction system can be as effective as the immunotherapy while simultaneously reducing the concerns of side effects that are mostly associated with ADCC and CDC (van der Kolk et al., 2001; Okroj et al., 2013).

(8) Analysis of In Vivo Anti-Lymphoma Efficacy

Figure 15A:
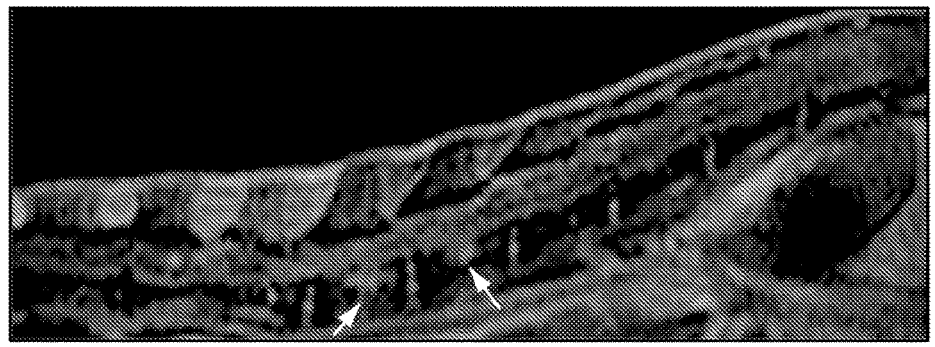
FIG. 15A-FIG. 15E shows the eradication of Raji cells in SCID mice using disclosed complexes and/or compositions.
Figure 15B:
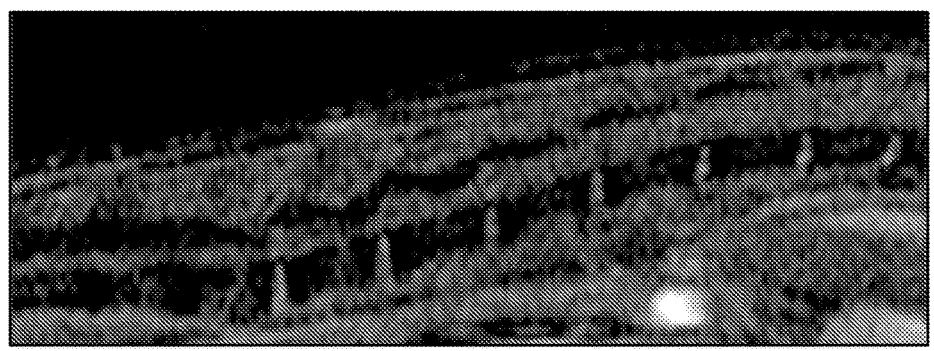
Figure 15C:
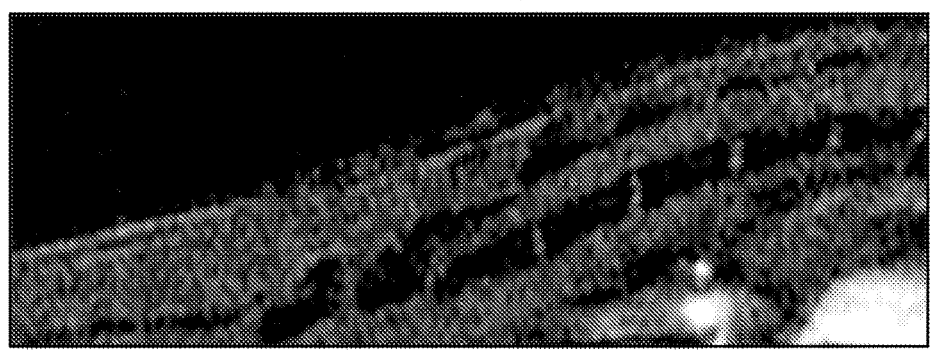

Mice i.v. injected with $4\times10^6$ Raji B-cells on day 0 were exposed to different treatments—PBS: mice injected with PBS; Cons×3: consecutive treatment of Fab'-MORF1 and P-MORF2/v10 on days 1, 3, and 5; Prem×3: 3 doses of the premixture of Fab'-MORF1 and P-MORF2/v10 on days 1, 3, and 5. The eradication of Raji cells in SCID mice after treatment with Fab'-MORF1 and P-MORF2 was confirmed by MRI, flow cytometry, and histology. MRI with gadolinium-based contrast at 4-5 weeks after injection of cancer cells showed that the control mice treated with PBS developed tumors in the lumbar spinal cord (FIG. 15A), whereas three doses of the disclosed compositions and complexes prevented tumor development (FIG. 15B-FIG. 15C). FIG. 15A-FIG. 15C show post-contrast $T_1$-weighted sagittal MRI focusing on the lumbar spine of mice. A heterogeneous appearance and irregularly shaped masses indicating tumor nodules (red arrows) were observed in the spinal cord of control mice (PBS, n=4, FIG. 15A), but not in the treated mice (Cons×3 and Prem×3, n=4). The surviving mice treated with Cons×3 (FIG. 15B) or Prem×3 (FIG. 15C) were imaged again on week-16; no relapse of the disease was observed (FIG. 26A-FIG. 26C).

Figure 26C:
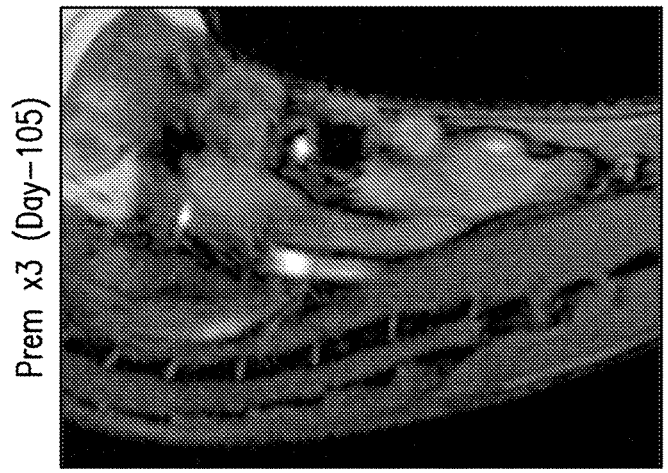
FIG. 26A-FIG. 26C show post-contrast $T_1$-weighted sagittal MRI of mice injected with Raji B-cells and exposed to different treatments.
Figure 26B:
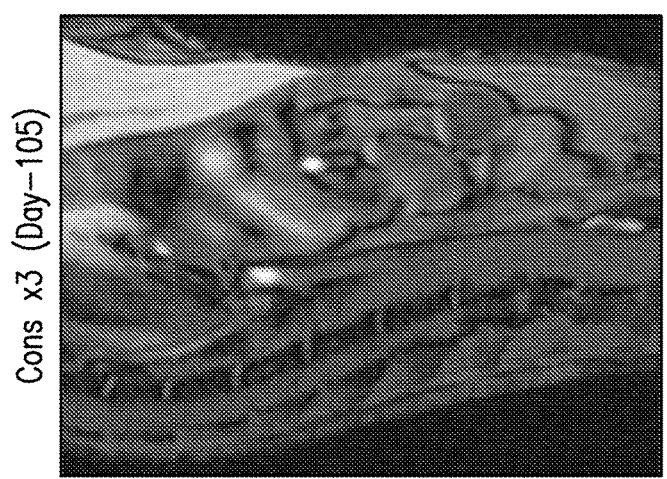
Figure 26A:
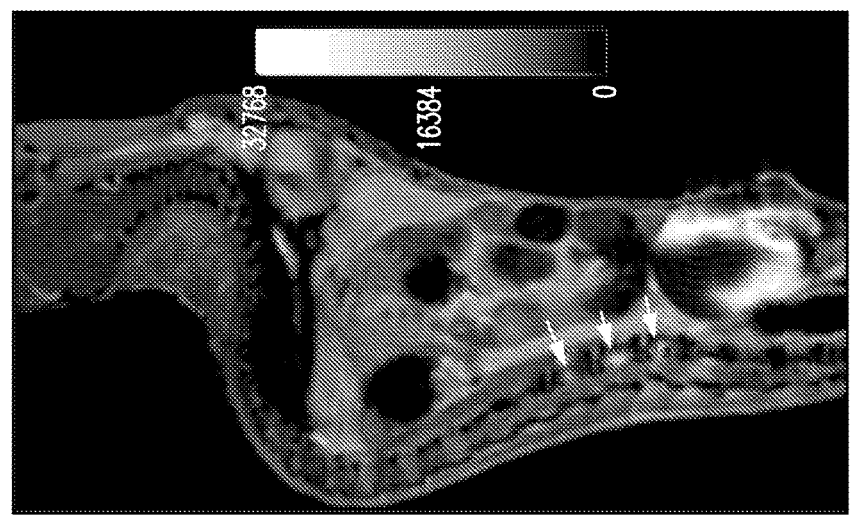

FIG. 26 shows post-contrast $T_1$-weighted sagittal MRI of mice injected with Raji B-cells and exposed to different treatments. FIG. 26A shows control mice treated with PBS developed tumors in the lumbar spinal cord, characterized by a heterogeneous appearance and irregularly-shaped masses indicating tumor nodules (arrows). A grey scale bar indicating the range of the MR signal intensity (arbitrary unit) is shown. FIG. 26B shows MR images of the mice treated with the disclosed compositions and complexes (Cons×3) and FIG. 26C shows MR images of mice treated with the disclosed compositions and complexes (Prem×3) focusing on the lumbar spine. Imaging was performed on day 105 after the injection of cancer cells; no tumors were found in any of the scanned mice (n=4).

Figure 15D:
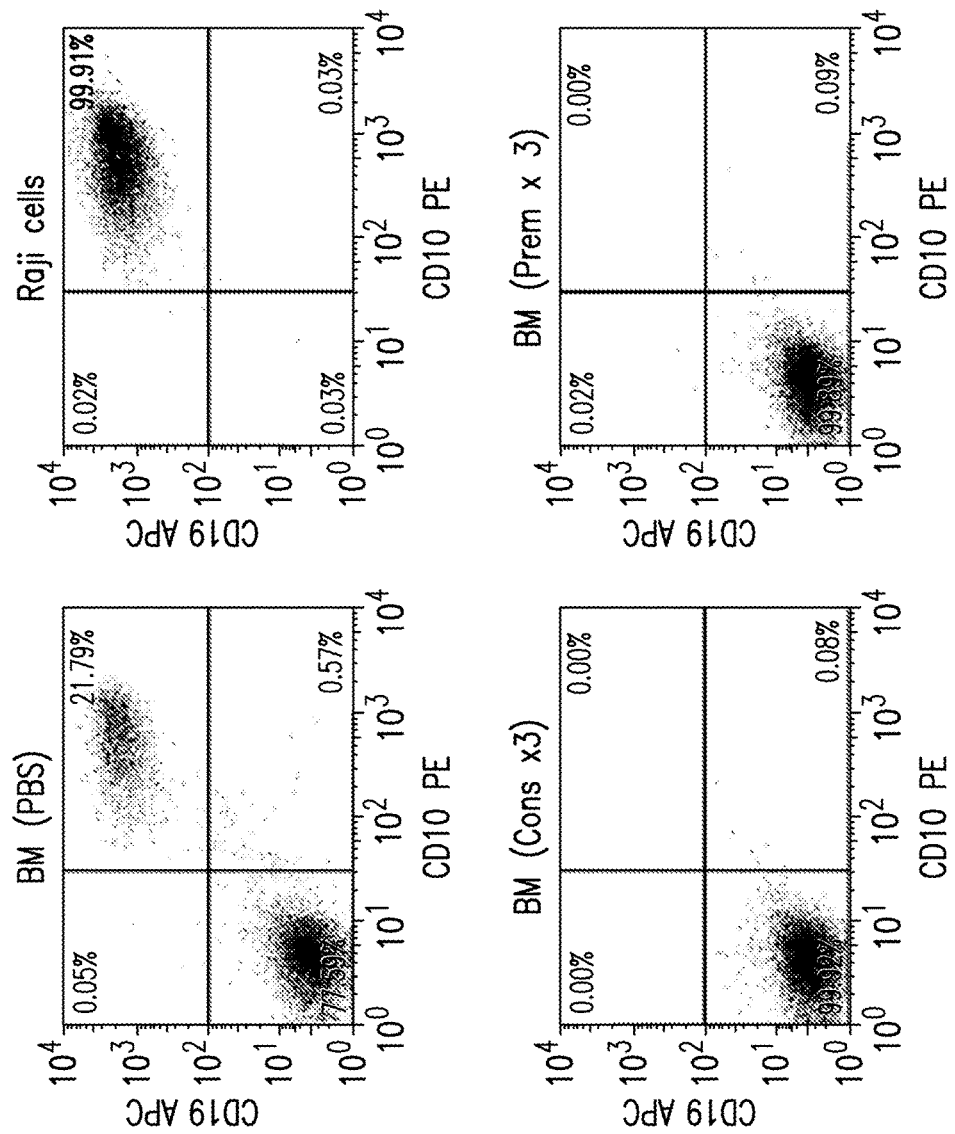
Figure 15E:
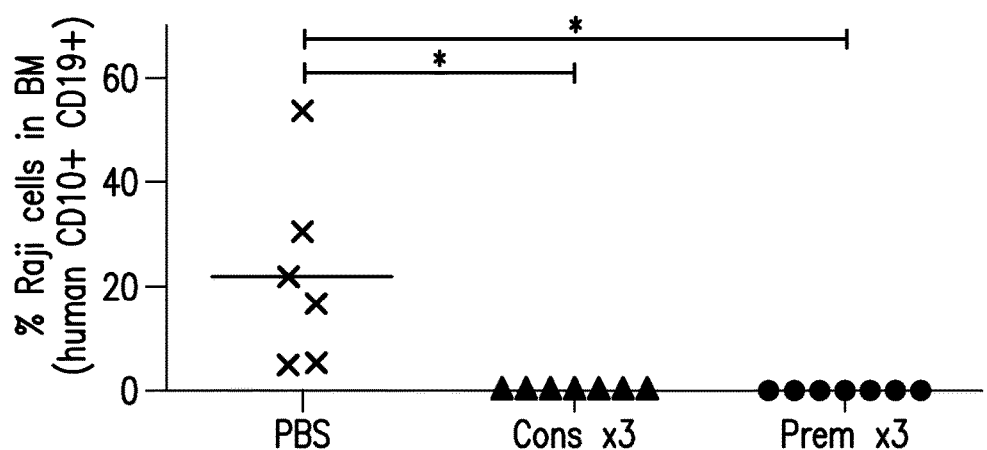

After the mice were sacrificed, flow cytometry was performed to analyze residual Raji cells (human $CD10^+ CD19^+$) in the femoral bone marrow (FIG. 15D). Two fluorescently labeled antibodies, PE-labeled mouse anti-human CD10 and APC-labeled mouse anti-human CD19, were used for flow cytometry analysis (Wu et al., 2012; Chen et al., 2010). Results indicated that the paralyzed animals (PBS-treated) bore significant amounts of Raji cells in the bone marrow (obtained from the femur), while all long-term survivors in the therapy groups (Cons×3 and Prem×3) were tumor free (FIG. 15E). Flow cytometry also confirmed Raji cells in the spinal cord of paralyzed mice (PBS-treated), but not in the long-term survivors (FIG. 27A-FIG. 27F), which was in agreement with MRI data. Furthermore, FIG. 15E shows the quantitative comparison of % Raji cells (human $CD10^+$ $CD19^+$) in the bone marrow of control mice (PBS, n=6) and the mice treated with the disclosed compositions and complexes (Cons×3 and Prem×3, n=7 per group) as analyzed by flow cytometry (FIG. 15D). Each data point represents an individual mouse; mean % is indicated. Statistics was performed by Student's t test of unpaired samples (*$p<0.05$).

FIG. 27 shows flow cytometry analysis of residual Raji B-cells in different organs/tissues of the tumor-bearing mice that underwent different treatments. FIG. 27 shows cells isolated from the inguinal and mesenteric lymph nodes (LN) of mice and treated with PBS (FIG. 27A), three consecutive treatments (FIG. 27B), and the pre-mixed treatments (FIG. 27C). FIG. 27 also shows Cells isolated from the spinal cord (SC) of mice treated with PBS (FIG. 27D), three consecutive treatments (FIG. 27E), and the pre-mixed treatments (FIG. 27F). These cells were stained with PE mouse anti-human CD10 and APC mouse anti-human CD19 antibodies; upper right quadrant ($CD10^+ CD19^+$) represents Raji cells. Results indicated that the PBS-treated, paralyzed mice (PBS) bore Raji cells in both LN (n=6) and SC (n=3), while the long-term survivors in the therapy groups (Cons×3, Prem×3; FIG. 27B, FIG. 27C, FIG. 27E, and FIG. 27F) were tumor free (n=6 per group).

Figure 16A:
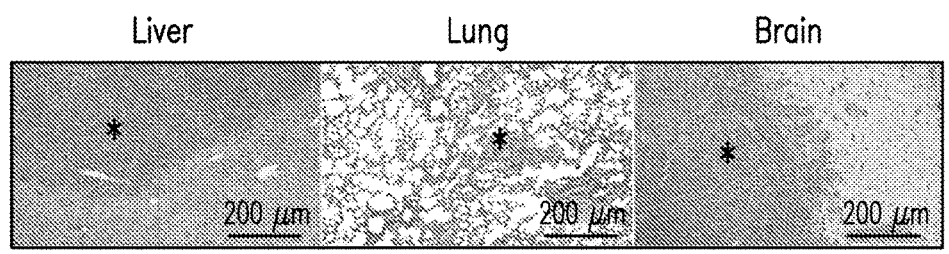
FIG. 16A-FIG. 16C shows a histopathological examination of mice following treatment with PBS and Fab'-MORF1 and P-MORF2.
Figure 16B:
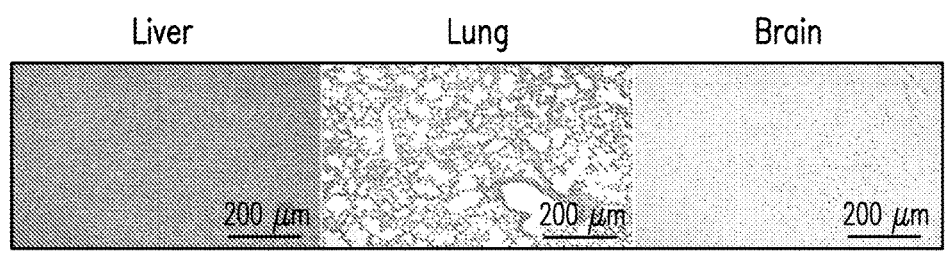
Figure 16C:
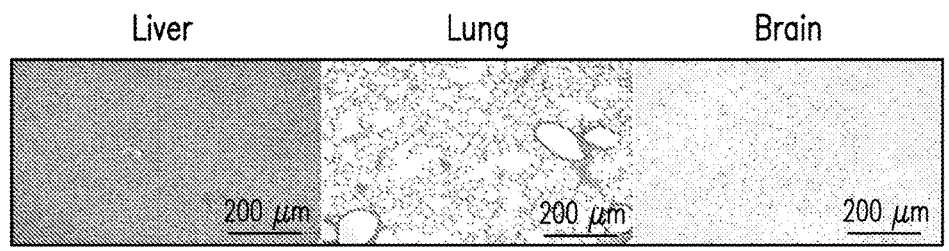
Figure 28:
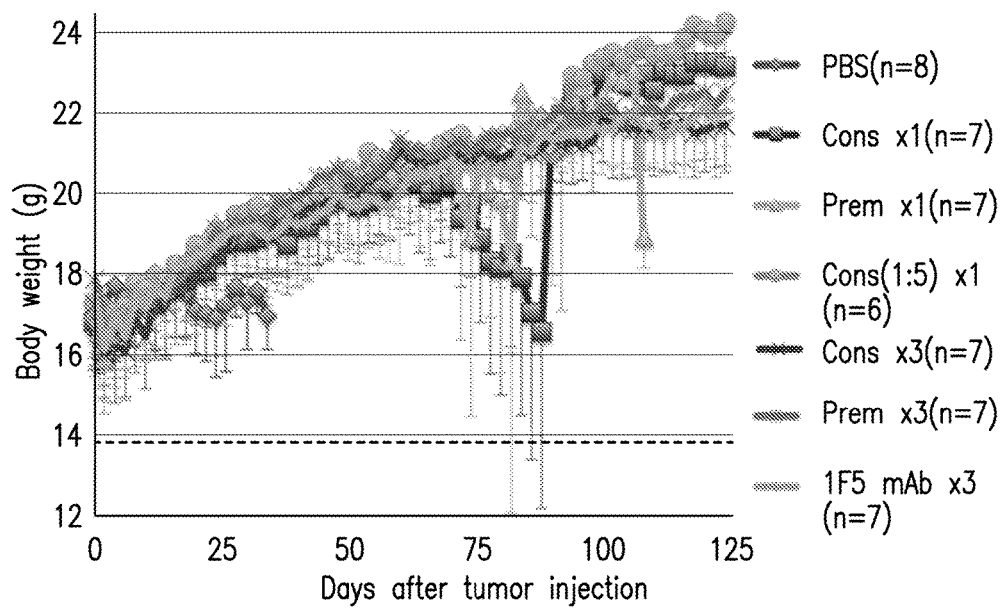
FIG. 28 shows body weight of mice injected with Raji B-cells and exposed to different treatments.

Furthermore, histological examination disclosed lymphoma dissemination in the liver, lung, and brain of PBS-treated mice (FIG. 16A-FIG. 16C). In contrast, no tumors were found in the long-term survivors. Toxicity caused by the treatments in any of the tissues was not detected; as evidenced by histology and a stable body weight growth of the treated animals (FIG. 28). FIG. 28 shows the body weight of mice injected with Raji B-cells via tail vein and exposed to different treatments. Single-dose administration was on day 1; three-doses were administered on days 1, 3, and 5. Body weight is presented as mean-SD. A black dashed line indicating 80% of the initial averaged body weights of all mice is shown. These results indicated that the disclosed compositions and complexes successfully inhibited lymphoma cell growth/dissemination in vivo without acute toxicity. In FIG. 16A, control mice that were injected with Raji cells and treated with PBS developed metastatic tumors in the liver (2 mice found with tumors/4 mice examined), lung (3/4), and brain (1/4), as demonstrated by invasion of monomorphic lymphoma cells (asterisks) and disruption of normal tissue architecture. In FIG. 16B, three doses of the consecutive treatment of Fab'-MORF1 and P-MORF2 (Cons×3) resulted in no evidence of lymphoma invasion (0/3, for all organs). In FIG. 16C, three doses of the premixed treatment (Prem×3) prevented lymphoma dissemination (0/3, for all organs). Hematoxylin and eosin (H&E)-stained tissue specimens were examined by a blinded veterinary pathologist. No toxicity of the treatment was indicated in any of the organs evaluated.

(9) Relevant Materials and Methods (a) MORF1 and MORF2

The two complementary 3'-amine-derivatized 25-mer phosphorodiamidate morpholino oligomers were from Gene Tools, LLC (Philomath, Oreg.). MORF1: 5'-GAGTAAGC-CAAGGAGAATCAATATA-linker-amine-3' (MW=8630.5 Da); MORF2: 5'-TATATTGATTCTCCTTGGCTTACTC-linker-amine-3' (MW=8438.5 Da). Structure of the linker is shown FIG. 2. For the design of base sequences, a sequence scrambling software (http://www.sirnawizard.com/scrambled.php) and a sequence analysis software (http://www.basic.northwestern.edu/biotools/oligocalc.html) were used.

(b) Preparation of Fab'-MORF1

The 1F5 mAb was prepared from a murine hybridoma cell sub-clone 1F5 (ATCC, Bethesda, Md.) in a CellMax® bioreactor (Spectrum Laboratories, Rancho Dominguez, Calif.). Antibodies were harvested from the culture media, and purified on a Protein G Sepharose 4 Fast Flow column (GE Healthcare, Piscataway, N.J.). Preparation of Fab' from mAb followed the protocol set forth in Fowers et al., 2001. Briefly, mAb was digested into $F(ab')_2$ with 10% (w/w) pepsin (Sigma, St. Louis, Mo.) in citric buffer (pH 4.0) Immediately before conjugation, $F(ab')_2$ was reduced to Fab' by 10 mM tris(2-carboxyethyl)phosphine (Thermo Scientific, Waltham, Mass.). To prepare the Fab'-MORF1 conjugate, the MORF1 oligo containing a 3'-primary amine was reacted with succinimidyl-4-(N-maleimidomethyl)cyclohexane-1-carboxylate (SMCC) to introduce a terminal (thiol-reactive) maleimide group. This produced MORF1 with 3'-maleimide (MORF1-mal). MORF1-mal was then conjugated to Fab' (containing a terminal thiol group) via a thioether bond to obtain Fab'-MORF1. The conjugates were purified using SEC to remove free, unconjugated Fab' and MORF1.

Specifically, to prepare the Fab'-MORF1 conjugate, the following steps were performed: first, 200 nmol MORF1-$NH_2$ (containing a 3'-primary amine) (Gene Tools, Philomath, Oreg.) was reacted with 0.67 mg (2 μmol) succinimidyl-4-(N-maleimidomethyl)cyclohexane-1-carboxylate (SMCC) (Soltec Ventures, Beverly, Mass.) in 170 μL DMSO to produce the MORF1-mal (containing a 3'-maleimide). The reaction was performed at RT (room temperature) for 24 h. The product was isolated by precipitation into 1.5 mL acetone, purified by dissolution-precipitation in deionized water-acetone twice, and dried under vacuum. Second, 200 nmol MORF1-mal was dissolved in 200 μL 10 mM PBS (pH 6.5), and then the solution was mixed with 200 nmol (~10 mg) freshly reduced Fab'-SH in 2 mL PBS (pH 6.5). The reaction was performed at 4° C. for 24 h. Finally, the Fab'-MORF1 conjugate was purified using size exclusion chromatography (SEC) to remove free, unconjugated Fab' and MORF1. An ÄKTA FPLC system (GE Healthcare, Piscataway, N.J.) equipped with Sephacryl S-100 HR16/60 column (GE Healthcare) eluted with PBS (pH 7.2) was used. Optionally, Fab'-MORF1 was labeled with 5-10 molar excess Rhodamine Red™-X succinimidyl ester (R6010) (Molecular Probes®, Invitrogen, Carlsbad, Calif.) for imaging studies. The product was purified using a PD-10 desalting column (GE Healthcare). To determine Fab' equivalent concentration of the Fab'-MORF1 conjugate, a bicinchoninic acid (BCA) protein assay (Thermo Scientific Pierce, Rockford, Ill.) was used. The obtained values were compared to the MORF1 equivalent concentrations obtained from UV-visible spectroscopy (using a molar absorptivity of 278,000 $M^{-1}$ $cm^{-1}$). Such comparison confirmed a 1:1 stoichiometry of the coupling reaction.

(c) Preparation of P-MORF2

The polymer precursors (P-TT and P-TT-FITC), namely, copolymers of N-(2-hydroxypropyl)methacrylamide (HPMA), N-methacryloylglycylglycine thiazolidine-2-thione (MA-GG-TT), and optionally N-methacryloylaminopropyl fluorescein thiourea (MA-FITC), were synthesized by RAFT copolymerization. 2,2'-Azobis[2-(2-imidazolin-2-yl)propane]dihydrochloride (VA-044; Wako Chemicals, Richmond, Va.) was used as the initiator, and 4-cyanopentanoic acid dithiobenzoate (CPDB) as the chain transfer agent. CPDB (Pan et al., 2011) and monomers HPMA (Kopecek et al., 1973), MA-GG-TT (Subr et al., 2006), and MA-FITC (Omelyaneko et al., 1998) were synthesized.

The multivalent P-MORF2 conjugates were prepared in two steps. First, the polymer precursors (P-TT), namely, copolymers of N-(2-hydroxypropyl)methacrylamide (HPMA), N-methacryloylglycylglycine thiazolidine-2-thione (MA-GG-TT), and optionally (for imaging studies only) N-methacryloylaminopropyl fluorescein thiourea (MA-FITC) were synthesized by RAFT copolymerization. Second, P-TT was reacted with MORF2-$NH_2$ to produce multivalent P-MORF2.

Regarding the synthesis of P-TT, in RAFT copolymerization, 4-cyanopentanoic acid dithiobenzoate (CPDB) was used as the chain transfer agent, and 2,2'-azobis[2-(2-imidazolin-2-yl)propane]dihydrochloride (VA-044) as the initiator. The reaction was carried out in methanol containing 0.3% (v/v) acetic acid (MeOH/H+). A typical procedure was as follows: HPMA (272 mg, 1.9 mmol) and MA-GG-TT (30.1 mg, 0.1 mmol) were added into an ampoule attached to an Schlenk-line. After three vacuum-nitrogen cycles to remove oxygen, 1 mL degassed MeOH/H+ was added to dissolve monomers, followed by addition of CPDB solution (0.43 mg in 50 μL MeOH/H+) and VA-044 solution (0.25 mg in 50 μL MeOH/H+) via syringe. The mixture was bubbled with nitrogen for 15 min before sealing the ampoule; the copolymerization was performed at 40° C. for 36 h. The copolymer was isolated by precipitation into acetone and purified by dissolution-precipitation in methanol-acetone twice and dried under vacuum. Yield of P-TT was 160 mg (53%). The number average molecular weight (Mn) and molecular weight distribution (polydispersity, Pd) of P-TT were determined by SEC, using ÄKTA FPLC equipped with miniDAWN and OptilabREX detectors (GE Healthcare). Superose 6 HR10/30 column (GE Healthcare) was used, with sodium acetate buffer (pH 6.5) and 30% acetonitrile (v/v) as mobile phase. To remove the terminal (active) dithiobenzoate groups, P-TT copolymers were reacted with 2,2'-azobis(2,4-dimethyl valeronitrile) (V-65) (Wako Chemicals, Richmond, Va.). Briefly, P-TT (39 mg, Mn=92 kDa, ~0.42 mmol) and V-65 (20× excess, 2.1 mg, ~8.47 mmol) were added into an ampoule. After three vacuum-nitrogen cycles to remove oxygen, 0.4 mL MeOH/H+ was added. The solution was bubbled with nitrogen for 15 min, sealed, and reacted at 50° C. for 3 h. The end-modified copolymer was purified by precipitation into acetone twice and then dried under vacuum (yield 34 mg, or 86%). The content of TT groups in the copolymers was determined by UV absorbance at 305 nm (molar absorptivity=10,900 M-1 cm-1; in methanol) (Subr et al., 2006). The content of FITC was determined by absorbance at 495 nm (molar absorptivity=82,000 M-1 cm-1; in borate buffer pH 9.2+10% (v/v) DMF) (Omelyanenko et al., 1998).

Regarding the attachment of MORF2-$NH_2$ to P-TT to produce P-MORF2, the P-TT described above was reacted with MORF2-$NH_2$ to produce multivalent P-MORF2. For example, the following steps were performed: 10 mg P-TT (92 kDa; containing 3.83 μmol TT groups) was mixed with 6.46 mg (766 nmol) MORF2-$NH_2$ in 400 μL 10 mM PBS (pH 7.4). The solution mixture in an ampoule was stirred at RT for 24 h; then 1 μL 1-amino-2-propanol (Sigma-Aldrich, St. Louis, Mo.) was added and stirred for another 15 min to aminolyze unreacted TT groups on the polymer chains. After reaction, the solution was filtered through a 0.22 μm filter, and the conjugate was purified by SEC using ÄKTA FPLC with Superose 6 HR16/60 column (GE Healthcare) eluted with PBS (pH 7.2). P-MORF2 was characterized by UV absorbance at 265 nm after removal of unconjugated MORF2 (if any). To quantify the content of MORF2 and determine the valence (number of MORF2 per polymer chain), the fractionated P-MORF2 conjugates were freeze-dried and dissolved in 0.1 N HCl prior to UV-Vis analysis. A molar absorptivity of 252,000 ($M^{-1}$ $cm^{-1}$) was used for quantification of MORF2. The valences of the P-MORF2 conjugates were calculated based on the resulting MORF2 contents and the Mn of the polymer backbones (as previously determined by SEC).

(d) Characterization of Fab'-MORF1 and P-MORF2

UV-visible spectroscopy was used for quantification of MORF1 and MORF2 oligos as well as for the determination of the content of MORFs in the conjugates. The molar absorptivities of MORF1 and MORF2 (at 265 nm, in 0.1 N HCl) were 278,000 and 252,000 ($M^{-1}$ $cm^{-1}$), respectively.

The valence of the P-MORF2 conjugates was determined using the extinction coefficient of MORF2 and the Mn's of the polymer backbones. The MORF2 equivalent concentration of P-MORF2 conjugates was quantified using UV-visible spectroscopy. The Fab' equivalent concentration of the Fab'-MORF1 conjugate was quantified by the bicinchoninic acid (BCA) protein assay (Thermo Scientific Pierce, Rockford, Ill.).

Analysis of the hypochromic effect upon MORF1-MORF2 hybridization was performed using a Varian Cary 400 Bio UV-visible spectrophotometer (Agilent Technologies, Santa Clara, Calif.). MORF1 and MORF2 (or Fab'-MORF1 and P-MORF2) were firstly dissolved in 1 mL PBS (pH=7.4) each at a concentration of 2.5 µM (MORF equivalent) and then mixed in different ratios. The final concentrations of MORF oligos (MORF1+MORF2) in every solution mixture were kept constant (2.5 µM). For example, the mixture containing 75% MORF1 (or 25% MORF2) was done by mixing 0.75 mL of 2.5 µM MORF1 solution with 0.25 mL of 2.5 µM MORF2 solution. Samples were placed in a 1-cm quartz cuvette for measurement. The optical density (OD) at 260 nm (contributed by bases) was recorded. All measurements were performed in triplicate.

The hydrodynamic effective diameters of the conjugates, Fab'-MORF1 and P-MORF2, and their precursors, Fab'-SH and P-TT, were analyzed by DLS (dynamic light scattering) using a Brookhaven BI-200SM goniometer and BI-9000AT digital correlator equipped with a He—Ne laser ($\lambda$=633 nm) at RT in PBS (pH 7.4). The scattering angle was 90°. A Nanosphere™ polystyrene size standard with a diameter of 102±3 nm (STD100 nm) (Thermo Scientific, Waltham, Mass.) was measured in line. Conjugates and precursors at a concentration of about 1 mg/mL were filtered through a 0.22 µm filter prior to measurement. All samples showed a polydispersity less than 0.2, and the mean particle diameters were recorded. Furthermore, DLS was used to characterize the change of particle size upon the binding of Fab'-MORF1 and P-MORF2. The analysis was performed at different times (10 min, 30 min, and 60 min) after mixing the two conjugates (at equimolar MORF1/MORF2 concentrations). All samples contained a major population of particles (polydispersity <0.2) indicating the hybridized conjugates, as well as minor populations indicating unbound Fab'-MORF1 and P-MORF2. The mean effective diameter of the major population was recorded. All measurements were performed in triplicate.

An Aviv 62DS CD spectrometer with a thermoelectric temperature control system (Aviv Biomedical, Lakewood, N.J.) was used. Regular measurements (excluding thermal melting analysis) were carried out at 25° C. where each sample was scanned from 200 to 340 nm with 1 nm/step (bandwidth=1 nm, each step=2 sec). Samples were prepared in 10 mM PBS (pH 7.4) at 50 µM MORF equivalent concentrations (Fab'-SH at 50 µM Fab'-eqv.). Prior to measurement, samples were filtered through a 0.22 µm filter and placed in a 0.1-cm path length quartz cuvette. The obtained spectra were subtracted from the background (PBS pH=7.4); data from three sequential scans were averaged. For thermal melting studies, the CD signal at 260 nm was recorded (n=3).

Fab'-MORF1 and P-MORF2 (or MORF1 and MORF2) were mixed in equimolar ratio (5 µM/5 µM MORF1/MORF2) in PBS pH=7.4 for 1 h at RT. The solution mixtures were filtered and placed in a 1-cm path length quartz cuvette prior to measurement. Each sample first underwent a forward scan where the temperature increased from 25 to 95° C. at 2° C./step. For each step, the sample was equilibrated for 2 min followed by 30 sec of data point averaging. Afterward, a reverse scan was performed where the temperature decreased from 95 to 25° C. at –10° C./step. For each step, the sample was equilibrated for 5 min followed by 30 sec of data point averaging.

The measured ellipticity ($\theta_{obs}$) was converted to molar ellipticity ($\theta$) using the following equation: $\theta=\theta obs/(l*c)$ where l is the cuvette's optical path length and c is MORF-eqv. molar concentration. To analyze melting temperature (Tm) of MORF1-MORF2 hybridization, $\theta$ (at 260 nm) was plotted against temperature (T), and the data were fitted to a thermo-melting curve by nonlinear regression (GraphPad Prism 5 software) using the following four-parameter logistic function:

$$\theta=\theta min+(\theta max-\theta min)/[1+(T/Tm)^H]$$

where $\theta_{min}$ is the minimal molar ellipticity (at 260 nm) in the curve, $\theta_{max}$ is the maximal molar ellipticity (at 260 nm) in the curve, and H is the Hill slope.

(e) Confocal Fluorescence Microscopy

Human Burkitt's B-cell non-Hodgkin's lymphoma Raji cell line (ATCC, Bethesda, Md.) was cultured in RPMI-1640 medium (Sigma, St. Louis, Mo.) supplemented with 10% fetal bovine serum (Hyclone, Logan, Utah) at 37° C. in a humidified atmosphere with 5% $CO_2$ (v/v). All experiments were performed using cells in exponential growth phase. For the consecutive treatment, cells at a density of $10^6$ per well were incubated with 0.4 mL Fab'-MORF1-RHO (0.4 µM Fab' equivalent) in culture medium at 37° C. for 1 h; then the cells were washed twice with PBS prior to incubation with 0.4 mL of P-MORF2-FITC (0.4 µM MORF2 equivalent) for another 1 h. For the premixed treatment, Fab'-MORF1-RHO and P-MORF2-FITC were firstly mixed in culture medium in equimolar concentrations (0.4 µM) for 1 h; then cells at the same density were incubated with 0.4 mL of the premixture solution for 1 h. After incubation, the cells were washed twice with PBS (to discard the media that contained the conjugates), and then plated onto sterile 35-mm glass bottom dishes with 14-mm microwells (MatTek Corporation, Ashland, Mass.) for imaging, using Olympus laser scanning confocal microscope (FV 1000). For control studies, concentrations of all corresponding components were kept consistent; excess amounts of P-FITC and P-dsMORF were used. Prior to analysis, cells incubated with FITC-labeled 1F5 mAb, rhodamine-labeled F(ab')$_2$, and PBS were used to adjust channel setting and confirm CD20 binding.

(f) Evaluation of In Vitro Apoptosis

Apoptosis of human NHL B-cells was evaluated by three methods: caspase-3 assay, annexin V/PI assay, and TUNEL assay. These assays evaluated apoptosis from different aspects—levels of caspase-3 activation represented apoptotic protein expression; annexin V/PI binding characterized cell membrane flipping as an early apoptotic event; TUNEL assay analyzed genomic DNA fragmentation as a late apoptotic event. Quantification of apoptotic activity (% apoptotic cells) was performed by flow cytometry.

In vitro apoptosis induction of human Burkitt's B-cell non-Hodgkin's lymphoma (NHL) Raji cells by co-treatment with Fab'-MORF1 and P-MORF2 was evaluated by three assays: caspase-3 activation assay, annexin V/propidium iodide (PI) binding assay, and TUNEL (terminal deoxynucleotide mediated-dUTP nick-end labeling) assay. In all experiments, 1F5 mAb hyper-cross-linked with a goat anti-mouse (GAM) secondary antibody (2° Ab) (KPL, Gaithersburg, Md.) was used as a positive control (molar ratio 1F5:GAM=2:1). Untreated cells (in culture media) were used as negative controls.

To evaluate caspase-3 activity, a Phi-PhiLux kit (Oncolmmunin, Gaithersburg, Md.) was used. For the consecutive treatment, 2×10⁵ Raji cells were suspended in 0.4 mL fresh growth medium containing 0.5 µM Fab'-MORF1. The cells were incubated for 1 h in a humidified atmosphere at 37° C. with 5% $CO_2$, and then washed twice with PBS+1% bovine serum albumin (BSA), followed by re-suspension in 0.4 mL medium containing 0.5 µM or 5 µM (MORF2-eqv.) P-MORF2. The cell suspension was incubated for 6 or 24 h. For the premixed treatment, first, 0.5 µM Fab'-MORF1 was mixed with 0.5 µM or 5 µM (MORF2-eqv.) P-MORF2 in culture medium at RT for 1 h, and then 2×10⁵ Raji cells were suspended in 0.4 mL of the premixed solution. The cell suspension was incubated for 6 or 24 h. For the positive control, cells were firstly incubated with 0.4 mL 0.5 µM of 1F5 mAb in culture medium for 1 h, and then washed twice with PBS+1% BSA, followed by re-suspension in 0.4 mL of fresh growth medium containing 0.25 µM GAM. The cells were incubated for another 6 h or 24 h at 37° C. After the treatments, cells were washed twice with PBS and analyzed for caspase-3 activity following the manufacturer's protocol. All experiments were carried out in triplicate.

Annexin V-FITC and PI staining were performed following the RAPID™ protocol provided by the manufacturer (Oncogene Research Products, Boston, Mass.). For the consecutive treatment, 2×10⁵ Raji or DG75 (CD20 negative; control) cells were suspended in 0.4 mL fresh growth medium containing 0.5, 1, 2 or 5 µM Fab'-MORF1. The cells were incubated for 1 h in a humidified atmosphere at 37° C. with 5% $CO_2$, and then washed twice with PBS+1% bovine serum albumin (BSA), followed by re-suspension in 0.4 mL medium containing 0.5 µM, 1 µM, 2 µM, or 5 µM (MORF2-eqv.) of P-MORF2. The cell suspension was incubated for 24 h or 48 h. For the premixed treatment, first, 0.5 µM, 1 µM, 2 µM, or 5 µM Fab'-MORF1 was mixed with 0.5 µM, 1 µM, 2 µM, or 5 µM (MORF2-eqv.) P-MORF2 in culture medium at RT for 1 h, and then 2×10⁵ Raji or DG75 cells were suspended in 0.4 mL of the premixed solution. The cell suspension was incubated for 24 or 48 h. For the positive control, cells were firstly incubated with 0.4 mL 0.5 µM, 1 µM, 2 µM, or 5 µM of 1F5 mAb in culture medium for 1 h, and then washed twice with PBS+1% BSA, followed by re-suspension in 0.4 mL of fresh growth medium containing 0.25 µM, 0.5 µM, 1 µM, or 2.5 µM GAM. The cells were incubated for another 24 h or 48 h at 37° C. Prior to staining, cells were washed twice with PBS. All experiments were carried out in triplicate.

For the TUNEL assay, an Apo Direct TUNEL kit (Phoenix Flow Systems, San Diego, Calif.) was used. For the consecutive treatment, 10⁶ Raji cells were suspended in 0.5 mL fresh growth medium containing 0.5 µM Fab'-MORF1. The cells were incubated for 1 h in a humidified atmosphere at 37° C. with 5% $CO_2$, and then washed twice with PBS+1% bovine serum albumin (BSA), followed by re-suspension in 0.5 mL medium containing 0.5 µM or 5 µM (MORF2-eqv.) P-MORF2. The cell suspension was incubated for 24 or 48 h. For the premixed treatment, first, 0.5 µM Fab'-MORF1 was mixed with 0.5 µM or 5 µM (MORF2-eqv.) P-MORF2 in culture medium at RT for 1 h, and then 10⁶ Raji cells were suspended in 0.5 mL of the premixed solution. The cell suspension was incubated for 24 or 48 h. For the positive control, cells were firstly incubated with 0.5 mL 0.5 µM of 1F5 mAb in culture medium for 1 h, and then washed twice with PBS+1% BSA, followed by re-suspension in 0.5 mL of fresh growth medium containing 0.25 µM GAM. The cells were incubated for another 24 h or 48 h at 37° C. After the treatments, cells were washed twice with PBS and fixed with 2% paraformaldehyde in PBS for 1 h at RT. Cells were then permeabilized in 70% ethanol overnight at 4° C. Prior to analysis, nick-end labeling was performed following the manufacturer's protocol. All experiments were carried out in triplicate.

(g) Determination of In Vivo Anti-Cancer Efficacy

Female C.B-17 SCID mice (Charles River Laboratories, Wilmington, Mass.) at about 7 weeks of age were intravenously injected with 4×10⁶ Raji cells in 200 µL saline via the tail vein (day 0). This animal model represents dissemination, infiltration, and growth of lymphoma cells in various organs, including spinal cord that leads to hind-limb paralysis and subsequent animal death (Ghetie et al., 1990, 1992; Griffirths et al., 2003). The onset of hind-limb paralysis was the experimental end point; in addition, mice were sacrificed when body weight loss was >20%. Animals without signs of paralysis/sickness were kept until 125 days and considered long-term survivors. The conjugates, Fab'-MORF1 (57.5 µg/20 g; 1 nmol MORF1) and P-MORF2/v10 (22 µg/20 g; 1 nmol MORF2), were dissolved in 100 µL PBS and injected via tail vein either consecutively (1 h interval) or as a premixture (mixed 1 h prior to treatment). The inoculated mice were divided into seven groups: (1) negative control (injected with 200 µL PBS), (2) single administration of the consecutive treatment (Cons×1), (3) single administration of the premixed treatment (Prem×1), (4) consecutive treatment administered three times (Cons×3), (5) premixed treatment administered three times (Prem×3), (6) single administration of the consecutive treatment but with 5× excess P-MORF2/v10 (110 µg/20 g; 5 nmol MORF2) to Fab'-MORF1 (Cons (1:5)×1), and (7) positive control injected with 3 doses (75 µg/20 g; 1 nmol Fab'-equivalent per dose) of 1F5 mAb via tail vein. For single-dose groups, conjugates were administered on day 1 (24 h after injection of cancer cells); for multiple-dose groups, conjugates (or mAb) were given on days 1, 3, and 5. To monitor disease progression, mice (2-4 per group) were scanned by $T_1$-weighted MRI on weeks 4, 5, and 16. Gadobenate dimeglumine (MultiHance®; Bracco SpA, Milan, Italy) was injected (i.v.) at 0.3 mmol/kg 20 min prior to imaging. Pre-contrast images were used for comparison.

The therapeutic efficacy of the hybridization-mediated drug-free macromolecular therapeutics, namely, co-treatment with Fab'-MORF1 and P-MORF2, was evaluated in an animal model of advanced NHL where SCID (C.B-17) mice were intravenously transplanted with human Raji B-cells. All treatment regimens are described in the main article. Post-treatment monitoring of the animals was performed twice a day. Body weight of mice was recorded every other day. Major aspects of the mice closely assessed included: hind-limb paralysis, food/water consumption, vital signs of abnormal mobility/activity (e.g., licking, biting, scratching a particular area, and vocalizing), and physical appearance (e.g., failure to groom, unkempt appearance, abnormal resting/hunched posters, piloerection). Animals were sacrificed in the following scenarios (whichever showed up first): (1) at the onset of (hind-limb) paralysis, and (2) body weight loss exceeding 20% of the initial (one day before the injection of cancer cells) Animals without any aforementioned signs were kept until 125 days (after the injection of cancer cells) and sacrificed for further analysis.

For in vivo MRI acquisition, mice were anesthetized with 1%-2.5% isoflurane (IsoFlo®, Abbott Laboratories, Abbott Park, Ill.) in oxygen from a precision vaporizer. Mice were placed in the prone position at the coil center. A 7-Tesla Bruker BioSpec MRI scanner (Bruker Biospin, Billerica, Mass.) with a 30-cm wide cylindrical bore and a 12-cm gradient insert was used. Pre-contrast images were firstly acquired, and then mice were injected with a gadolinium-based contrast agent, gadobenate dimeglumine (Multihance®; Bracco Imaging, Milan, Italy), via tail vein at 0.3 mmol/kg (100 μL, in physiological saline). Twenty minutes after the injection, post-contrast images were acquired. During the scanning, mouse body temperature was maintained at 37° C. using a warm-air circulation system (SA Instruments, Stony Brook, N.Y.). Respiration was monitored continuously. Scanning was performed under the ParaVision® 5.1 software environment. Acquisition parameters were as follows: $T_1$-weighted FLASH sequence with retrospective gating to suppress breathing artifacts, echo time (TE) 2.9 ms, repetition time (TR) 43.2 ms, flip angle 50°, 6 sagittal plane slice with thickness 0.5 mm, matrix 256×256, field-of-view (FOV) 3 cm×3 cm, 50 repetitions. After the scanning, images were analyzed and processed on an off-line workstation (OsiriX).

(h) Flow Cytometry Analysis of Residual Raji Cells

After mice were sacrificed, the following organs/tissues were analyzed by flow cytometry for residual Raji cells: bone marrow (femur), mesenteric and inguinal lymph nodes, spinal cord, and spleen. Two fluorescently labeled antibodies, R-phycoerythrin (PE)-labeled mouse anti-human CD10 (IgG1, κ isotype) and allophycocyanin (APC)-labeled mouse anti-human CD19 (IgG1, κ isotype) (BD Biosciences, San Jose, Calif.), were used to stain Raji B-cells (Chen et al., 2010). Single-cell suspensions were prepared from the organs/tissues using the following procedures. For bone marrow, fresh femurs were purged with 1 mL PBS to obtain cell suspensions. Cells were re-suspended in 5 mL red blood cell (RBC) lysis buffer and incubated at RT for 5 min. Cells were then washed with 5 mL PBS and centrifuged to remove debris, followed by re-suspension in 400 μL cold washing buffer and equally divided into 4 tubes: (1) non-stained control, (2) CD10 singly-stained, (3) CD19 singly-stained, and (4) CD10/CD19 doubly-stained cells. For the staining, 20 μL of each antibody was added to 100 μL cell suspension containing about $10^6$ cells. Cells were incubated for 30 min at 4° C. in the dark, and washed with 1.5 mL washing buffer prior to analysis. For lymph nodes, spinal cord and spleen, a mechanical method was used. Tissues were gently disaggregated with the help of tweezers in a Petri dish containing 1 mL PBS. The suspensions were passed through a 70-μm Falcon™ cell strainer (BD Biosciences) to remove large clumps and debris, and then cells were centrifuged and re-suspended in 5 mL RBC lysis buffer. The rest of the procedures were the same as aforementioned. For flow cytometry analysis, data of $1-1.5 \times 10^5$ cells were recorded.

(i) Pathological and Histopathological Examinations

Immediately after mice were sacrificed, the following organs/tissues were harvested for pathological evaluation: brain, heart, lung, liver, spleen, kidneys, spinal cord and lymph nodes. These organs/tissues were fixed in 10% formalin overnight at RT, and then transferred and preserved in 70% ethanol. Histopathological examination was performed by a blinded veterinary pathologist at ARUP Laboratories (Salt Lake City, Utah). Sections were cut at 4-μm thickness, mounted on glass slides, and stained by hematoxylin and eosin (H&E).

(j) Statistical Analysis

All experiments in this study were at least triplicated. Quantified data were presented as mean±standard deviation (SD). Statistical analyses were performed by Student's t test to compare between two groups, or one-way analysis of variance (ANOVA) to compare three or more groups (with p value <0.05 indicating statistically significant difference). Animal survival analysis was performed with the log-rank test using the GraphPad Prism 5 software.

iii) Experimental Advantages

Disclosed herein in a system comprising hybridization-mediated cell surface antigen crosslinking and apoptosis induction. The cellular event (apoptosis) is triggered by specific biorecognition defined from the molecular level (i.e., base pairing), suitable for the design of precisely targeted therapeutics. The disclosed two-step (consecutive) treatment offers the opportunity of pretargeting (Goodwin et al., 2001; Gun et al., 2011; Zhou et al., 2009). This is an advantage over the premixed treatment and other single-component anti-CD20 constructs, such as rituximab polymers (Zhang et al., 2005) and multivalent anti-CD20 Fab'-functionalized polymers (Johnson et al., 2009, 2012; Chu et al., 2012). For example, the timing of administration of the crosslinking dose (P-MORF2) can be optimized based on biodistribution of the pretargeting dose (Fab'-MORF1), in order to achieve maximal tumor-to-tissue accumulation in individual patients and enable more efficient treatment. This approach also limits potential adverse reactions associated with off-target binding, thus being beneficial for the treatment of solid tumors as well as disseminated diseases. For blood-based cancers, the pharmacokinetics of Fab'-MORF1 and the binding kinetics of Fab'-MORF1 to diseased cells can be further studied to determine the best timing for P-MORF2 administration.

Figure 29:
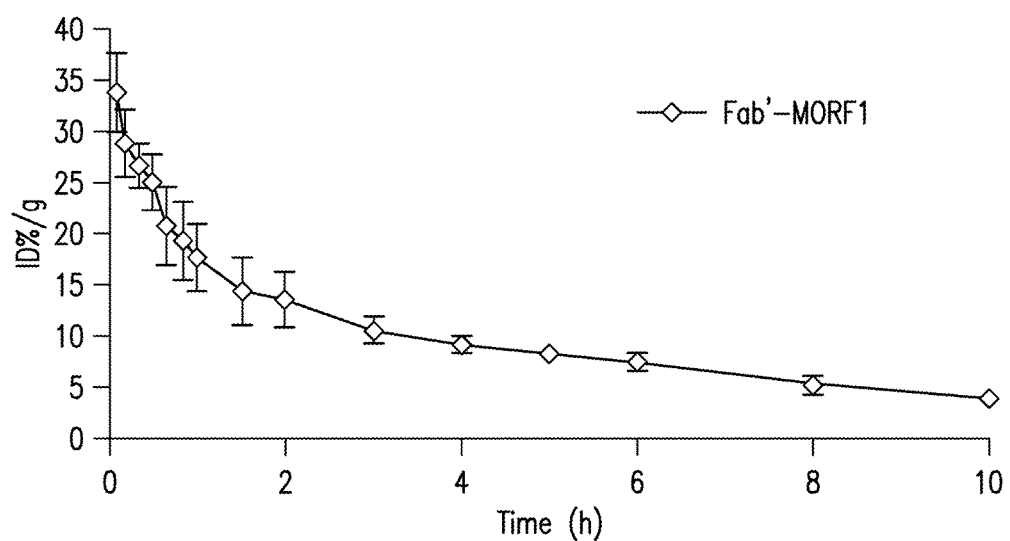
FIG. 29 shows blood activity-time profiles of $^{125}$I-labeled Fab'-MORF conjugate in SCID mice.

For example, to explore optimal administration schedule of P-MORF2 conjugate following Fab'-MORF1 in consecutive treatment, the pharmacokinetics of Fab'-MORF1 conjugate was investigated. The blood (radio)activity-time profile of $^{125}$I-labeled Fab'-MORF1 conjugate in mice is shown in FIG. 29, in which the closed circles represent the mean radioactivity, expressed as the percentage of the injected dose per gram of blood (% ID/g). Data are presented as mean±standard deviation (n=5). Results indicate that, to achieve maximal pretargeting efficiency in the consecutive treatment, P-MORF2 can be administered at ~5 h after i.v. injection of Fab'-MORF1 (when most conjugates are cleared from the blood). At this time, there is minimal free Fab'-MORF1 (unbound to B-cells) that would interfere with the hybridization. This data indicate that the therapeutic efficacy of the proposed compositions and methods can be further optimized.

Animal experiments discussed herein show that at equivalent doses, a single treatment of Fab'-MORF1+P-MORF2 (1:1) was significantly more effective than a single treatment of Fab'-CCE+P-CCK (1:25) on preventing lymphoma dissemination (consecutive treatment: 81 days median survival for MORFs vs. 50 days median survival for CCs; premixed treatment: 78 days median survival for MORFs vs. 55 days median survival for CCs). These data indicate superior binding and accessibility of the MORF oligos on the HPMA polymer chains as compared to the coiled-coil forming peptides. In addition, for the MORF1-MORF2 hybridization, a rapid binding kinetics was observed (~10 min as characterized by DLS; FIG. 11B). Conversely, the CCE-CCK coiled-coil formation required a much longer time (~60 min) (Wu et al., 2010). The comparison of CCs vs. MORFs indicates that the presently disclosed compositions, complexes, and methods are advantageous for the design of drug-free macromolecular therapeutics.

The composition, complexes, and methods disclosed herein possess at least two significant advantages: (1) superior targeting of B-cells due to multivalency, and (2) potential for decreased side effects that are associated with immune functions. When compared to previously design using peptides (i.e., anti-CD20 drug-free macromolecular therapeutic system using a pair of pentaheptad peptides that formed antiparallel coiled-coil heterodimers as the biorecognition moieties (Wu et al., 2010; Wu et al., 2012), the MORF oligos disclosed herein demonstrated faster binding kinetics, therefore resulting in superior apoptosis induction and in vivo anti-lymphoma. Other advantages of the disclosed MORF oligos include: (1) a chemically modified backbone ensuring in vivo stability (i.e., nuclease resistant), (2) a well-defined binding specificity (i.e., prevents potential off-target effects), (3) a charge-neutral property (i.e., result is in strong binding affinity), (4) a well-established safety profile (i.e., addresses the immunogenicity concern of coiled-coil peptides), and (5) a good water-solubility and favorable pharmacokinetics.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims. All of the compositions and/or methods disclosed and claimed herein can be made and executed without undue experimentation in light of the present disclosure.

F. REFERENCES

Allison M. (2010) PML problems loom for Rituxan. Nat. Biotechnol. 28:105-106.

Anderson K. C., et al. (1984) Expression of Human B Cell-Associated Antigens on Leukemias and Lymphomas: A Model of Human B Cell Differentiation. Blood 63:1424-1433.

Ben-Bassat H., et al. (1977) Establishment in Continuous Culture of a New Type of Lymphocyte from a "Burkitt Like" Malignant Lymphoma (Line D.G.-75). Int. J. Cancer 19:27-33.

Cang S, et al. (2012) Novel CD20 monoclonal antibodies for lymphoma therapy. J Hematol Oncol. 5:64.

Cartron G, et al. (2002) Therapeutic activity of humanized anti-CD20 monoclonal antibody and polymorphism in IgG Fc receptor Fcg gamma RIIIa gene. Blood 99:754-758.

Chen X, et al. (2008) Synthesis and in vitro characterization of a dendrimer-MORF conjugate for amplification pretargeting. Bioconjugate Chemistry 19(8):1518-1525.

Chen W C, et al. (2010) In Vivo Targeting of B-Cell Lymphoma with Glycan Ligands of CD22. Blood, 115:4778-4786.

Cheson B D, et al. (2008) Monoclonal Antibody Therapy for B-Cell Non-Hodgkin's Lymphoma. N. Engl. J. Med. 359:613-626.

Cho et al. (2012) A magnetic switch for the control of cell death signalling in in vitro and in vivo systems. Nature Materials 11:1038-1043.

Chu T W, et al. (2012) Anti-CD20 multivalent HPMA copolymer-Fab' conjugates for the direct induction of apoptosis. Biomaterials 33(29):7174-7181.

Chu T W, et al. (2014) Cell Surface Self-Assembly of Hybrid Nanoconjugates via Oligonucleotide Hybridization Induces Apoptosis. ACS Nano. (1):719-730.

Deans J P, et al. (2002) CD20-Mediated Apoptosis: Signalling through Lipid Rafts. Immunology, 107:176-182.

Douglas S M, et al. (2012) A Logic-Gated Nanorobot for Targeted Transport of Molecular Payloads. Science 335:831-834.

Du et al. (2009) Structure of the Fab' fragment of therapeutic antibody Ofatumumab provides insights into the recognition mechanism with CD20. Mol Immunol 46:2419-2423.

Ehrick J D, et al. (2005) Genetically Engineered Protein in Hydrogels Tailors Stimuli-Responsive Characteristics. Nat. Mater. 4:298-302.

Fowers K D, et al. (2001) Preparation of Fab' from Murine IgG2a for Thiol Reactive Conjugation. J. Drug Target. 9:281-294.

Ghetie M A, et al. (2001) Homodimers but not monomers of rituxan (chimeric anti-CD20) induce apoptosis in human B-lymphoma cells and synergize with a chemotherapeutic agent and an immunotoxin. Blood 97:1392-1398.

Ghetie M A, et al. (1990) Disseminated or Localized Growth of a Human B-Cell Tumor (Daudi) in SCID Mice. Int. J. Cancer 45:481-485.

Ghetie M A, et al. (1992) The Antitumor Activity of an Anti-CD22 Immunotoxin in SCID Mice with Disseminated Daudi Lymphoma Is Enhanced by Either an Anti-CD19 Antibody or an Anti-CD19 Immunotoxin. Blood 80:2315-2320.

Goodwin D A, et al. (2001) Advances in pretargeting technology. Biotechnol. Adv. 19:435-450.

Griffiths G L, et al. (2003) Cure of SCID Mice Bearing Human B-Lymphoma Xenografts by an Anti-CD74 Antibody-Anthracycline Drug Conjugate. Clin. Cancer Res. 9:6567-6571.

Gu Z, et al. (2005) Anti-prostate stem cell antigen monoclonal antibody 1G8 induces cell death in vitro and inhibits tumor growth in vivo via a Fc-independent mechanism. Cancer Res. 65:9495-9500.

Gungormus, M., et al. (2010) Self Assembled Bi-Functional Peptide Hydrogels with Biomineralization-Directing Peptides. Biomaterials 31:7266-7274.

Gunn J, et al. (2011) A Pretargeted Nanoparticle System for Tumor Cell Labeling. Mol. Biosyst. 7:742-748.

He J, et al. (2004) Amplification targeting: a modified pretargeting approach with potential for signal amplification-proof of a concept. J Nuclear Medicine 45(6):1087-1095.

He J, et al. (2007) An Improved Method for Covalently Conjugating Morpholino Oligomers to Antitumor Antibodies. Bioconjugate Chemistry 18:983-988.

Herter S, et al. (2013) Preclinical Activity of the Type II CD20 Antibody GA101 (Obinutuzumab) Compared with Rituximab and Ofatumumab In Vitro and in Xenograft Models. Mol. Cancer Ther. 12:2031-2042.

Holmes T C, et al. (2000) Extensive Neurite Outgrowth and Active Synapse Formation on Self-Assembling Peptide Scaffolds. Proc. Natl. Acad. Sci. U.S.A. 97:6728-6733.

Huang, et al. (2012) Multivalent structure of galectin-1-nanogold complex serves as potential therapeutics for rheumatoid arthritis by enhancing receptor clustering. Eur. Cells and Materials J. 23:170-181.

Inoue S, et al. (2011) Polymalic acid-based nanobiopolymer provides efficient systemic breast cancer treatment by inhibiting both HER2/neu receptor synthesis and activity. Cancer Research 71(4):1454-1464.

Johnson R N, et al. (2012) Biological activity of anti-CD20 multivalent HPMA copolymer-Fab' conjugates. Biomacromolecules 13:727-735.

Johnson R N, et al. (2009) Synthesis and evaluation of multivalent branched HPMA copolymer-Fab' conjugates targeted to the B-cell antigen CD20. Bioconjugate Chem. 20:129-137.

Johnson W C. (2000) CD of Nucleic Acids. In Circular Dichroism: Principles and Applications; Berova, N., et al., Eds.; Wiley-VCH: New York, ed. 2:703-718.

Kahn C R, et al. (1978) Direct Demonstration That Receptor Crosslinking or Aggregation Is Important in Insulin Action. Proc. Natl. Acad. Sci. U.S.A. 75:4209-4213.

Kamei K, et al. (2010) Severe Respiratory Adverse Events Associated with Rituximab Infusion. Pediatr. Nephrol. 25:1193.

Kimby E. (2005) Tolerability and Safety of Rituximab (MabThera). Cancer Treat. Rev. 31:456-473.

Kopeček J, et al. (2010) HPMA copolymers: origins, early developments, present, and future. Adv. Drug Deliv. Rev. 62:122-149.

Kopeček J, et al. (2012) Smart self-assembled hybrid hydrogel biomaterials. Angew Chem Int Ed Engl. 51(30):7396-417.

Kopeček J. (2013) Polymer-drug conjugates: Origins, progress to date and future directions. Adv. Drug Deliv. Rev. 65:49-59.

Kopeček, J, et al. (1973) Poly[N-(2-hydroxypropyl)methacrylamide]—I. Radical Polymerization and Copolymerization. Eur. Polym. J. 9:7-14.

Lands L C. (2010) New Therapies, New Concerns: Rituximab-Associated Lung Injury. Pediatr. Nephrol. 25:1001-1003.

Liu G, et al. (2004) Pretargeting in Tumored Mice with Radiolabeled Morpholino Oligomer Showing Low Kidney Uptake. Eur. J. Nucl. Med. Mol. Imaging 31:417-424.

Liu J, et al. (2006) A Simple and Sensitive "Dipstick" Test in Serum Based on Lateral Flow Separation of Aptamer-Linked Nanostructures. Angew. Chem. Int. Ed. 45:7955-7959.

Lu Z R, et al. (1999) Polymerizable Fab' Antibody Fragments for Targeting of Anticancer Drugs. Nat. Biotechnol. 17:1101-1104.

Luo K, et al. (2011) Biodegradable Multiblock Poly[N-(2-hydroxypropyl)methacrylamide] via Reversible Addition-Fragmentation Chain Transfer Polymerization and Click Chemistry. Macromolecules; 44(8):2481-2488.

Mang'era K O, et al. (2001) Initial Investigations of $^{99m}$Tc-Labeled Morpholinos for Radiopharmaceutical Applications. Eur. J. Nucl. Med. 28:1682-1689.

Molina A. (2008) A decade of rituximab: improving survival outcomes in non-Hodgkin's lymphoma. Annu. Rev. Med. 59:237-250.

Molina A. (2008) A Decade of Rituximab: Improving Survival Outcomes in Non-Hodgkin's Lymphoma. Annu. Rev. Med. 59:237-250.

Mulvey J J, et al. (2013) Self-Assembly of Carbon Nanotubes and Antibodies on Tumours for Targeted Amplified Delivery. Nat. Nanotechnol. 8:763-771.

Nguyen J T, et al. (2001) CD45 Modulates Galectin-1-Induced T Cell Death: Regulation by Expression of Core 2 O-Glycans. J. Immunol. 167:5697-5707.

Nielsen P E. (1995) DNA Analogues with Nonphosphodiester Backbones. Annu. Rev. Biophys. Biomol. Struct. 24:167-183.

Okroj M, et al. (2013) Effector Mechanisms of Anti-CD20 Monoclonal Antibodies in B Cell Malignancies. Cancer Treat. Rev. 39:632-639.

Omelyanenko V, et al. (1998) Targetable HPMA Copolymer-Adriamycin Conjugates. Recognition, Internalization, and Subcellular Fate. J. Control. Release 53:25-37.

Pan H, et al. (2011) Backbone degradable multiblock N-(2-hydroxypropyl)methacrylamide copolymer conjugates via reversible addition-fragmentation chain transfer polymerization and thiol-ene coupling reaction. Biomacromolecules. 12(1):247-52.

Pan H, et al. (2013) Synthesis of Long-Circulating, Backbone Degradable HPMA Copolymer-Doxorubicin Conjugates and Evaluation of Molecular-Weight-Dependent Antitumor Efficacy. Macromol Biosci. 13(2):155-60.

Popov J, et al. (2011) Multivalent rituximab lipid nanoparticles as improved lymphoma therapies: indirect mechanisms of action and in vivo activity. Nanomedicine (Lond.) 6:1575-1591.

Press O W, et al. (1987) Monoclonal Antibody 1F5 (Anti-CD20) Serotherapy of Human B Cell Lymphomas. Blood 69:584-591.

Shan D, et al. (1998) Apoptosis of Malignant Human B Cells by Ligation of CD20 with Monoclonal Antibodies. Blood 91:1644-1652.

Shimizu Y, et al. (1992) Crosslinking of the T Cell-Specific Accessory Molecules CD7 and CD28 Modulates T Cell Adhesion. J. Exp. Med. 175:577-582.

Siegel R, et al. (2013) Cancer Statistics 2013. CA Cancer J. Clin. 63:11-30.

Smith M R. (2003) Rituximab (monoclonal anti-CD20 antibody): mechanisms of action and resistance. Oncogene 22:7359-7368.

Stashenko P, et al. (1980) Characterization of a human B lymphocyte-specific antigen. J. Immunol. 125:1678-1685.

Stenzel M H. (2013) Bioconjugation Using Thiols: Old Chemistry Rediscovered to Connect Polymers with Nature's Building Blocks. ACS Macro Letters. 2(1):14-18.

Šubr V, et al. (2006) Synthesis and Properties of New N-(2-Hydroxypropyl)methacrylamide Copolymers Containing Thiazolidine-2-thione Reactive Groups. React. Funct. Polym. 66:1525-1538.

Summerton J E, et al. (1997) Morpholino antisense oligomers: design, preparation, and properties. Antisense Nucleic Acid Drug Dev. 7:187-195.

Summerton J E. (2007) Morpholino, siRNA, and S-DNA compared: impact of structure and mechanism of action on off-target effects and sequence specificity. Curr Top Med Chem. 7(7):651-60.

Summerton J E. (2006) Morpholinos and PNAs compared. Peptide Nucleic Acids, Morpholinos and Related Antisense Biomolecules. Medical Intelligence Unit, Part I: 89-113.

Ulbrich K, et al. (2010) Structural and Chemical Aspects of HPMA Copolymers As Drug Carriers. Adv. Drug Deliv. Rev. 62:150-166.

Vallat L D, et al. (2007) Temporal Genetic Program Following B-Cell Receptor Cross-Linking: Altered Balance Between Proliferation and Death in Healthy and Malignant B Cells. Blood 109:3989-3997.

van der Kolk L E, et al. (2001) Complement activation plays a key role in the side-effects of rituximab treatment. Br. J. Haematol. 115:807-811.

Wu K, et al. (2012) Coiled-coil based drug-free macromolecular therapeutics: In vivo efficacy. J. Controlled Release 157:126-131.

Wu K, et al. (2010) Drug-free macromolecular therapeutics: induction of apoptosis by coiled-coil-mediated cross-linking of antigens on the cell surface. Angew. Chem. Int. Ed. 49:1451-1455.

Yang J, et al. (2006) Refolding hydrogels self-assembled from N-(2-hydroxypropyl)methacrylamide graft copolymers by antiparallel coiled-coil formation. Biomacromolecules. 7(4): 1187-1195.

Yang J, et al. (2011) Synthesis of Biodegradable Multiblock Copolymers by Click Coupling of RAFT-Generated HeterotelechelicPolyHPMA Conjugates. React Funct Polym. 71(3):294-302.

Yazici Y. (2011) Rheumatoid arthritis: When should we use rituximab to treat RA? Nat. Rev. Rheumatol. 7:379-380.

Yuan W, et al. (2008) Smart Hydrogels Containing Adenylate Kinase: Translating Substrate Recognition into Macroscopic Motion. J. Am. Chem. Soc. 130:15760-15761.

Zhang N, et al. (2005) Generation of rituximab polymer may cause hyper-cross-linking-induced apoptosis in non-Hodgkin's lymphomas. Clin. Cancer Res. 11:5971-5980.

Zhang R, et al. (2013) Synthesis and evaluation of a backbone biodegradable multiblock HPMA copolymer nanocarrier for the systemic delivery of paclitaxel. J Control Release. 166(1):66-74.

Zhou Y, et al. (2013) Biological rationale for the design of polymeric anti-cancer nanomedicines. J Drug Target. 21(1):1-26.

Zhou J, et al. (2009) Development of a Novel Pretargeting System with Bifunctional Nucleic Acid Molecules. Biochem. Biophys. Res. Commun. 386:521-525.

---

What is claimed is:

1. A method of inducing apoptosis in CD20 positive human cells, the method comprising:
   (i) contacting a population of human cells comprising CD20 positive cells with a first complex comprising a targeting moiety and a morpholino wherein the targeting moiety is an anti-CD20 antibody or an anti-CD20 Fab' fragment; and
   (ii) contacting the population of human cells with a second complex comprising a copolymer carrier and one or more morpholinos;
   wherein the morpholino of the first complex is 5' GAG TAA GCC AAG GAG AAT CAA TAT A 3' (SEQ ID NO:25) and wherein the one or more morpholinos of the second complex are 5' TAT ATT GAT TCT CCT TGG CTT ACT C 3' (SEQ ID NO:26), wherein the contacting of the human cells with the first complex and the second complex induces apoptosis of the CD20 positive human cells.

2. The method of claim 1, further comprising repeating step (i) and step (ii).

3. The method of claim 1, further comprising (iii) confirming apoptosis of the human cells.

4. The method of claim 1, wherein the cells are B-cells.

5. The method of claim 1, wherein the cells are in a subject.

6. The method of claim 5, wherein the subject has non-Hodgkin's lymphoma.

7. The method of claim 1, wherein the Fab' fragment is derived from an anti-CD20 receptor antibody.

8. The method of claim 7, wherein the anti-CD20 antibody is 1F5, rituximab, tositumomab, ibritumomab, ofatumumab, veltuzumab, ocrelizumab, ocaratuzumab, obinutuzumab, PRO131921, BCD-020, IBI-301, ublituximab, or BLX-301.

9. A method of inducing apoptosis in CD20 positive cells, the method comprising:
   contacting a population of human cells comprising CD20 positive cells with a composition comprising a first complex comprising a targeting moiety and a morpholino and a second complex comprising a complex comprising a copolymer carrier and one or more morpholinos, wherein the targeting moiety is an anti-CD20 antibody or anti-CD20 Fab' fragment, wherein the morpholino of the first complex is 5' GAG TAA GCC AAG GAG AAT CAA TAT A 3' (SEQ ID NO:25) and wherein the one or more morpholinos of the second complex are 5' TAT ATT GAT TCT CCT TGG CTT ACT C 3' (SEQ ID NO:26), wherein the contacting of the human cells with the composition induces apoptosis of the CD20 positive cells.

10. The method of claim 9, further comprising repeating the contacting of the human cells with the composition.

11. The method of claim 9, wherein the cells are B-cells.

12. The method of claim 9, wherein the cells are in a subject.

13. The method of claim 12, wherein the subject has non-Hodgkin's lymphoma.

14. The method of claim 9, wherein the anti-CD20 receptor antibody is 1F5, rituximab, tositumomab, ibritumomab, ofatumumab, veltuzumab, ocrelizumab, ocaratuzumab, obinutuzumab, PRO131921, BCD-020, IBI-301, ublituximab, or BLX-301.

* * * * *